(12) United States Patent
Gross et al.

(10) Patent No.: US 10,561,498 B2
(45) Date of Patent: Feb. 18, 2020

(54) MITRAL VALVE TREATMENT TECHNIQUES

(71) Applicant: Valtech Cardio Ltd., Or Yehuda (IL)

(72) Inventors: Amir Gross, Moshav Mazor (IL); Yossi Gross, Moshav Mazor (IL)

(73) Assignee: Valtech Cardio, Ltd., Or Yehuda (IL)

( * ) Notice: Subject to any disclaimer, the term of this patent is extended or adjusted under 35 U.S.C. 154(b) by 16 days.

(21) Appl. No.: 15/360,224

(22) Filed: Nov. 23, 2016

(65) Prior Publication Data
US 2017/0135815 A1 May 18, 2017

Related U.S. Application Data

(60) Continuation of application No. 14/084,426, filed on Nov. 19, 2013, now Pat. No. 9,526,613, which is a
(Continued)

(51) Int. Cl.
*A61F 2/24* (2006.01)
*A61B 17/00* (2006.01)

(52) U.S. Cl.
CPC .............. *A61F 2/2442* (2013.01); *A61F 2/24* (2013.01); *A61F 2/2445* (2013.01);
(Continued)

(58) Field of Classification Search
CPC ........ A61F 2/24; A61F 2/2442; A61F 2/2445; A61F 2/2457; A61F 2/2466; A61F 2/2409; A61F 2/2448
See application file for complete search history.

(56) References Cited

U.S. PATENT DOCUMENTS

| 3,604,488 A | 9/1971 | Wishart |
| 3,656,185 A | 4/1972 | Carpentier |

(Continued)

FOREIGN PATENT DOCUMENTS

| CA | 2671966 | 6/2008 |
| CN | 101653365 | 2/2010 |

(Continued)

OTHER PUBLICATIONS

O'Reilly S et al., "Heart valve surgery pushes the envelope," Medtech Insight 8(3): 73, 99-108 (2006).
(Continued)

*Primary Examiner* — Seema Mathew
(74) *Attorney, Agent, or Firm* — Thomas C. Richardson

(57) ABSTRACT

A method for treating a heart valve of a patient includes inserting into a heart and in contact with a valve surface, an implant including an elongate element and a locking mechanism coupled to the elongate element. The locking mechanism has a resting position that provides a locked state preventing movement of the elongate element with respect to the locking mechanism. The heart valve is treated by facilitating movement of the elongate element with respect to the locking mechanism by maintaining application of a force to the locking mechanism using a tool, and thereby maintaining the locking mechanism in an unlocked state during the facilitating of the movement of the elongate element with respect to the locking mechanism. Subsequently, the locking mechanism is transitioned to the resting position by decoupling the tool from the locking mechanism.

26 Claims, 17 Drawing Sheets

Related U.S. Application Data division of application No. 11/908,906, filed as application No. PCT/IL2006/000342 on Mar. 15, 2006, now Pat. No. 8,608,797.

(60) Provisional application No. 60/662,616, filed on Mar. 17, 2005, provisional application No. 60/700,542, filed on Jul. 18, 2005.

(52) U.S. Cl.
CPC .......... *A61F 2/2457* (2013.01); *A61F 2/2466* (2013.01); *A61B 2017/00243* (2013.01); *A61F 2/2409* (2013.01); *A61F 2/2418* (2013.01); *A61F 2/2448* (2013.01); *A61F 2220/0008* (2013.01); *A61F 2220/0025* (2013.01); *A61F 2250/0003* (2013.01); *A61F 2250/0004* (2013.01); *A61F 2250/0007* (2013.01); *A61F 2250/0096* (2013.01)

(56) References Cited

U.S. PATENT DOCUMENTS

| | | |
|---|---|---|
| 3,840,018 A | 10/1974 | Heifetz |
| 3,881,366 A | 5/1975 | Bradley et al. |
| 3,898,701 A | 8/1975 | La Russa |
| 4,042,979 A | 8/1977 | Angell |
| 4,118,805 A | 10/1978 | Reimels |
| 4,214,349 A | 7/1980 | Munch |
| 4,261,342 A | 4/1981 | Aranguren Duo |
| 4,290,151 A | 9/1981 | Massana |
| 4,434,828 A | 3/1984 | Trincia |
| 4,473,928 A | 10/1984 | Johnson |
| 4,602,911 A | 7/1986 | Ahmadi et al. |
| 4,625,727 A | 12/1986 | Leiboff |
| 4,712,549 A | 12/1987 | Peters et al. |
| 4,778,468 A | 10/1988 | Hunt et al. |
| 4,917,698 A | 4/1990 | Carpenter et al. |
| 4,961,738 A | 10/1990 | MacKin |
| 5,061,277 A | 10/1991 | Carpentier et al. |
| 5,064,431 A | 11/1991 | Gilbertson et al. |
| 5,104,407 A | 4/1992 | Lam et al. |
| 5,108,420 A | 4/1992 | Marks |
| 5,201,880 A | 4/1993 | Wright |
| 5,258,008 A | 11/1993 | Wilk |
| 5,300,034 A | 4/1994 | Behnke |
| 5,306,296 A | 4/1994 | Wright et al. |
| 5,325,845 A | 7/1994 | Adair |
| 5,346,498 A | 9/1994 | Greelis et al. |
| 5,450,860 A | 9/1995 | O'Connor |
| 5,474,518 A | 12/1995 | Farrer Velazquez |
| 5,477,856 A | 12/1995 | Lundquist |
| 5,593,424 A | 1/1997 | Northrup, III |
| 5,601,572 A | 2/1997 | Middleman |
| 5,626,609 A | 5/1997 | Zvenyatsky et al. |
| 5,669,919 A | 9/1997 | Sanders et al. |
| 5,674,279 A | 10/1997 | Wright et al. |
| 5,683,402 A | 11/1997 | Cosgrove et al. |
| 5,702,397 A | 12/1997 | Goble et al. |
| 5,702,398 A | 12/1997 | Tarabishy |
| 5,709,695 A | 1/1998 | Northrup, III |
| 5,716,370 A | 2/1998 | Williamson et al. |
| 5,716,397 A | 2/1998 | Myers |
| 5,728,116 A | 3/1998 | Rosenman |
| 5,730,150 A | 3/1998 | Peppel et al. |
| 5,749,371 A | 5/1998 | Zadini et al. |
| 5,810,882 A | 9/1998 | Bolduc |
| 5,824,066 A | 10/1998 | Gross |
| 5,830,221 A | 11/1998 | Stein et al. |
| 5,843,120 A | 12/1998 | Israel et al. |
| 5,855,614 A | 1/1999 | Stevens et al. |
| 5,876,373 A | 3/1999 | Giba et al. |
| 5,935,098 A | 8/1999 | Blaisdell |
| 5,957,953 A | 9/1999 | DiPoto |
| 5,961,440 A | 10/1999 | Schweich et al. |
| 5,961,539 A | 10/1999 | Northrup, III et al. |
| 5,984,959 A | 11/1999 | Robertson |
| 6,042,554 A | 3/2000 | Rosenman |
| 6,045,497 A | 4/2000 | Schweich et al. |
| 6,050,936 A | 4/2000 | Schweich et al. |
| 6,059,715 A | 5/2000 | Schweich et al. |
| 6,074,401 A | 6/2000 | Gardiner et al. |
| 6,074,417 A | 6/2000 | Peredo |
| 6,102,945 A | 8/2000 | Campbell |
| 6,106,550 A | 8/2000 | Magovern |
| 6,110,200 A | 8/2000 | Hinnenkamp |
| 6,143,024 A | 11/2000 | Campbell |
| 6,159,240 A | 12/2000 | Sparer |
| 6,165,119 A | 12/2000 | Schweich et al. |
| 6,174,332 B1 | 1/2001 | Loch |
| 6,183,411 B1 | 2/2001 | Mortier |
| 6,187,040 B1 | 2/2001 | Wright |
| 6,315,784 B1 | 2/2001 | Djurovic |
| 6,217,610 B1 | 4/2001 | Carpentier |
| 6,231,602 B1 | 5/2001 | Carpentier |
| 6,251,092 B1 | 6/2001 | Qin et al. |
| 6,296,656 B1 | 10/2001 | Bolduc et al. |
| 6,319,281 B1 | 11/2001 | Patel |
| 6,332,893 B1 | 12/2001 | Mortier et al. |
| 6,355,030 B1 | 3/2002 | Aldrich et al. |
| 6,368,348 B1 | 4/2002 | Gabbay |
| 6,402,780 B2 | 6/2002 | Williamson, IV |
| 6,406,420 B1 | 6/2002 | McCarthy et al. |
| 6,406,493 B1 | 6/2002 | Tu |
| 6,419,696 B1 | 7/2002 | Ortiz et al. |
| 6,451,054 B1 | 9/2002 | Stevens |
| 6,461,366 B1 | 10/2002 | Seguin |
| 6,470,892 B1 | 10/2002 | Forsell |
| 6,503,274 B1 | 1/2003 | Howanec |
| 6,524,338 B1 | 2/2003 | Gundry |
| 6,533,772 B1 | 3/2003 | Sherts et al. |
| 6,537,314 B2 | 3/2003 | Langberg et al. |
| 6,547,801 B1 | 4/2003 | Dargent |
| 6,554,845 B1 | 4/2003 | Fleenor |
| 6,564,805 B2 | 5/2003 | Garrison et al. |
| 6,565,603 B2 | 5/2003 | Cox |
| 6,569,198 B1 | 5/2003 | Wilson et al. |
| 6,579,297 B2 | 6/2003 | Bicek et al. |
| 6,589,160 B2 | 7/2003 | Schweich et al. |
| 6,602,288 B1 | 8/2003 | Cosgrove |
| 6,602,289 B1 | 8/2003 | Colvin et al. |
| 6,613,078 B1 | 9/2003 | Barone |
| 6,613,079 B1 | 9/2003 | Wolinsky et al. |
| 6,619,291 B2 | 9/2003 | Hlavka et al. |
| 6,626,899 B2 | 9/2003 | Houser et al. |
| 6,626,917 B1 | 9/2003 | Craig |
| 6,626,930 B1 | 9/2003 | Allen et al. |
| 6,629,534 B1 | 10/2003 | St. Goar et al. |
| 6,629,921 B1 | 10/2003 | Schweich et al. |
| 6,651,671 B1 | 11/2003 | Donlon et al. |
| 6,652,556 B1 | 11/2003 | VanTasel |
| 6,682,558 B2 | 1/2004 | Tu et al. |
| 6,689,125 B1 | 2/2004 | Keith et al. |
| 6,689,164 B1 | 2/2004 | Seguin |
| 6,695,866 B1 | 2/2004 | Kuehn et al. |
| 6,702,826 B2 | 3/2004 | Liddicoat et al. |
| 6,702,846 B2 | 3/2004 | Mikus et al. |
| 6,706,065 B2 | 3/2004 | Langberg |
| 6,709,385 B2 | 3/2004 | Forsell |
| 6,709,456 B2 | 3/2004 | Langberg et al. |
| 6,711,444 B2 | 3/2004 | Koblish |
| 6,718,985 B2 | 4/2004 | Hlavka et al. |
| 6,719,786 B2 | 4/2004 | Ryan |
| 6,723,038 B1 | 4/2004 | Schroeder et al. |
| 6,726,716 B2 | 4/2004 | Marquez |
| 6,726,717 B2 | 4/2004 | Alfieri et al. |
| 6,730,121 B2 | 5/2004 | Ortiz et al. |
| 6,749,630 B2 | 6/2004 | McCarthy et al. |
| 6,752,813 B2 | 6/2004 | Goldfarb et al. |
| 6,764,310 B1 | 7/2004 | Ichihashi et al. |
| 6,764,510 B2 | 7/2004 | Vidlund et al. |
| 6,764,810 B2 | 7/2004 | Ma et al. |
| 6,770,083 B2 | 8/2004 | Seguin |
| 6,786,924 B2 | 9/2004 | Ryan et al. |

(56) References Cited

U.S. PATENT DOCUMENTS

| | | |
|---|---|---|
| 6,786,925 B1 | 9/2004 | Schoon |
| 6,790,231 B2 | 9/2004 | Liddicoat |
| 6,797,001 B2 | 9/2004 | Mathis |
| 6,797,002 B2 | 9/2004 | Spence et al. |
| 6,802,319 B2 | 10/2004 | Stevens et al. |
| 6,805,710 B2 | 10/2004 | Bolling et al. |
| 6,805,711 B2 | 10/2004 | Quijano et al. |
| 6,855,126 B2 | 2/2005 | Flinchbaugh |
| 6,858,039 B2 | 2/2005 | McCarthy |
| 6,884,250 B2 | 4/2005 | Monassevitch et al. |
| 6,893,459 B1 | 5/2005 | Macoviak |
| 6,908,482 B2 | 6/2005 | McCarthy et al. |
| 6,918,917 B1 | 7/2005 | Nguyen et al. |
| 6,926,730 B1 | 8/2005 | Nguyen et al. |
| 6,960,217 B2 | 11/2005 | Bolduc |
| 6,964,684 B2 | 11/2005 | Ortiz |
| 6,964,686 B2 | 11/2005 | Gordon |
| 6,976,995 B2 | 12/2005 | Mathis |
| 6,986,775 B2 | 1/2006 | Morales et al. |
| 6,989,028 B2 | 1/2006 | Lashinski et al. |
| 6,997,951 B2 | 2/2006 | Solem |
| 7,004,176 B2 | 2/2006 | Lau |
| 7,011,669 B2 | 3/2006 | Kimblad |
| 7,011,682 B2 | 3/2006 | Lashinski et al. |
| 7,037,334 B1 | 5/2006 | Hlavka et al. |
| 7,077,850 B2 | 7/2006 | Kortenbach |
| 7,077,862 B2 | 7/2006 | Vidlund |
| 7,087,064 B1 | 8/2006 | Hyde |
| 7,101,395 B2 | 9/2006 | Tremulis |
| 7,101,396 B2 | 9/2006 | Artof et al. |
| 7,112,207 B2 | 9/2006 | Allen et al. |
| 7,118,595 B2 | 10/2006 | Ryan |
| 7,125,421 B2 | 10/2006 | Tremulis et al. |
| 7,150,737 B2 | 12/2006 | Purdy et al. |
| 7,159,593 B2 | 1/2007 | McCarthy |
| 7,166,127 B2 | 1/2007 | Spence |
| 7,169,187 B2 | 1/2007 | Datta et al. |
| 7,172,625 B2 | 2/2007 | Shu et al. |
| 7,175,660 B2 | 2/2007 | Cartledge et al. |
| 7,186,262 B2 | 3/2007 | Saadat |
| 7,186,264 B2 | 3/2007 | Liddicoat |
| 7,189,199 B2 | 3/2007 | McCarthy et al. |
| 7,192,443 B2 | 3/2007 | Solem |
| 7,220,277 B2 | 5/2007 | Arru et al. |
| 7,226,467 B2 | 6/2007 | Lucatero et al. |
| 7,226,477 B2 | 6/2007 | Cox |
| 7,226,647 B2 | 6/2007 | Kasperchik et al. |
| 7,229,452 B2 | 6/2007 | Kayan |
| 7,238,191 B2 | 7/2007 | Bachmann |
| 7,288,097 B2 | 10/2007 | Seguin |
| 7,294,148 B2 | 11/2007 | McCarthy |
| 7,297,150 B2 | 11/2007 | Cartledge et al. |
| 7,311,728 B2 | 12/2007 | Solem et al. |
| 7,311,729 B2 | 12/2007 | Mathis |
| 7,314,485 B2 | 1/2008 | Mathis |
| 7,316,710 B1 | 1/2008 | Cheng et al. |
| 7,329,279 B2 | 2/2008 | Haug et al. |
| 7,329,280 B2 | 2/2008 | Bolling et al. |
| 7,335,213 B1 | 2/2008 | Hyde et al. |
| 7,361,190 B2 | 4/2008 | Shoulian |
| 7,364,588 B2 | 4/2008 | Mathis |
| 7,377,941 B2 | 5/2008 | Rhee |
| 7,390,329 B2 | 6/2008 | Westra et al. |
| 7,404,824 B1 | 7/2008 | Webler et al. |
| 7,431,692 B2 | 10/2008 | Zollinger et al. |
| 7,442,207 B2 | 10/2008 | Rafiee |
| 7,452,376 B2 | 11/2008 | Lim et al. |
| 7,455,690 B2 | 11/2008 | Cartledge et al. |
| 7,485,142 B2 | 2/2009 | Milo |
| 7,485,143 B2 | 2/2009 | Webler et al. |
| 7,500,989 B2 | 3/2009 | Solem et al. |
| 7,507,252 B2 | 3/2009 | Lashinski et al. |
| 7,510,575 B2 | 3/2009 | Spenser et al. |
| 7,510,577 B2 | 3/2009 | Moaddeb |
| 7,527,647 B2 | 5/2009 | Spence |
| 7,530,995 B2 | 5/2009 | Quijano |
| 7,549,983 B2 | 6/2009 | Roue et al. |
| 7,559,936 B2 | 7/2009 | Levine |
| 7,562,660 B2 | 7/2009 | Saadat |
| 7,563,267 B2 | 7/2009 | Goldfarb et al. |
| 7,563,273 B2 | 7/2009 | Goldfarb et al. |
| 7,569,062 B1 | 8/2009 | Kuehn |
| 7,588,582 B2 | 9/2009 | Starksen et al. |
| 7,591,826 B2 | 9/2009 | Alferness |
| 7,604,646 B2 | 10/2009 | Goldfarb et al. |
| 7,608,091 B2 | 10/2009 | Goldfarb et al. |
| 7,608,103 B2 | 10/2009 | McCarthy |
| 7,618,449 B2 | 11/2009 | Tremulis et al. |
| 7,625,403 B2 | 12/2009 | Krivoruchko |
| 7,632,303 B1 | 12/2009 | Stalker et al. |
| 7,635,329 B2 | 12/2009 | Goldfarb et al. |
| 7,635,386 B1 | 12/2009 | Gammie |
| 7,655,015 B2 | 2/2010 | Goldfarb et al. |
| 7,666,204 B2 | 2/2010 | Thornton |
| 7,682,319 B2 | 3/2010 | Martin |
| 7,682,369 B2 | 3/2010 | Seguin |
| 7,686,822 B2 | 3/2010 | Shayani |
| 7,699,892 B2 | 4/2010 | Rafiee |
| 7,704,269 B2 | 4/2010 | Goar |
| 7,704,277 B2 | 4/2010 | Zakay et al. |
| 7,722,666 B2 | 5/2010 | Lafontaine |
| 7,736,388 B2 | 6/2010 | Goldfarb et al. |
| 7,748,389 B2 | 7/2010 | Salahieh et al. |
| 7,753,924 B2 | 7/2010 | Starksen et al. |
| 7,758,632 B2 | 7/2010 | Hojeibane et al. |
| 7,780,726 B2 | 8/2010 | Seguin |
| 7,871,368 B2 | 1/2011 | Zollinger et al. |
| 7,871,433 B2 | 1/2011 | Lattouf |
| 7,883,475 B2 | 2/2011 | Dupont et al. |
| 7,883,538 B2 | 2/2011 | To et al. |
| 7,927,370 B2 | 4/2011 | Webler et al. |
| 7,927,371 B2 | 4/2011 | Navia |
| 7,942,927 B2 | 5/2011 | Kaye et al. |
| 7,947,056 B2 | 5/2011 | Griego et al. |
| 7,955,377 B2 | 6/2011 | Melsheimer |
| 7,988,725 B2 | 8/2011 | Gross |
| 7,992,567 B2 | 8/2011 | Hirotsuka |
| 7,993,368 B2 | 8/2011 | Gambale et al. |
| 7,993,397 B2 | 8/2011 | Lashinski |
| 8,012,201 B2 | 9/2011 | Lashinski et al. |
| 8,034,103 B2 | 10/2011 | Burriesci |
| 8,052,592 B2 | 11/2011 | Goldfarb et al. |
| 8,057,493 B2 | 11/2011 | Goldfarb et al. |
| 8,062,355 B2 | 11/2011 | Figulla et al. |
| 8,070,804 B2 | 12/2011 | Hyde |
| 8,070,805 B2 | 12/2011 | Vidlund |
| 8,075,616 B2 | 12/2011 | Solem |
| 8,100,964 B2 | 1/2012 | Spence |
| 8,123,800 B2 | 2/2012 | McCarthy |
| 8,123,801 B2 | 2/2012 | Milo |
| 8,142,493 B2 | 3/2012 | Spence et al. |
| 8,142,495 B2 | 3/2012 | Hasenkam |
| 8,142,496 B2 | 3/2012 | Berreklouw |
| 8,147,542 B2 | 4/2012 | Maisano et al. |
| 8,152,844 B2 | 4/2012 | Rao |
| 8,163,013 B2 | 4/2012 | Machold |
| 8,187,299 B2 | 5/2012 | Goldfarb et al. |
| 8,187,324 B2 | 5/2012 | Webler |
| 8,202,315 B2 | 6/2012 | Hlavka |
| 8,206,439 B2 | 6/2012 | Gomez-Duran |
| 8,216,302 B2 | 7/2012 | Wilson et al. |
| 8,226,711 B2 | 7/2012 | Mortier |
| 8,231,671 B2 | 7/2012 | Kim |
| 8,241,351 B2 | 8/2012 | Cabiri |
| 8,252,050 B2 | 8/2012 | Maisano et al. |
| 8,262,725 B2 | 9/2012 | Subramanian |
| 8,277,502 B2 | 10/2012 | Miller |
| 8,287,584 B2 | 10/2012 | Salahieh |
| 8,287,591 B2 | 10/2012 | Keidar |
| 8,303,608 B2 | 11/2012 | Goldfarb et al. |
| 8,323,334 B2 | 12/2012 | Deem |
| 8,328,868 B2 | 12/2012 | Paul |
| 8,333,777 B2 | 12/2012 | Schaller |
| 8,343,173 B2 | 1/2013 | Starksen et al. |

(56) References Cited

U.S. PATENT DOCUMENTS

| | | |
|---|---|---|
| 8,343,174 B2 | 1/2013 | Goldfarb |
| 8,343,213 B2 | 1/2013 | Salahieh et al. |
| 8,349,002 B2 | 1/2013 | Milo |
| 8,353,956 B2 | 1/2013 | Miller et al. |
| 8,357,195 B2 | 1/2013 | Kuehn |
| 8,382,829 B1 | 2/2013 | Call et al. |
| 8,388,680 B2 | 3/2013 | Starksen et al. |
| 8,393,517 B2 | 3/2013 | Milo |
| 8,430,926 B2 | 4/2013 | Kirson |
| 8,449,599 B2 | 5/2013 | Chau et al. |
| 8,454,686 B2 | 6/2013 | Alkhatib |
| 8,460,370 B2 | 6/2013 | Zakay et al. |
| 8,460,371 B2 | 6/2013 | Hlavka et al. |
| 8,475,491 B2 | 7/2013 | Milo |
| 8,480,732 B2 | 7/2013 | Subramanian |
| 8,500,800 B2 | 8/2013 | Maisano et al. |
| 8,518,107 B2 | 8/2013 | Tsukashima et al. |
| 8,523,881 B2 | 9/2013 | Cabiri |
| 8,523,940 B2 | 9/2013 | Richardson |
| 8,545,553 B2 | 10/2013 | Zipory |
| 8,551,161 B2 | 10/2013 | Dolan |
| 8,585,755 B2 | 11/2013 | Chau et al. |
| 8,591,576 B2 | 11/2013 | Hasenkam |
| 8,608,797 B2 | 12/2013 | Gross |
| 8,628,569 B2 | 1/2014 | Benichou et al. |
| 8,628,571 B1 | 1/2014 | Hacohen et al. |
| 8,641,727 B2 | 2/2014 | Starksen et al. |
| 8,652,202 B2 | 2/2014 | Alon et al. |
| 8,652,203 B2 | 2/2014 | Quadri et al. |
| 8,679,174 B2 | 3/2014 | Ottma et al. |
| 8,685,086 B2 | 4/2014 | Navia et al. |
| 8,690,939 B2 | 4/2014 | Miller et al. |
| 8,715,342 B2 | 5/2014 | Zipory et al. |
| 8,728,097 B1 | 5/2014 | Sugimoto et al. |
| 8,728,155 B2 | 5/2014 | Montorfano et al. |
| 8,734,467 B2 | 5/2014 | Miller et al. |
| 8,736,467 B2 * | 5/2014 | Bossen ............... H03M 7/4018 341/107 |
| 8,740,920 B2 | 6/2014 | Goldfarb et al. |
| 8,747,463 B2 | 6/2014 | Fogarty et al. |
| 8,778,021 B2 | 7/2014 | Cartledge |
| 8,784,481 B2 | 7/2014 | Alkhatib et al. |
| 8,790,367 B2 | 7/2014 | Nguyen et al. |
| 8,790,394 B2 | 7/2014 | Miller et al. |
| 8,795,298 B2 | 8/2014 | Hernlund et al. |
| 8,795,355 B2 | 8/2014 | Alkhatib |
| 8,795,356 B2 | 8/2014 | Quadri et al. |
| 8,795,357 B2 | 8/2014 | Yohanan et al. |
| 8,808,366 B2 | 8/2014 | Braido et al. |
| 8,808,368 B2 | 8/2014 | Maisano et al. |
| 8,808,371 B2 | 8/2014 | Cartledge |
| 8,845,717 B2 | 9/2014 | Khairkhahan et al. |
| 8,845,723 B2 | 9/2014 | Spence et al. |
| 8,852,261 B2 | 10/2014 | White |
| 8,852,272 B2 | 10/2014 | Gross et al. |
| 8,858,623 B2 | 10/2014 | Miller et al. |
| 8,864,822 B2 | 10/2014 | Spence et al. |
| 8,870,948 B1 | 10/2014 | Erzberger et al. |
| 8,870,949 B2 | 10/2014 | Rowe |
| 8,888,843 B2 | 11/2014 | Khairkhahan et al. |
| 8,894,702 B2 | 11/2014 | Quadri et al. |
| 8,911,461 B2 | 12/2014 | Traynor et al. |
| 8,911,494 B2 | 12/2014 | Hammer et al. |
| 8,926,695 B2 | 1/2015 | Gross et al. |
| 8,926,696 B2 | 1/2015 | Cabin et al. |
| 8,926,697 B2 | 1/2015 | Gross et al. |
| 8,932,343 B2 | 1/2015 | Alkhatib et al. |
| 8,932,348 B2 | 1/2015 | Solem et al. |
| 8,940,042 B2 | 1/2015 | Miller et al. |
| 8,940,044 B2 | 1/2015 | Hammer et al. |
| 8,945,211 B2 | 2/2015 | Sugimoto |
| 8,951,285 B2 | 2/2015 | Sugimoto et al. |
| 8,951,286 B2 | 2/2015 | Sugimoto et al. |
| 8,961,595 B2 | 2/2015 | Alkhatib |
| 8,961,602 B2 | 2/2015 | Kovach et al. |
| 8,979,922 B2 | 3/2015 | Jayasinghe et al. |
| 9,005,273 B2 | 4/2015 | Salahieh et al. |
| 9,011,520 B2 | 4/2015 | Miller et al. |
| 9,011,530 B2 | 4/2015 | Reich et al. |
| 9,017,399 B2 | 4/2015 | Gross et al. |
| 9,023,100 B2 | 5/2015 | Quadri et al. |
| 9,034,032 B2 | 5/2015 | McLean et al. |
| 9,072,603 B2 | 7/2015 | Tuval et al. |
| 9,107,749 B2 | 8/2015 | Bobo et al. |
| 9,119,719 B2 | 9/2015 | Zipory et al. |
| 9,125,632 B2 | 9/2015 | Loulmet et al. |
| 9,125,742 B2 | 9/2015 | Yoganathan et al. |
| 9,173,646 B2 | 11/2015 | Fabro |
| 9,180,005 B1 | 11/2015 | Lashinski et al. |
| 9,180,007 B2 | 11/2015 | Reich et al. |
| 9,192,472 B2 | 11/2015 | Gross et al. |
| 9,226,825 B2 | 1/2016 | Starksen et al. |
| 9,241,702 B2 | 1/2016 | Maisano et al. |
| 9,265,608 B2 | 2/2016 | Miller et al. |
| 9,326,857 B2 | 5/2016 | Cartledge et al. |
| 9,351,830 B2 | 5/2016 | Gross et al. |
| 9,414,921 B2 | 8/2016 | Miller et al. |
| 9,427,316 B2 | 8/2016 | Schweich et al. |
| 9,474,606 B2 * | 10/2016 | Zipory ............... A61B 17/0401 |
| 9,526,613 B2 | 12/2016 | Gross et al. |
| 9,561,104 B2 | 2/2017 | Miller et al. |
| 2001/0021874 A1 | 9/2001 | Carpentier |
| 2001/0044656 A1 | 11/2001 | Williamson |
| 2002/0022862 A1 | 2/2002 | Grafton et al. |
| 2002/0029080 A1 | 3/2002 | Mortier |
| 2002/0042621 A1 | 4/2002 | Liddicoat |
| 2002/0082525 A1 | 6/2002 | Oslund et al. |
| 2002/0087048 A1 | 7/2002 | Brock et al. |
| 2002/0103532 A1 | 8/2002 | Langberg et al. |
| 2002/0133180 A1 | 9/2002 | Ryan et al. |
| 2002/0151916 A1 | 10/2002 | Muramatsu |
| 2002/0151961 A1 | 10/2002 | Lashinski |
| 2002/0151970 A1 | 10/2002 | Garrison |
| 2002/0169358 A1 | 11/2002 | Mortier et al. |
| 2002/0173841 A1 | 11/2002 | Ortiz et al. |
| 2002/0177904 A1 | 11/2002 | Huxel et al. |
| 2002/0188301 A1 | 12/2002 | Dallara et al. |
| 2002/0198586 A1 | 12/2002 | Inoue |
| 2003/0018358 A1 | 1/2003 | Saadat |
| 2003/0050693 A1 | 3/2003 | Quijano et al. |
| 2003/0078465 A1 | 4/2003 | Pai et al. |
| 2003/0078653 A1 | 4/2003 | Vesely |
| 2003/0083742 A1 | 5/2003 | Spence |
| 2003/0100943 A1 | 5/2003 | Bolduc |
| 2003/0105519 A1 | 6/2003 | Fasol et al. |
| 2003/0114901 A1 | 6/2003 | Loeb et al. |
| 2003/0120340 A1 | 6/2003 | Liska et al. |
| 2003/0130731 A1 | 7/2003 | Vidlund |
| 2003/0144657 A1 | 7/2003 | Bowe et al. |
| 2003/0167062 A1 | 9/2003 | Gambale et al. |
| 2003/0171760 A1 | 9/2003 | Gambale |
| 2003/0191528 A1 | 10/2003 | Quijano et al. |
| 2003/0199974 A1 | 10/2003 | Lee et al. |
| 2003/0204195 A1 | 10/2003 | Keane |
| 2003/0229350 A1 | 12/2003 | Kay |
| 2003/0229395 A1 | 12/2003 | Cox |
| 2003/0233142 A1 * | 12/2003 | Morales ........... A61B 17/00234 623/2.37 |
| 2004/0010287 A1 | 1/2004 | Bonutti |
| 2004/0019359 A1 | 1/2004 | Worley et al. |
| 2004/0019377 A1 | 1/2004 | Taylor |
| 2004/0024451 A1 | 2/2004 | Johnson et al. |
| 2004/0039442 A1 | 2/2004 | St. Goar et al. |
| 2004/0049207 A1 | 3/2004 | Goldfarb et al. |
| 2004/0059413 A1 | 3/2004 | Argento |
| 2004/0092962 A1 | 5/2004 | Thornton et al. |
| 2004/0122448 A1 | 6/2004 | Levine |
| 2004/0122514 A1 | 6/2004 | Forgarty et al. |
| 2004/0127982 A1 | 7/2004 | Machold et al. |
| 2004/0127983 A1 | 7/2004 | Mortier et al. |
| 2004/0133220 A1 | 7/2004 | Lashinski et al. |
| 2004/0133274 A1 | 7/2004 | Webler |
| 2004/0133374 A1 | 7/2004 | Kattan |
| 2004/0138744 A1 | 7/2004 | Lashinski et al. |

(56) References Cited

U.S. PATENT DOCUMENTS

| | | |
|---|---|---|
| 2004/0138745 A1 | 7/2004 | Macoviak et al. |
| 2004/0148019 A1 | 7/2004 | Vidlund et al. |
| 2004/0148020 A1 | 7/2004 | Vidlund et al. |
| 2004/0148021 A1 | 7/2004 | Cartledge et al. |
| 2004/0153146 A1 | 8/2004 | Lashinski et al. |
| 2004/0172046 A1 | 9/2004 | Hlavka |
| 2004/0176788 A1 | 9/2004 | Opolski |
| 2004/0181287 A1 | 9/2004 | Gellman |
| 2004/0186566 A1 | 9/2004 | Hindrichs |
| 2004/0193191 A1 | 9/2004 | Starksen et al. |
| 2004/0236419 A1 | 11/2004 | Milo |
| 2004/0243227 A1 | 12/2004 | Starsken et al. |
| 2004/0249453 A1 | 12/2004 | Cartledge |
| 2004/0260317 A1 | 12/2004 | Bloom et al. |
| 2004/0260393 A1 | 12/2004 | Rahdert et al. |
| 2004/0260394 A1 | 12/2004 | Douk et al. |
| 2004/0267358 A1 | 12/2004 | Reitan |
| 2005/0004668 A1 | 1/2005 | Aklog et al. |
| 2005/0010287 A1 | 1/2005 | Macoviak et al. |
| 2005/0010787 A1 | 1/2005 | Tarbouriech |
| 2005/0016560 A1 | 1/2005 | Voughlohn |
| 2005/0055038 A1 | 3/2005 | Kelleher et al. |
| 2005/0055087 A1 | 3/2005 | Starksen |
| 2005/0060030 A1 | 3/2005 | Lashinski et al. |
| 2005/0065601 A1 | 3/2005 | Lee et al. |
| 2005/0070999 A1 | 3/2005 | Spence |
| 2005/0075727 A1 | 4/2005 | Wheatley |
| 2005/0085903 A1 | 4/2005 | Lau |
| 2005/0090827 A1 | 4/2005 | Gedebou |
| 2005/0096740 A1 | 5/2005 | Langberg et al. |
| 2005/0107812 A1 | 5/2005 | Starksen et al. |
| 2005/0107871 A1 | 5/2005 | Realyvasquez et al. |
| 2005/0119734 A1 | 6/2005 | Spence |
| 2005/0125002 A1 | 6/2005 | Baran et al. |
| 2005/0125011 A1 | 6/2005 | Spence et al. |
| 2005/0131533 A1 | 6/2005 | Alfieri |
| 2005/0137686 A1 | 6/2005 | Salahieh et al. |
| 2005/0137688 A1 | 6/2005 | Salahieh et al. |
| 2005/0137695 A1 | 6/2005 | Salahieh |
| 2005/0159728 A1 | 7/2005 | Armour et al. |
| 2005/0171601 A1 | 8/2005 | Cosgrove et al. |
| 2005/0177180 A1 | 8/2005 | Kaganov |
| 2005/0177228 A1 | 8/2005 | Solem et al. |
| 2005/0187613 A1 | 8/2005 | Bolduc et al. |
| 2005/0192596 A1 | 9/2005 | Jugenheimer et al. |
| 2005/0197696 A1 | 9/2005 | Gomez Duran |
| 2005/0203549 A1 | 9/2005 | Realyvasquez |
| 2005/0203606 A1 | 9/2005 | VanCamp |
| 2005/0216039 A1 | 9/2005 | Lederman |
| 2005/0216079 A1 | 9/2005 | MaCoviak |
| 2005/0222665 A1 | 10/2005 | Aranyi |
| 2005/0222678 A1 | 10/2005 | Lashinski et al. |
| 2005/0256532 A1 | 11/2005 | Nayak et al. |
| 2005/0267478 A1 | 12/2005 | Corradi et al. |
| 2005/0273138 A1 | 12/2005 | To et al. |
| 2005/0288776 A1 | 12/2005 | Shaoulian et al. |
| 2005/0288778 A1 | 12/2005 | Shaoulian |
| 2005/0288781 A1 | 12/2005 | Moaddeb et al. |
| 2006/0004442 A1 | 1/2006 | Spenser et al. |
| 2006/0004443 A1 | 1/2006 | Liddicoat |
| 2006/0020326 A9 | 1/2006 | Bolduc et al. |
| 2006/0020327 A1 | 1/2006 | Lashinski et al. |
| 2006/0020333 A1 | 1/2006 | Lashinski et al. |
| 2006/0020336 A1 | 1/2006 | Liddicoat |
| 2006/0025787 A1 | 2/2006 | Morales et al. |
| 2006/0025855 A1 | 2/2006 | Lashinski et al. |
| 2006/0025858 A1 | 2/2006 | Alameddine |
| 2006/0030885 A1 | 2/2006 | Hyde |
| 2006/0041319 A1 | 2/2006 | Taylor et al. |
| 2006/0052868 A1 | 3/2006 | Mortier |
| 2006/0058871 A1 | 3/2006 | Zakay et al. |
| 2006/0069429 A1 | 3/2006 | Spence et al. |
| 2006/0074486 A1 | 4/2006 | Liddicoat |
| 2006/0085012 A1 | 4/2006 | Dolan |
| 2006/0095009 A1 | 5/2006 | Lampropoulos |
| 2006/0106423 A1 | 5/2006 | Weisel |
| 2006/0116757 A1 | 6/2006 | Lashinski et al. |
| 2006/0122633 A1 | 6/2006 | To |
| 2006/0129166 A1 | 6/2006 | Lavelle |
| 2006/0149280 A1 | 7/2006 | Harvine et al. |
| 2006/0149368 A1 | 7/2006 | Spence |
| 2006/0161265 A1 | 7/2006 | Levine et al. |
| 2006/0184240 A1 | 8/2006 | Jiminez |
| 2006/0184242 A1 | 8/2006 | Lichtenstein |
| 2006/0195134 A1 | 8/2006 | Crittenden |
| 2006/0241622 A1 | 10/2006 | Zergiebel |
| 2006/0241656 A1 | 10/2006 | Starksen et al. |
| 2006/0241748 A1 | 10/2006 | Lee et al. |
| 2006/0247763 A1 | 11/2006 | Slater |
| 2006/0259135 A1 | 11/2006 | Navia |
| 2006/0271175 A1 | 11/2006 | Woolfson |
| 2006/0282161 A1 | 12/2006 | Huyn et al. |
| 2006/0287661 A1 | 12/2006 | Bolduc |
| 2006/0287716 A1 | 12/2006 | Banbury et al. |
| 2007/0001627 A1 | 1/2007 | Lin et al. |
| 2007/0016287 A1 | 1/2007 | Cartledge et al. |
| 2007/0016288 A1 | 1/2007 | Gurskis |
| 2007/0021781 A1 | 1/2007 | Jervis |
| 2007/0027533 A1 | 2/2007 | Douk |
| 2007/0027536 A1 | 2/2007 | Mihaljevic et al. |
| 2007/0038221 A1 | 2/2007 | Fine |
| 2007/0039425 A1 | 2/2007 | Wang |
| 2007/0049942 A1 | 3/2007 | Hindrichs et al. |
| 2007/0049970 A1 | 3/2007 | Belef et al. |
| 2007/0051377 A1 | 3/2007 | Douk et al. |
| 2007/0055206 A1 | 3/2007 | To et al. |
| 2007/0061010 A1 | 3/2007 | Hauser et al. |
| 2007/0066863 A1 | 3/2007 | Rafiee et al. |
| 2007/0078297 A1 | 4/2007 | Rafiee et al. |
| 2007/0080188 A1 | 4/2007 | Spence et al. |
| 2007/0083168 A1 | 4/2007 | Whiting et al. |
| 2007/0100427 A1 | 5/2007 | Perouse |
| 2007/0106328 A1 | 5/2007 | Wardle et al. |
| 2007/0112359 A1 | 5/2007 | Kimura |
| 2007/0112422 A1 | 5/2007 | Dehdashtian |
| 2007/0112425 A1 | 5/2007 | Schaller et al. |
| 2007/0118151 A1 | 5/2007 | Davidson |
| 2007/0118154 A1 | 5/2007 | Crabtree |
| 2007/0118213 A1 | 5/2007 | Loulmet |
| 2007/0118215 A1 | 5/2007 | Moaddeb |
| 2007/0142907 A1 | 6/2007 | Moaddeb |
| 2007/0162111 A1 | 7/2007 | Fukamachi et al. |
| 2007/0198082 A1 | 8/2007 | Kapadia et al. |
| 2007/0213582 A1 | 9/2007 | Zollinger et al. |
| 2007/0219558 A1 | 9/2007 | Deutsch |
| 2007/0233239 A1 | 10/2007 | Navia et al. |
| 2007/0239208 A1 | 10/2007 | Crawford |
| 2007/0244555 A1 | 10/2007 | Rafiee et al. |
| 2007/0244556 A1 | 10/2007 | Rafiee et al. |
| 2007/0244557 A1 | 10/2007 | Rafiee et al. |
| 2007/0250160 A1 | 10/2007 | Rafiee |
| 2007/0255397 A1 | 11/2007 | Ryan et al. |
| 2007/0255400 A1 | 11/2007 | Parravicini et al. |
| 2007/0270755 A1 | 11/2007 | Von Oepen et al. |
| 2007/0270943 A1 | 11/2007 | Solem et al. |
| 2007/0276437 A1 | 11/2007 | Call |
| 2007/0282375 A1 | 12/2007 | Hindrichs et al. |
| 2007/0282429 A1 | 12/2007 | Hauser et al. |
| 2007/0295172 A1 | 12/2007 | Swartz |
| 2007/0299424 A1 | 12/2007 | Cummings et al. |
| 2008/0004697 A1 | 1/2008 | Lichtenstein et al. |
| 2008/0027483 A1 | 1/2008 | Cartledge |
| 2008/0027555 A1 | 1/2008 | Hawkins |
| 2008/0035160 A1 | 2/2008 | Wodson et al. |
| 2008/0039935 A1 | 2/2008 | Buch |
| 2008/0051703 A1 | 2/2008 | Thornton et al. |
| 2008/0058595 A1 | 3/2008 | Snoke et al. |
| 2008/0065011 A1 | 3/2008 | Marchand et al. |
| 2008/0065204 A1 | 3/2008 | Mackoviak |
| 2008/0071366 A1 | 3/2008 | Tuval |
| 2008/0086138 A1 | 4/2008 | Stone et al. |
| 2008/0086203 A1 | 4/2008 | Roberts |
| 2008/0091257 A1 | 4/2008 | Andreas et al. |
| 2008/0097523 A1 | 4/2008 | Bolduc et al. |

(56) References Cited

U.S. PATENT DOCUMENTS

| | | |
|---|---|---|
| 2008/0103572 A1 | 5/2008 | Gerber |
| 2008/0125861 A1 | 5/2008 | Webler et al. |
| 2008/0140116 A1 | 6/2008 | Bonutti |
| 2008/0167714 A1 | 7/2008 | St. Goar |
| 2008/0177382 A1 | 7/2008 | Hyde et al. |
| 2008/0195126 A1 | 8/2008 | Solem |
| 2008/0195200 A1 | 8/2008 | Vidlund |
| 2008/0208265 A1 | 8/2008 | Frazier et al. |
| 2008/0221672 A1 | 9/2008 | Lamphere |
| 2008/0243245 A1 | 10/2008 | Thambar |
| 2008/0262480 A1 | 10/2008 | Stahler et al. |
| 2008/0262609 A1 | 10/2008 | Gross et al. |
| 2008/0275300 A1 | 11/2008 | Rothe |
| 2008/0275469 A1 | 11/2008 | Fanton |
| 2008/0275551 A1 | 11/2008 | Alfieri |
| 2008/0281411 A1 | 11/2008 | Berreklouw |
| 2008/0288044 A1 | 11/2008 | Osborne |
| 2008/0288062 A1 | 11/2008 | Andrieu et al. |
| 2008/0300537 A1 | 12/2008 | Bowman |
| 2008/0300629 A1 | 12/2008 | Surti |
| 2009/0028670 A1 | 1/2009 | Garcia et al. |
| 2009/0043153 A1 | 2/2009 | Zollinger et al. |
| 2009/0043381 A1 | 2/2009 | Macoviak |
| 2009/0054969 A1 | 2/2009 | Salahieh |
| 2009/0062866 A1 | 3/2009 | Jackson |
| 2009/0076586 A1 | 3/2009 | Hauser |
| 2009/0076600 A1 | 3/2009 | Quinn |
| 2009/0088837 A1 | 4/2009 | Gillinov |
| 2009/0093877 A1 | 4/2009 | Keidar et al. |
| 2009/0099650 A1 | 4/2009 | Bolduc |
| 2009/0105816 A1 | 4/2009 | Olsen et al. |
| 2009/0125102 A1 | 5/2009 | Cartledge |
| 2009/0149872 A1 | 6/2009 | Gross et al. |
| 2009/0177274 A1 | 6/2009 | Scorsin |
| 2009/0171439 A1 | 7/2009 | Nissl |
| 2009/0177266 A1 | 7/2009 | Powell et al. |
| 2009/0177277 A1 | 7/2009 | Milo |
| 2009/0222083 A1 | 9/2009 | Nguyen et al. |
| 2009/0248148 A1 | 10/2009 | Shaolian |
| 2009/0254103 A1 | 10/2009 | Deustch |
| 2009/0259307 A1 | 10/2009 | Gross et al. |
| 2009/0264994 A1 | 10/2009 | Saadat |
| 2009/0264995 A1 | 10/2009 | Subramanian |
| 2009/0287231 A1 | 11/2009 | Brooks et al. |
| 2009/0287304 A1 | 11/2009 | Dahlgren |
| 2009/0299409 A1 | 12/2009 | Coe |
| 2009/0326648 A1 | 12/2009 | Machold et al. |
| 2010/0001038 A1 | 1/2010 | Levin |
| 2010/0010538 A1 | 1/2010 | Juravic |
| 2010/0023117 A1 | 1/2010 | Yoganathan |
| 2010/0023118 A1 | 1/2010 | Medlock et al. |
| 2010/0030014 A1 | 2/2010 | Ferrazzi |
| 2010/0030328 A1 | 2/2010 | Seguin |
| 2010/0042147 A1 | 2/2010 | Janovsky et al. |
| 2010/0049313 A1 | 2/2010 | Alon et al. |
| 2010/0063542 A1 | 3/2010 | Van der Burg |
| 2010/0063550 A1 | 3/2010 | Felix |
| 2010/0063586 A1 | 3/2010 | Hasenkam |
| 2010/0076499 A1 | 3/2010 | McNamara et al. |
| 2010/0094248 A1 | 4/2010 | Nguyen et al. |
| 2010/0114180 A1 | 5/2010 | Rock |
| 2010/0121349 A1 | 5/2010 | Meier |
| 2010/0121435 A1 | 5/2010 | Subramanian et al. |
| 2010/0121437 A1 | 5/2010 | Subramanian et al. |
| 2010/0130992 A1 | 5/2010 | Machold et al. |
| 2010/0152845 A1 | 6/2010 | Bloom |
| 2010/0161041 A1 | 6/2010 | Maisano et al. |
| 2010/0161042 A1 | 6/2010 | Maisano et al. |
| 2010/0161043 A1 | 6/2010 | Maisano et al. |
| 2010/0161047 A1 | 6/2010 | Cabiri |
| 2010/0168845 A1 | 7/2010 | Wright |
| 2010/0174358 A1 | 7/2010 | Rabkin et al. |
| 2010/0179574 A1 | 7/2010 | Longoria |
| 2010/0198347 A1 | 8/2010 | Zakay et al. |
| 2010/0211166 A1 | 8/2010 | Miller et al. |
| 2010/0217184 A1 | 8/2010 | Koblish et al. |
| 2010/0217382 A1 | 8/2010 | Chau |
| 2010/0234935 A1 | 9/2010 | Bashiri et al. |
| 2010/0249915 A1 | 9/2010 | Zhang |
| 2010/0249920 A1 | 9/2010 | Bolling |
| 2010/0262232 A1 | 10/2010 | Annest |
| 2010/0262233 A1 | 10/2010 | He |
| 2010/0280603 A1 | 11/2010 | Maisano et al. |
| 2010/0280604 A1 | 11/2010 | Zipory |
| 2010/0280605 A1 | 11/2010 | Hammer |
| 2010/0286628 A1 | 11/2010 | Gross |
| 2010/0286767 A1 | 11/2010 | Zipory |
| 2010/0305475 A1 | 12/2010 | Hinchliffe et al. |
| 2010/0324598 A1 | 12/2010 | Anderson |
| 2011/0004210 A1 | 1/2011 | Johnson |
| 2011/0004298 A1 | 1/2011 | Lee et al. |
| 2011/0009956 A1 | 1/2011 | Cartledge et al. |
| 2011/0011917 A1 | 1/2011 | Loulmet |
| 2011/0026208 A1 | 2/2011 | Otsuro et al. |
| 2011/0029066 A1 | 2/2011 | Gilad |
| 2011/0035000 A1 | 2/2011 | Nieminen et al. |
| 2011/0066231 A1 | 3/2011 | Cartledge |
| 2011/0067770 A1 | 3/2011 | Pederson et al. |
| 2011/0071626 A1 | 3/2011 | Wright et al. |
| 2011/0082538 A1 | 4/2011 | Dahlgren et al. |
| 2011/0087146 A1 | 4/2011 | Ryan et al. |
| 2011/0093002 A1 | 4/2011 | Rucker et al. |
| 2011/0106245 A1 | 5/2011 | Miller et al. |
| 2011/0106247 A1 | 5/2011 | Miller |
| 2011/0118832 A1 | 5/2011 | Punjabi |
| 2011/0137410 A1 | 6/2011 | Hacohen |
| 2011/0144703 A1 | 6/2011 | Krause |
| 2011/0166649 A1 | 7/2011 | Gross |
| 2011/0184510 A1 | 7/2011 | Maisano et al. |
| 2011/0190879 A1 | 8/2011 | Bobo et al. |
| 2011/0202130 A1 | 8/2011 | Cartledge |
| 2011/0208283 A1 | 8/2011 | Rust |
| 2011/0224785 A1 | 9/2011 | Hacohen |
| 2011/0230941 A1 | 9/2011 | Markus |
| 2011/0230961 A1 | 9/2011 | Langer |
| 2011/0238088 A1 | 9/2011 | Bolduc et al. |
| 2011/0257433 A1 | 10/2011 | Walker |
| 2011/0257633 A1 | 10/2011 | Cartledge |
| 2011/0257728 A1 | 10/2011 | Kuehn |
| 2011/0264208 A1 | 10/2011 | Duffy |
| 2011/0276062 A1 | 11/2011 | Bolduc |
| 2011/0282361 A1 | 11/2011 | Miller et al. |
| 2011/0288435 A1 | 11/2011 | Christy et al. |
| 2011/0288635 A1 | 11/2011 | Miller |
| 2011/0301498 A1 | 12/2011 | Maenhout et al. |
| 2011/0301698 A1 | 12/2011 | Miller et al. |
| 2012/0022557 A1 | 1/2012 | Cabiri |
| 2012/0022639 A1 | 1/2012 | Hacohen et al. |
| 2012/0022640 A1 | 1/2012 | Gross et al. |
| 2012/0022644 A1 | 1/2012 | Reich |
| 2012/0035712 A1 | 2/2012 | Maisano et al. |
| 2012/0078355 A1 | 3/2012 | Zipory |
| 2012/0078359 A1 | 3/2012 | Li et al. |
| 2012/0089022 A1 | 4/2012 | House et al. |
| 2012/0095552 A1 | 4/2012 | Spence |
| 2012/0109155 A1 | 5/2012 | Robinson et al. |
| 2012/0136436 A1 | 5/2012 | Cabiri |
| 2012/0143323 A1 | 6/2012 | Hasenkam |
| 2012/0150290 A1 | 6/2012 | Gabbay |
| 2012/0158021 A1 | 6/2012 | Morrill |
| 2012/0179086 A1 | 7/2012 | Shank |
| 2012/0191182 A1 | 7/2012 | Hauser et al. |
| 2012/0197388 A1 | 8/2012 | Khairkhahan et al. |
| 2012/0226349 A1 | 9/2012 | Tuval et al. |
| 2012/0239142 A1 | 9/2012 | Liu et al. |
| 2012/0245604 A1 | 9/2012 | Tegzes |
| 2012/0271198 A1 | 10/2012 | Whittaker et al. |
| 2012/0283757 A1 | 11/2012 | Miller |
| 2012/0296349 A1 | 11/2012 | Smith et al. |
| 2012/0296417 A1 | 11/2012 | Hill et al. |
| 2012/0296419 A1 | 11/2012 | Richardson |
| 2012/0123531 A1 | 12/2012 | Tsukashima et al. |
| 2012/0310330 A1 | 12/2012 | Buchbinder et al. |
| 2012/0323313 A1 | 12/2012 | Seguin |

(56) References Cited

U.S. PATENT DOCUMENTS

| | | |
|---|---|---|
| 2012/0330410 A1 | 12/2012 | Hammer |
| 2012/0330411 A1 | 12/2012 | Gross |
| 2013/0023758 A1 | 1/2013 | Fabro |
| 2013/0030522 A1 | 1/2013 | Rowe et al. |
| 2013/0035759 A1 | 2/2013 | Gross et al. |
| 2013/0046373 A1 | 2/2013 | Cartledge et al. |
| 2013/0079873 A1 | 3/2013 | Migliazza |
| 2013/0297013 A1 | 3/2013 | Klima et al. |
| 2013/0085529 A1 | 4/2013 | Housman |
| 2013/0090724 A1 | 4/2013 | Subramanian |
| 2013/0096672 A1 | 4/2013 | Reich |
| 2013/0096673 A1 | 4/2013 | Hill |
| 2013/0116776 A1 | 5/2013 | Gross et al. |
| 2013/0116780 A1 | 5/2013 | Miller |
| 2013/0123910 A1 | 5/2013 | Cartledge |
| 2013/0131791 A1 | 5/2013 | Hlavka et al. |
| 2013/0131792 A1 | 5/2013 | Miller |
| 2013/0166017 A1 | 6/2013 | Cartledge et al. |
| 2013/0172992 A1 | 7/2013 | Gross et al. |
| 2013/0190863 A1 | 7/2013 | Call et al. |
| 2013/0190866 A1 | 7/2013 | Zipory |
| 2013/0197632 A1 | 8/2013 | Kovach |
| 2013/0204361 A1 | 8/2013 | Adams |
| 2013/0226289 A1 | 8/2013 | Shaolian |
| 2013/0226290 A1 | 8/2013 | Yellin et al. |
| 2013/0268069 A1 | 10/2013 | Zakai et al. |
| 2013/0289718 A1 | 10/2013 | Tsukashima et al. |
| 2013/0304093 A1 | 11/2013 | Serina et al. |
| 2013/0325118 A1 | 12/2013 | Cartledge |
| 2014/0018914 A1 | 1/2014 | Zipory et al. |
| 2014/0088368 A1 | 3/2014 | Park |
| 2014/0094826 A1 | 4/2014 | Sutherland et al. |
| 2014/0094903 A1 | 4/2014 | Miller et al. |
| 2014/0094906 A1 | 4/2014 | Spence et al. |
| 2014/0135799 A1 | 5/2014 | Henderson |
| 2014/0142619 A1 | 5/2014 | Serina et al. |
| 2014/0142695 A1 | 5/2014 | Gross et al. |
| 2014/0148849 A1 | 5/2014 | Serina et al. |
| 2014/0148898 A1 | 5/2014 | Gross et al. |
| 2014/0155783 A1 | 6/2014 | Starksen et al. |
| 2014/0163670 A1 | 6/2014 | Alon et al. |
| 2014/0163690 A1 | 6/2014 | White |
| 2014/0188108 A1 | 7/2014 | Goodine et al. |
| 2014/0188140 A1 | 7/2014 | Meier et al. |
| 2014/0188215 A1 | 7/2014 | Hlavka et al. |
| 2014/0194976 A1 | 7/2014 | Starksen et al. |
| 2014/0207231 A1 | 7/2014 | Hacohen et al. |
| 2014/0222137 A1 | 8/2014 | Miller et al. |
| 2014/0243859 A1 | 8/2014 | Robinson |
| 2014/0243894 A1 | 8/2014 | Groothuis et al. |
| 2014/0243963 A1 | 8/2014 | Sheps et al. |
| 2014/0257475 A1 | 9/2014 | Gross et al. |
| 2014/0275757 A1 | 9/2014 | Goodwin et al. |
| 2014/0276648 A1 | 9/2014 | Hammer et al. |
| 2014/0296962 A1 | 10/2014 | Cartledge et al. |
| 2014/0303649 A1 | 10/2014 | Nguyen et al. |
| 2014/0303720 A1 | 10/2014 | Sugimoto et al. |
| 2014/0309661 A1 | 10/2014 | Sheps et al. |
| 2014/0309730 A1 | 10/2014 | Alon |
| 2014/0324164 A1 | 10/2014 | Gross et al. |
| 2014/0343668 A1 | 11/2014 | Zipory et al. |
| 2014/0379006 A1 | 12/2014 | Sutherland et al. |
| 2015/0012087 A1 | 1/2015 | Miller et al. |
| 2015/0018940 A1 | 1/2015 | Quill et al. |
| 2015/0051697 A1 | 2/2015 | Spence et al. |
| 2015/0081014 A1 | 3/2015 | Gross et al. |
| 2015/0105855 A1 | 4/2015 | Cabiri et al. |
| 2015/0112432 A1 | 4/2015 | Reich et al. |
| 2015/0127097 A1 | 5/2015 | Neumann et al. |
| 2015/0182336 A1 | 7/2015 | Zipory et al. |
| 2015/0230924 A1 | 8/2015 | Miller |
| 2015/0272586 A1 | 10/2015 | Herman et al. |
| 2015/0272734 A1 | 10/2015 | Sheps et al. |
| 2015/0282931 A1 | 10/2015 | Brunnett et al. |
| 2015/0297212 A1 | 10/2015 | Reich et al. |
| 2015/0351906 A1 * | 12/2015 | Hammer ............... A61F 2/2427 623/2.11 |
| 2016/0008132 A1 | 1/2016 | Cabiri et al. |
| 2016/0058557 A1 | 3/2016 | Reich et al. |
| 2016/0113767 A1 | 4/2016 | Miller et al. |
| 2016/0158008 A1 | 6/2016 | Miller et al. |
| 2016/0242762 A1 | 8/2016 | Gilmore et al. |
| 2016/0262755 A1 | 9/2016 | Zipory et al. |
| 2016/0302917 A1 | 10/2016 | Schewel |
| 2016/0317302 A1 | 11/2016 | Madjarov et al. |
| 2016/0324633 A1 | 11/2016 | Gross et al. |
| 2016/0361168 A1 | 12/2016 | Gross et al. |
| 2016/0361169 A1 | 12/2016 | Gross et al. |
| 2016/0367368 A1 * | 12/2016 | Vidlund ............... A61B 90/06 |
| 2017/0000609 A1 | 1/2017 | Gross et al. |
| 2018/0133008 A1 * | 5/2018 | Kizuka ............ A61B 17/00234 |

FOREIGN PATENT DOCUMENTS

| | | |
|---|---|---|
| EP | 0611561 | 8/1994 |
| EP | 06/14342 | 9/1994 |
| EP | 10/06905 | 6/2000 |
| EP | 0954257 | 8/2000 |
| EP | 1258437 | 11/2002 |
| EP | 0871417 | 10/2003 |
| EP | 1266641 | 10/2004 |
| EP | 1034753 | 2/2005 |
| EP | 1258232 | 1/2006 |
| EP | 1990014 | 11/2008 |
| EP | 1562522 | 12/2008 |
| EP | 1420723 | 1/2009 |
| EP | 1903991 | 9/2009 |
| EP | 1418865 | 10/2009 |
| EP | 2119399 | 11/2009 |
| EP | 1531762 | 4/2010 |
| EP | 1450733 | 2/2011 |
| EP | 1861045 | 3/2015 |
| EP | 1465555 | 5/2015 |
| IL | 223448 | 12/2012 |
| WO | 92/05093 | 4/1992 |
| WO | 93/10714 | 6/1993 |
| WO | 1993/015690 | 8/1993 |
| WO | 96/39963 | 12/1996 |
| WO | 96/40344 | 12/1996 |
| WO | 97/01369 | 1/1997 |
| WO | 98/46149 | 10/1998 |
| WO | 1999/030647 | 6/1999 |
| WO | 99/033414 | 7/1999 |
| WO | 99/063907 | 12/1999 |
| WO | 99/063910 | 12/1999 |
| WO | 2000/009048 | 2/2000 |
| WO | 00/22981 | 4/2000 |
| WO | 01/26586 | 4/2001 |
| WO | 01/56457 | 8/2001 |
| WO | 2001/087191 | 11/2001 |
| WO | 02/085250 | 10/2002 |
| WO | 02/085251 | 10/2002 |
| WO | 02/085252 | 10/2002 |
| WO | 03/028558 | 4/2003 |
| WO | 03/047467 | 6/2003 |
| WO | 2003/049647 | 6/2003 |
| WO | 2003/105667 | 12/2003 |
| WO | 2004/012583 | 2/2004 |
| WO | 2004/019816 | 3/2004 |
| WO | 2004/019826 | 3/2004 |
| WO | 04/103434 | 12/2004 |
| WO | 05/021063 | 3/2005 |
| WO | 05/046488 | 5/2005 |
| WO | 2005/062931 | 7/2005 |
| WO | 06/012013 | 2/2006 |
| WO | 06/012038 | 2/2006 |
| WO | 06/086434 | 8/2006 |
| WO | 06/097931 | 9/2006 |
| WO | 06/105084 | 10/2006 |
| WO | 06/116558 | 11/2006 |
| WO | 07/011799 | 1/2007 |
| WO | 2007/080595 | 7/2007 |
| WO | 07/121314 | 10/2007 |
| WO | 07/136783 | 11/2007 |

(56) References Cited

FOREIGN PATENT DOCUMENTS

| WO | 07/136981 | 11/2007 |
|---|---|---|
| WO | 2008/014144 | 1/2008 |
| WO | 2008/031103 | 3/2008 |
| WO | 08/068756 | 6/2008 |
| WO | 2009/160631 | 10/2009 |
| WO | 10/004546 | 1/2010 |
| WO | 2010/000454 | 1/2010 |
| WO | 2010/006905 | 1/2010 |
| WO | 2010/044851 | 4/2010 |
| WO | 2010/065274 | 6/2010 |
| WO | 10/073246 | 7/2010 |
| WO | 2010/085649 | 7/2010 |
| WO | 2010/128502 | 11/2010 |
| WO | 2010/128503 | 11/2010 |
| WO | 2010/150178 | 12/2010 |
| WO | 2011/051942 | 5/2011 |
| WO | 11/067770 | 6/2011 |
| WO | 2011/089401 | 7/2011 |
| WO | 2011/089601 | 7/2011 |
| WO | 2011/111047 | 9/2011 |
| WO | 2011/148374 | 12/2011 |
| WO | 2011/154942 | 12/2011 |
| WO | 2012/011108 | 1/2012 |
| WO | 2012/014201 | 2/2012 |
| WO | 2012/068541 | 5/2012 |
| WO | 2012/106346 | 8/2012 |
| WO | 2012/176195 | 12/2012 |
| WO | 2013/021374 | 2/2013 |
| WO | 2013/021375 | 2/2013 |
| WO | 2013/069019 | 5/2013 |
| WO | 2013/078497 | 6/2013 |
| WO | 2013/088327 | 6/2013 |
| WO | 2014/064694 | 5/2014 |
| WO | 2014/064695 | 5/2014 |
| WO | 2014/064964 | 5/2014 |
| WO | 2014/076696 | 5/2014 |
| WO | 2014/087402 | 6/2014 |
| WO | 2014/108903 | 7/2014 |
| WO | 2014/115149 | 7/2014 |
| WO | 2014/195786 | 12/2014 |
| WO | 2015/059699 | 4/2015 |
| WO | 2015/193728 | 12/2015 |
| WO | 2016/059639 | 4/2016 |
| WO | 2016/087934 | 6/2016 |
| WO | 2016/174669 | 11/2016 |

OTHER PUBLICATIONS

Dieter RS, "Percutaneous valve repair: Update on mitral regurgitation and endovascular approaches to the mitral valve," Applications in Imaging, Cardiac Interventions, Supported by an educational grant from Amersham Health pp. 11-14 (2003).
Swain CP et al., "An endoscopically deliverable tissue-transfixing device for securing biosensors in the gastrointestinal tract," Gastrointestinal Endoscopy 40(6): 730-734 (1994).
Odell JA et al., "Early Results o4yf a Simplified Method of Mitral Valve Annuloplasty," Circulation 92:150-154 (1995).
U.S. Appl. No. 60/873,075, filed Dec. 5, 2006.
An International Preliminary Report on Patentability dated Nov. 9, 2011, which issued during the prosecution of Applicant's PCT/IL2010/000357.
U.S. Appl. No. 60/902,146, filed Feb. 16, 2007.
An International Preliminary Report on Patentability dated Jun. 5, 2012, which issued during the prosecution of Applicant's PCT/IL2010/001024.
U.S. Appl. No. 61/001,013, filed Oct. 29, 2007.
An International Preliminary Report on Patentability dated Nov. 27, 2012, which issued during the prosecution of Applicant's PCT/IL2011/000404.
U.S. Appl. No. 61/132,295, filed Jun. 16, 2008.
Notice of Allowance dated Apr. 27, 2012, which issued during the prosecution of U.S. Appl. No. 12/341,960.
"Two dimensional real-time ultrasonic imaging of the heart and great vessels", Mayo Clin Proc. vol. 53:271-303, 1978.
An Office Action dated Mar. 29, 2011, which issued during the prosecution of U.S. Appl. No. 12/341,960.
An Office Action dated Aug. 2, 2011, which issued during the prosecution of U.S. Appl. No. 12/435,291.
A Restriction Requirement dated Mar. 30, 2012, which issued during the prosecution of U.S. Appl. No. 12/785,717.
An International Search Report and a Written Opinion both dated Jun. 10, 2010, which issued during the prosecution of Applicant's PCT/IL09/01209.
An Office Action dated Jan. 27, 2012, which issued during the prosecution of U.S. Appl. No. 12/548,991.
An Office Action dated Apr. 6, 2010, which issued during the prosecution of Applicant's U.S. Appl. No. 12/484,512.
An Office Action dated Nov. 5, 2012, which issued during the prosecution of U.S. Appl. No. 12/795,026.
A Notice of Allowance dated Sep. 16, 2016, which issued during the prosecution of U.S. Appl. No. 14/027,934.
An International Search Report and a Written Opinion both dated Aug. 17, 2010, which issued during the prosecution of Applicant's PCT/IL10/00357.
An Office Action dated Sep. 16, 2009 which issued during the prosecution of U.S. Appl. No. 11/950,930.
Alfieri et al., "An effective technique to correct anterior mitral leaflet prolapse," J Card 14(6):468-470 (1999).
A Restriction Requirement dated Nov. 19, 2012, which issued during the prosecution of U.S. Appl. No. 12/926,673.
Alfieri et al., "The double orifice technique in mitral valve repair: a simple solution for complex problems," Journal of Thoracic Cardiovascular Surgery 122:674-681 (2001).
A Supplementary European Search Report dated Jan. 20, 2015, which issued during the prosecution of European Patent Application No. 12803037.6.
An International Preliminary Report on Patentability dated Jun. 29, 2011, which issued during the prosecution of Applicant's PCT/IL2009/001209.
Alfieri, "The edge-to-edge repair of the mitral valve," [Abstract] 6th Annual NewEra Cardiac Care: Innovation & Technology, Heart Surgery Forum pp. 103. (2000).
Dang NC et al. "Simplified Placement of Multiple Artificial Mitral Valve Chords," The Heart Surgery Forum #2005-1005, 8 (3) (2005).
An International Search Report and A Written Opinion both dated Feb. 10, 2011, which issued during the prosecution of Applicant's PCT/IL10/00890.
Alfieri et al. "Novel Suture Device for Beating-Heart Mitral Leaflet Approximation", Ann Thorac Surg. 2002, 74:1488-1493.
A Notice of Allowance dated Jun. 26, 2012, which issued during the prosecution of U.S. Appl. No. 12/608,316.
A Notice of Allowance dated Jul. 30, 2015, which issued during the prosecution of U.S. Appl. No. 13/319,007.
An Office Action dated Jan. 23, 2012, which issued during the prosecution of U.S. Appl. No. 12/692,061.
An International Search Report dated May 19, 2011, which issued during the prosecution of Applicant's PCT/IL2011/00064.
A Supplementary European Search Report dated Feb. 1, 2011, which issued during the prosecution of European Patent Application No. EP 07849540.
An International Search Report together with Written Opinion both dated Mar. 30, 2011, which issued during the prosecution of Applicant's PCT/IL2010/001024.
An Office Action dated Aug. 6, 2012, which issued during the prosecution of U.S. Appl. No. 12/548,991.
An Office Action dated Jul. 20, 2012, which issued during the prosecution of U.S. Appl. No. 12/843,412.
Notice of Allowance dated May 6, 2016, which issued during the prosecution of U.S. Appl. No. 14/667,090.
An Office Action dated Aug. 24, 2012, which issued during the prosecution of U.S. Appl. No. 12/563,930.
An Office Action dated May 10, 2012, which issued during the prosecution of U.S. Appl. No. 12/795,026.
An Office Action dated Mar. 9, 2012, which issued during the prosecution of U.S. Appl. No. 12/689,635.

(56) References Cited

OTHER PUBLICATIONS

A Restriction Requirement dated Sep. 14, 2012, which issued during the prosecution of U.S. Appl. No. 12/795,192.
Notice of Allowance dated Apr. 12, 2016, which issued during the prosecution of U.S. Appl. No. 14/667,090.
An Office Action dated Sep. 28, 2011, which issued during the prosecution of U.S. Appl. No. 12/437,103.
An International Search Report and Written Opinion dated Nov. 8, 2010, which issued during the prosecution of Applicant's PCT/IL2010/000358.
An Office Action dated Dec. 29, 2011, which issued during the prosecution of U.S. Appl. No. 12/563,952.
An International Search Report and a Written Opinion both dated Nov. 23, 2011, which issued during the prosecution of Applicant's PCT/IL2011/000446.
An International Search Report with Written Opinion both dated Feb. 2, 2012, which issued during the prosecution of Applicant's PCT/IL2011/000600.
An International Preliminary Report on Patentability dated Nov. 9, 2011 which issued during the prosecution of Applicant's PCT/IL2010/000358.
An Office Action dated Aug. 4, 2010, which issued during the prosecution of U.S. Appl. No. 12/341,960.
An Office Action dated Nov. 14, 2011, which issued during the prosecution of U.S. Appl. No. 12/608,316.
An Office Action dated Aug. 15, 2013, which issued during the prosecution of U.S. Appl. No. 12/795,192.
An Office Action dated Jan. 17, 2013, which issued during the prosecution of U.S. Appl. No. 12/795,192.
An Office Action dated Feb. 12, 2013, which issued during the prosecution of U.S. Appl. No. 12/926,673.
Notice of Allowance dated Dec. 7, 2011, which issued during the prosecution of U.S. Appl. No. 12/435,291.
A Restriction Requirement dated Oct. 27, 2011, which issued during the prosecution of U.S. Appl. No. 12/563,952.
A Notice of Allowance dated May 24, 2012, which issued during the prosecution of U.S. Appl. No. 12/563,952.
A Restriction Requirement dated Jul. 5, 2012, which issued during the prosecution of U.S. Appl. No. 12/563,930.
A Notice of Allowance dated Apr. 3, 2013, which issued during the prosecution of U.S. Appl. No. 12/563,930.
An Office Action dated Apr. 2, 2013, which issued during the prosecution of U.S. Appl. No. 12/785,717.
An Advisory Action dated Sep. 6, 2012 which issued during the prosecution of U.S. Appl. No. 12/548,991.
A Restriction Requirement dated Feb. 4, 2013 which issued during the prosecution of U.S. Appl. No. 13/141,606.
An Office Action dated Feb. 14, 2013 which issued during the prosecution of U.S. Appl. No. 13/167,492.
An International Search Report and a Written Opinion both dated Feb. 22, 2013, which issued during the prosecution of Applicant's PCT/IL201/050451.
An Office Action dated Apr. 1, 2013 which issued during the prosecution of U.S. Appl. No. 13/167,476.
A Restriction Requirement dated Jun. 7, 2013 which issued during the prosecution of U.S. Appl. No. 13/141,606.
An Office Action dated Aug. 23, 2013 which issued during the prosecution of U.S. Appl. No. 13/167,444.
U.S. Appl. No. 61/265,936, filed Dec. 2, 2009.
U.S. Appl. No. 61/283,445, filed Dec. 2, 2009.
U.S. Appl. No. 61/207,908, filed Feb. 17, 2009.
Amplatzer Cardiac Plug brochure (English pages), AGA Medical Corporation (Plymouth, MN) (copyright 2008-2010, downloaded Jan. 11, 2011).
An Office Action dated Dec. 16, 2013, which issued during the prosecution of U.S. Appl. No. 13/666,262.
Notice of Allowance dated Nov. 19, 2013, which issued during the prosecution of U.S. Appl. No. 12/795,192.
An Office Action dated Oct. 2, 2013, which issued during the prosecution of U.S. Appl. No. 13/167,492.
An Office Action dated Nov. 21, 2013, which issued during the prosecution of U.S. Appl. No. 13/167,476.
An Office Action dated Dec. 18, 2013, which issued during the prosecution of U.S. Appl. No. 13/666,141.
A Restriction Requirement dated Apr. 19, 2010 which issued during the prosecution of U.S. Appl. No. 12/341,960.
An Office Action dated Jun. 13, 2012, which issued during the prosecution of U.S. Appl. No. 12/437,103.
An Office Action dated Nov. 30, 2012, which issued during the prosecution of U.S. Appl. No. 12/689,635.
An Office Action dated Oct. 22, 2013, which issued during the prosecution of U.S. Appl. No. 12/926,673.
A Restriction Requirement dated Oct. 25, 2012 which issued during the prosecution of U.S. Appl. No. 13/167,444.
An Office Action dated Jan. 17, 2013, which issued during the prosecution of U.S. Appl. No. 13/167,444.
A Restriction Requirement dated Nov. 2, 2012, which issued during the prosecution of U.S. Appl. No. 13/167,492.
An International Preliminary Report on Patentability dated Feb. 4, 2014, which issued during the prosecution of Applicant's PCT/IL2011/000446.
A Supplementary European Search Report dated Dec. 4, 2012, which issued during the prosecution of European Patent Application No. EP 09834225.6.
A Supplementary European Search Report dated Mar. 28, 2013, which issued during the prosecution of European Patent Application No. EP 1077 2091.4.
U.S. Appl. No. 61/733,979, filed Dec. 6, 2012.
U.S. Appl. No. 61/717,303, filed Oct. 23, 2012.
U.S. Appl. No. 61/820,979, filed May 8, 2013.
U.S. Appl. No. 61/745,848, filed Dec. 6, 2012.
An Office Action dated May 19, 2011, which issued during the prosecution of U.S. Appl. No. 12/706,868.
An Office Action dated Sep. 1, 2011, which issued during the prosecution of U.S. Appl. No. 12/706,868.
An Office Action dated Dec. 27, 2013, which issued during the prosecution of U.S. Appl. No. 12/785,717.
An Office Action dated May 30, 2012, which issued during the prosecution of U.S. Appl. No. 12/706,868.
Amendment, Terminal Disclaimer and Extension dated Jun. 27, 2012, which issued during the prosecution of U.S. Appl. No. 12/548,991.
An International Preliminary Report on Patentability dated Jan. 29, 2013, which issued during the prosecution of Applicant's PCT/IL2011/000600.
An International Search Report and a Written Opinion both dated Dec. 6, 2012 which issued during the prosecution of Applicant's PCT/IL2012/000250.
An Office Action dated Jun. 18, 2015, which issued during the prosecution of U.S. Appl. No. 14/551,951.
U.S. Appl. No. 61/557,082, filed Nov. 8, 2011.
A Restriction Requirement dated Jul. 12, 2011, which issued during the prosecution of U.S. Appl. No. 12/437,103.
An Office Action dated Mar. 27, 2013, which issued during the prosecution of U.S. Appl. No. 12/843,412.
An Office Action dated May 6, 2013, which issued during the prosecution of U.S. Appl. No. 12/689,693.
A Restriction Requirement dated May 1, 2012, which issued during the prosecution of U.S. Appl. No. 12/843,412.
Langer et al. Ring plus String: Papillary muscle repositioning as an adjunctive repair technique for ischemic mitral regurgitation, The Journal of Thoracic Cardiovascular surgery vol. 133 No. 1, Jan. 2007.
Langer et al. RING+STRING, Successful Repair technique for ischemic mitral regurgitation with severe leaflet Tethering, The Department of Thoracic Cardiovascular surgery, Hamburg, Germany, Nov. 2008.
U.S. Appl. No. 61/555,570, filed Nov. 4, 2011.
A Notice of Allowance dated Sep. 18, 2012, which issued during the prosecution of U.S. Appl. No. 12/706,868.
An Office Action dated Aug. 13, 2012, which issued during the prosecution of U.S. Appl. No. 13/044,694.

(56) References Cited

OTHER PUBLICATIONS

An Office Action dated Dec. 31, 2012, which issued during the prosecution of U.S. Appl. No. 13/044,694.
A Restriction Requirement dated Apr. 1, 2011, which issued during the prosecution of U.S. Appl. No. 12/608,316.
Agarwal et al. International Cardiology Perspective Functional Tricuspid Regurgitation, Circ Cardiovasc Interv 2009;2;2;565-573 (2009).
An Office Action dated Oct. 6, 2010, which issued during the prosecution of Applicant's U.S. Appl. No. 12/484,512.
An Office Action dated Jul. 6, 2012, which issued during the prosecution of U.S. Appl. No. 12/692,061.
An Interview Summary dated Jul. 27, 2011, which issued during the prosecution of U.S. Appl. No. 12/341,960.
A Notice of Allowance dated May 2, 2013, which issued during the prosecution of U.S. Appl. No. 12/843,412.
An Office Action dated Jul. 18, 2013, which issued during the prosecution of U.S. Appl. No. 13/044,694.
Search Report in European Patent Application 10772090.6 dated Jan. 17, 2014.
An Office Action dated Feb. 3, 2014, which issued during the prosecution of U.S. Appl. No. 12/689,693.
Communication regarding amended claims filed dated Dec. 27, 2012, regarding European App No. 11792047.0.
Notice of Allowance dated Mar. 6, 2014, which issued during the prosecution of U.S. Appl. No. 12/437,103.
An Office Action dated Oct. 9, 2013, which issued during the prosecution of U.S. Appl. No. 12/966,954.
AMPLATZER® Septal Occluder. A patient guide to the Non-Surgical Closuer of the Atrial Septal Defect Using the AMPLATZER Septal Occluder System, AGA Medical Corporation, Apr. 2008.
Notice of Allowance dated Sep. 12, 2014, which issued during the prosecution of U.S. Appl. No. 11/950,930.
An Office Action dated Dec. 19, 2013, which issued during the prosecution of U.S. Appl. No. 14/027,934.
An International Preliminary Report on Patentability dated Dec. 18, 2010, which issued during the prosecution of Applicant's PCT/IL09/00593.
An English translation of an Office Action dated Apr. 23, 2014 which issued during the prosecution of Chinese Patent Application No. 201080059948.4.
Notice of Allowance dated Jun. 23, 2014, which issued during the prosecution of U.S. Appl. No. 12/548,991.
Notice of Allowance dated Jun. 11, 2014, which issued during the prosecution of U.S. Appl. No. 12/689,693.
Notice of Allowance dated Jun. 25, 2014, which issued during the prosecution of U.S. Appl. No. 13/666,262.
An International Search Report and Written Opinion both dated Apr. 9, 2014, which issued during the prosecution of Applicant's PCT/IL13/50860.
An International Search Report & Written Opinion both dated May 12, 2015, which issued during the prosecution of Applicant's PCT/IL2014/050914.
An Office Action dated Jun. 11, 2014, which issued during the prosecution of U.S. Appl. No. 14/027,934.
A Restriction Requirement dated Jun. 2, 2014, which issued during the prosecution of U.S. Appl. No. 13/319,030.
Brennan, Jennifer, 510(k) Summary of safety and effectiveness, Jan. 2008.
A communication from the European Patent Office dated Sep. 28, 2011 which issued during the prosecution of European Application No. 09834225.6.
A Restriction Requirement dated Sep. 17, 2012, which issued during the prosecution of U.S. Appl. No. 12/689,693.
An Office Action dated Aug. 22, 2014, which issued during the prosecution of U.S. Appl. No. 14/027,934.
An Office Action dated Aug. 26, 2014, which issued during the prosecution of U.S. Appl. No. 13/167,444.

Communication dated Jul. 25, 2014, issued by the State Intellectual Property Office of the P.R. of China in counterpart Application No. 200980157331.3.
A Notice of Allowance dated Sep. 3, 2014, which issued during the prosecution of U.S. Appl. No. 12/689,693.
Communication from the European Patent Office dated Jun. 11, 2015, which issued during the prosecution of European Patent Application No. 11811934.
Supplementary European Search Report dated Oct. 23, 2014 which issued during the prosecution of Applicant's European App No. 10826224.7.
An International Search Report & Written Opinion both dated Mar. 21, 2014, which issued during the prosecution of Applicant's PCT/IL13/50992.
A Notice of Allowance dated Feb. 2, 2015, which issued during the prosecution of U.S. Appl. No. 13/504,870.
An Office Action dated Oct. 14, 2014, which issued during the prosecution of U.S. Appl. No. 13/319,030.
Alfieri et al., "The edge to edge technique," The European Association for Cardio-Thoracic Surgery 14$^{th}$ Annual Meeting Oct. 7-11, Book of Procees. (2000).
An Office Action dated Sep. 29, 2014, which issued during the prosecution of U.S. Appl. No. 13/504,870.
An Office Action dated Oct. 3, 2014, which issued during the prosecution of U.S. Appl. No. 13/749,153.
An International Search Report & Written Opinion both dated Sep. 8, 2009, which issued during the prosecution of Applicant's PCT/IL09/00593.
An International Search Report and a Written Opinion both dated Nov. 14, 2011, which issued during the prosecution of Applicant's PCT/IL2011/000404.
Dictionary.com definition of "lock", Jul. 29, 2013.
A Restriction Requirement dated Jan. 6, 2012, which issued during the prosecution of U.S. Appl. No. 12/795,026.
A Restriction Requirement dated Nov. 14, 2011 which issued during the prosecution of U.S. Appl. No. 12/548,991.
An International Preliminary Report on Patentability dated Apr. 28, 2015, which issued during the prosecution of Applicant's PCT/IL2013/050861.
A Notice of Allowance dated May 22, 2013, which issued during the prosecution of U.S. Appl. No. 12/689,635.
An International Preliminary Report on Patentability dated May 1, 2012, which issued during the prosecution of Applicant's PCT/IL2010/000890.
A Notice of Allowance dated Jan. 7, 2014, which issued during the prosecution of U.S. Appl. No. 12/926,673.
Restriction Requirement dated May 5, 2011, which issued during the prosecution of U.S. Appl. No. 12/706,868.
Supplementary European Search Report dated Aug. 4, 2014 which issued during the prosecution of Applicant's European App No. 11 81 1934.6.
An Office Action dated Aug. 5, 2010 which issued during the prosecution of U.S. Appl. No. 11/950,930.
An Office Action dated Feb. 17, 2010 which issued during the prosecution of U.S. Appl. No. 11/950,930.
Restriction Requirement dated Nov. 14, 2011, which issued during the prosecution of U.S. Appl. No. 12/689,635.
Supplementary European Search Report dated Jan. 21, 2014 which issued during the prosecution of Applicant's European App No. 11 78 6226.
An Office Action dated Jun. 4, 2014, which issued during the prosecution of U.S. Appl. No. 12/840,463.
Maisano, The double-orifice technique as a standardized approach to treat mitral . . . , European Journal of Cardio-thoracic Surgery 17 (2000) 201-205.
AMPLATZER® Cribriform Occluder. A patient guide to Percutaneous, Transcatheter, Atrial Septal Defect Closuer, AGA Medical Corporation, Apr. 2008.
An Office Action dated Jun. 10, 2014, which issued during the prosecution of U.S. Appl. No. 13/167,492.
An Office Action dated May 28, 2015, which issued during the prosecution of U.S. Appl. No. 14/128,756.

(56) References Cited

OTHER PUBLICATIONS

An Office Action dated Apr. 2, 2015, which issued during the prosecution of U.S. Appl. No. 14/027,934.
An Office Action dated Mar. 23, 2015, which issued during the prosecution of U.S. Appl. No. 13/707,013.
Supplementary European Search Report dated Dec. 23, 2014 which issued during the Applicant's European App No. 10834311.
An Office Action dated Mar. 24, 2015, which issued during the prosecution of U.S. Appl. No. 12/996,954.
An Office Action dated Mar. 23, 2015, which issued during the prosecution of European Patent Application No. EP 09834225.6.
Supplementary European Search Report dated Mar. 23, 2015, which issued during the prosecution of Applicant's European App No. 11792047.0.
Notice of Allowance dated Dec. 20, 2013, which issued during the prosecution of U.S. Appl. No. 12/437,103.
Supplementary European Search Report dated Apr. 29, 2015, which issued during the prosecution of Applicant's European App No. 14200202.
An International Preliminary Report on Patentability dated Dec. 23, 2014, which issued during the prosecution of Applicant's PCT/IL2012/050451.
An International Search Report and a Written Opinion both dated Apr. 15, 2014, which issued during the prosecution of Applicant's PCT/IL2013/050861.
An International Preliminary Report on Patentability dated Dec. 23, 2013, which issued during the prosecution of Applicant's PCT/IL2012/000250.
An Office Action dated Aug. 7, 2015, which issued during the prosecution of U.S. Appl. No. 14/128,756.
An Invitation to pay additional fees dated Jan. 31, 2014, which issued during the prosecution of Applicant's PCT/IL2013/050861.
An Invitation to pay additional fees dated Jan. 31, 2014, which issued during the prosecution of Applicant's PCT/IL2013/050860.
An Office Action dated Sep. 19, 2014, which issued during the prosecution of U.S. Appl. No. 13/044,694.
A communication from the European Patent Office dated Oct. 19, 2012 which issued during the prosecution of European Application No. 11792047.0.
An Office Action dated Oct. 5, 2012, which issued during the prosecution of U.S. Appl. No. 12/996,954.
An Office Action dated Oct. 5, 2015, which issued during the prosecution of U.S. Appl. No. 14/246,417.
An Office Action dated Oct. 1, 2015, which issued during the prosecution of U.S. Appl. No. 14/141,228.
Supplementary European Search Report dated Sep. 25, 2015, which issued during the prosecution of Applicant's European App No. 09794095.1.
An Office Action dated Apr. 7, 2015, which issued during the prosecution of U.S. Appl. No. 13/319,007.
An Office Action dated Jan. 13, 2015, which issued during the prosecution of U.S. Appl. No. 13/707,013.
An Office Action dated Jan. 5, 2016, which issued during the prosecution of U.S. Appl. No. 14/027,934.
An Office Action dated Mar. 16, 2015, which issued during the prosecution of U.S. Appl. No. 14/084,426.
European Search Report dated Jun. 24, 2016, which issued during the prosecution of European Patent Application No. EP 12847363.
An Office Action dated Mar. 24, 2015, which issued during the prosecution of U.S. Appl. No. 14/486,226.
An Office Action dated Jul. 20, 2016, which issued during the prosecution of U.S. Appl. No. 14/246,417.
Notice of Allowance dated May 22, 2015, which issued during the prosecution of U.S. Appl. No. 13/749,153.
An Office Action dated Jun. 18, 2015, which issued during the prosecution of U.S. Appl. No. 13/319,030.
An Office Action dated Jun. 13, 2014, which issued during the prosecution of U.S. Appl. No. 13/141,606.
An English translation of an Office Action dated Jul. 17, 2015 which issued during the prosecution of Chinese Patent Application No. 201080059948.4.
Notice of Allowance dated Sep. 29, 2014, which issued during the prosecution of U.S. Appl. No. 13/141,606.
An International Search Report and a Written Opinion both dated Oct. 27, 2016, which issued during the prosecution of Applicant's PCT/IL2015/050792.
An International Preliminary Report on Patentability dated Jun. 9, 2015, which issued during the prosecution of Applicant's PCT/IL2013/050992.
An Office Action dated May 3, 2016, which issued during the prosecution of U.S. Appl. No. 13/319,030.
A Notice of Allowance dated Sep. 2, 2016, which issued during the prosecution of U.S. Appl. No. 14/027,934.
An Office Action dated Feb. 3, 2015, which issued during the prosecution of U.S. Appl. No. 14/084,426.
Search Report in European Patent Application 10826224.7 dated Nov. 16, 2015.
Notice of Allowance dated Dec. 24, 2014, which issued during the prosecution of U.S. Appl. No. 12/795,026.
An English Translation of an Office Action dated Nov. 24, 2015, which issued during the prosecution of Israel Patent Application No. 223448. (the relevant part only).
Notice of Allowance dated Nov. 12, 2015, which issued during the prosecution of U.S. Appl. No. 13/319,007.
Notice of Allowance dated Jan. 7, 2016, which issued during the prosecution of U.S. Appl. No. 13/319,007.
Notice of Allowance dated Apr. 20, 2011, which issued during the prosecution of U.S. Appl. No. 12/484,512.
Notice of Allowance dated Mar. 23, 2011, which issued during the prosecution of U.S. Appl. No. 12/484,512.
An Office Action dated May 23, 2016, which issued during the prosecution of U.S. Appl. No. 14/209,171.
European Search Report dated Jul. 8, 2016, which issued during the prosecution of Applicant's No. 13849843.1.
Notice of Allowance dated Nov. 13, 2014, which issued during the prosecution of U.S. Appl. No. 12/795,026.
Notice of Allowance dated Feb. 19, 2014, which issued during the prosecution of U.S. Appl. No. 12/795,192.
Notice of Allowance dated Nov. 23, 2016, which issued during the prosecution of U.S. Appl. No. 14/141,228.
An English translation of an Office Action dated Dec. 12, 2013 which issued during the prosecution of Chinese Patent Application No. 200980157331.3.
Notice of Allowance dated Nov. 17, 2015, which issued during the prosecution of U.S. Appl. No. 14/486,226.
European Search Report dated Nov. 4, 2015, which issued during the prosecution of European Patent Application No. EP 1077 2091.4.
Notice of Allowance dated Dec. 19, 2016, which issued during the prosecution of U.S. Appl. No. 14/242,151.
European Search Report dated Jul. 15, 2016, which issued during the prosecution of Applicant's European App No. 13849947.0.
An Office Action dated Jun. 17, 2016, which issued during the prosecution of U.S. Appl. No. 14/357,040.
Notice of Allowance dated Dec. 30, 2016, which issued during the prosecution of U.S. Appl. No. 13/319,030.
Notice of Allowance dated Mar. 25, 2015, which issued during the prosecution of U.S. Appl. No. 13/749,153.
Notice of Allowance dated Aug. 3, 2015, which issued during the prosecution of U.S. Appl. No. 13/749,153.
Notice of Allowance dated Dec. 9, 2014, which issued during the prosecution of U.S. Appl. No. 13/167,476.
Notice of Allowance dated Nov. 7, 2014, which issued during the prosecution of U.S. Appl. No. 13/167,492.
Notice of Allowance dated Jan. 22, 2015, which issued during the prosecution of U.S. Appl. No. 13/167,444.
An International Preliminary Report on Patentability dated Apr. 28. 2015, which issued during the prosecution of Applicant's PCT/IL2013/050860.
An Office Action dated Jan. 6, 2016, which issued during the prosecution of U.S. Appl. No. 14/128,756.

(56) References Cited

OTHER PUBLICATIONS

An Office Action dated Apr. 8, 2016, which issued during the prosecution of U.S. Appl. No. 14/141,228.
An Office Action dated Apr. 7, 2016, which issued during the prosecution of U.S. Appl. No. 14/242,151.
An Office Action dated Jan. 4, 2016, which issued during the prosecution of U.S. Appl. No. 14/589,100.
An International Preliminary Report on Patentability dated Jun. 10, 2009, which issued during the prosecution of Applicant's PCT/IL07/01503.
Notice of Allowance dated Aug. 19, 2013, which issued during the prosecution of U.S. Appl. No. 11/908,906.
An Office Action dated Jun. 8, 2012, which issued during the prosecution of U.S. Appl. No. 11/908,906.
An Office Action dated Dec. 21, 2013, which issued during the prosecution of U.S. Appl. No. 11/908,906.
A Restriction Requirement dated Aug. 5, 2011, which issued during the prosecution of U.S. Appl. No. 11/908,906.
An Office Action dated Oct. 23, 2012, which issued during the prosecution of Japanese Patent Application No. 2009-539871.
U.S. Appl. No. 60/662,616, filed Mar. 17, 2005.
U.S. Appl. No. 60/700,542, filed Jul. 18, 2005.
An Office Action dated May 4, 2016, which issued during the prosecution of U.S. Appl. No. 14/589,100.
An Office Action dated Jun. 14, 2016, which issued during the prosecution of U.S. Appl. No. 14/273,155.
An International Search Report and a Written Opinion both dated Jan. 25, 2016, which issued during the prosecution of Applicant's PCT/IL2015/051027.
An Office Action dated Jan. 5, 2016, which issued during the prosecution of U.S. Appl. No. 14/084,426.
An International Preliminary Report on Patentability dated Apr. 26, 2016, which issued during the prosecution of Applicant's PCT/IL2014/050914.
An Office Action dated May 11, 2016, which issued during the prosecution of U.S. Appl. No. 14/128,756.
An International Search Report and a Written Opinion both dated Sep. 12, 2008, which issued during the prosecution of Applicant's PCT/IL07/01503.
An English Translation of an Office Action dated Sep. 15, 2016, which issued during the prosecution of Israel Patent Application No. 243837. (the relevant part only).
Notice of Allowance dated Sep. 14, 2015, which issued during the prosecution of U.S. Appl. No. 13/707,013.
Notice of Allowance dated Jul. 24, 2015, which issued during the prosecution of U.S. Appl. No. 13/707,013.
Notice of Allowance dated Jul. 8, 2015, which issued during the prosecution of U.S. Appl. No. 13/707,013.
Ahmadi, Ali, et al. "Percutaneously adjustable pulmonary artery band." *The Annals of thoracic surgery* 60 (1995): S520-S522.
Assad, Renato S. "Adjustable Pulmonary Artery Banding." (2014).
Ahmadi, A., G. Spillner, and Th Johannesson. "Hemodynamic changes following experimental production and correction of acute mitral regurgitation with an adjustable ring prosthesis." *The Thoracic and cardiovascular surgeon* 36.06 (1988): 313-319.
Swenson, Orvar. "Internal device for control of urinary incontinence." *Journal of pediatric surgery* 7.5 (1972): 542-545.
Park, Sang C., et al. "A percutaneously adjustable device for banding of the pulmonary trunk." *International journal of cardiology* 9.4 (1985): 477-484.
Elliott, Daniel S., Gerald W. Timm, and David M. Barrett. "An implantable mechanical urinary sphincter: a new nonhydraulic design concept." *Urology* 52.6 (1998): 1151-1154.
An Invitation to pay additional fees dated Aug. 18, 2016, which issued during the prosecution of Applicant's PCT/IL2016/050433.
Daebritz, S., et al. "Experience with an adjustable pulmonary artery banding device in two cases: initial success-midterm failure." *The Thoracic and cardiovascular surgeon* 47.01 (1999): 51-52.
Notice of Allowance dated Mar. 1, 2017, which issued during the prosecution of U.S. Appl. No. 14/357,040.

An Office Action dated Sep. 6, 2016, which issued during the prosecution of U.S. Appl. No. 14/141,228.
An International Search Report and a Written Opinion both dated Oct. 17, 2016, which issued during the prosecution of Applicant's PCT/IL2016/050433.
An Office Action dated Oct. 21, 2016, which issued during the prosecution of U.S. Appl. No. 14/567,472.
Notice of Allowance dated Jul. 7, 2015, which issued during the prosecution of U.S. Appl. No. 12/996,954.
Notice of Allowance dated Nov. 18, 2016, which issued during the prosecution of U.S. Appl. No. 13/740,582.
Notice of Allowance dated Oct. 20, 2015, which issued during the prosecution of U.S. Appl. No. 12/996,954.
Amendment and Extension dated Apr. 11, 2012, which issued during the prosecution of U.S. Appl. No. 12/563,952.
Notice of Allowance dated Dec. 8, 2016, which issued during the prosecution of U.S. Appl. No. 14/246,417.
Notice of Allowance dated Dec. 21, 2016, which issued during the prosecution of U.S. Appl. No. 14/246,417.
Notice of Allowance dated Dec. 29, 2016, which issued during the prosecution of U.S. Appl. No. 14/246,417.
Notice of Allowance dated Jan. 3, 2017, which issued during the prosecution of U.S. Appl. No. 14/128,756.
Swenson, O. and Malinin, T.I., 1978. An improved mechanical device for control of urinary incontinence. *Investigative urology*, 15(5), pp. 389-391.
Swenson, O. An experimental implantable urinary sphincter. *Invest Urol*. Sep. 1976;14(2):100-3.
An International Preliminary Report on Patentability dated Sep. 18, 2007, which issued during the prosecution of Applicant's PCT/IL2006/000342.
An International Search Report and a Written Opinion both dated May 30, 2007, which issued during the prosecution of Applicant's PCT/IL2006/000342.
An Advisory Action dated Feb. 4, 2014, which issued during the prosecution of U.S. Appl. No. 13/167,476.
An English Translation of an Office Action dated May 31, 2012, which issued during the prosecution of Israel Patent Application No. 209946. (the relevant part only).
A Restriction Requirement dated Jul. 8, 2015, which issued during the prosecution of U.S. Appl. No. 14/141,228.
Notice of Allowance dated Sep. 22, 2016, which issued during the prosecution of U.S. Appl. No. 13/740,582.
A Restriction Requirement dated Sep. 4, 2015, which issued during the prosecution of U.S. Appl. No. 14/589,100.
Notice of Allowance dated Jan. 29, 2016, which issued during the prosecution of U.S. Appl. No. 14/551,951.
An International Search Report and a Written Opinion both dated May 28, 2014, which issued during the prosecution of Applicant's PCT/IL14/050027.
An Office Action dated Aug. 22, 2016, which issued during the prosecution of U.S. Appl. No. 14/084,426.
An Office Action dated Dec. 20, 2016, which issued during the prosecution of UK Patent Application No. 1611910.9.
Notice of Allowance dated Aug. 7, 2015, which issued during the prosecution of Chinese Patent Application No. 200980157331.3.
An Office Action dated Jan. 20, 2017, which issued during the prosecution of U.S. Appl. No. 14/650,114.
An Office Action dated Feb. 10, 2017, which issued during the prosecution of U.S. Appl. No. 14/990,172.
An Office Action dated Feb. 2, 2017, which issued during the prosecution of U.S. Appl. No. 14/209,171.
An Office Action dated Jan. 25, 2017, which issued during the prosecution of Chinese Patent Application No. 201510681407.X.
An Office Action dated Dec. 13, 2016, which issued during the prosecution of Applicant's European App No. 11786226.8.
An Interview Summary dated Apr. 4, 2012, which issued during the prosecution of U.S. Appl. No. 12/563,952.
An Office Action dated Mar. 3, 2017, which issued during the prosecution of Applicant's European App No. 11792047.0.

(56) References Cited

OTHER PUBLICATIONS

An Office Action dated Feb. 27, 2017, which issued during the prosecution of U.S. Appl. No. 15/249,957.

* cited by examiner

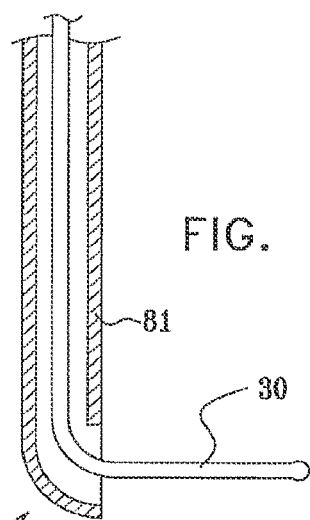
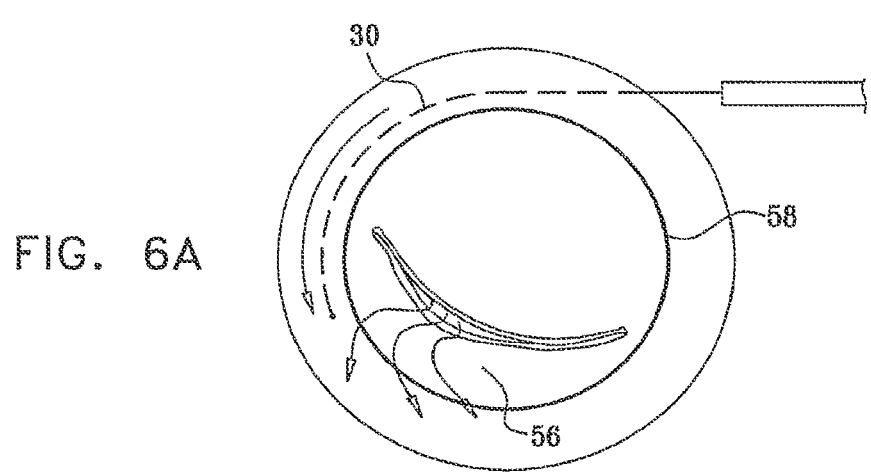
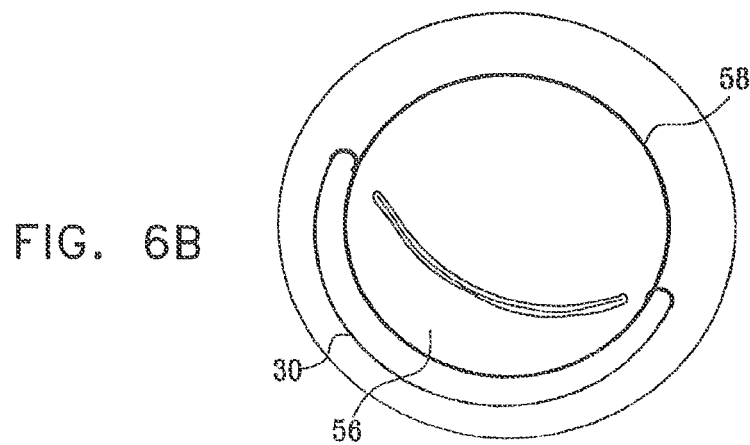

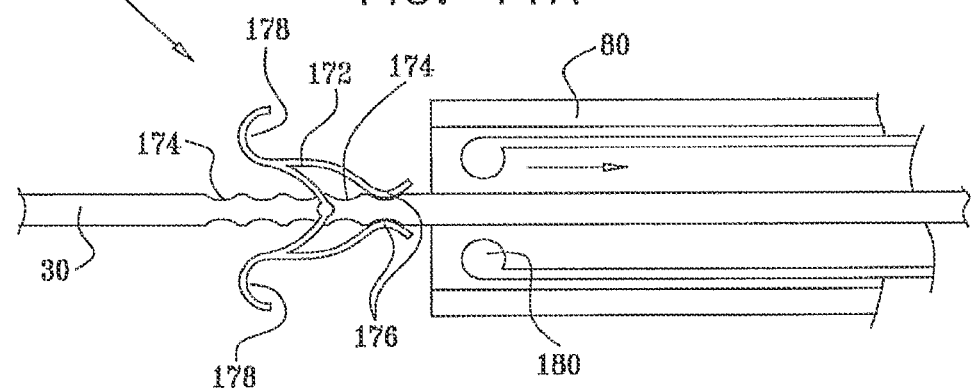
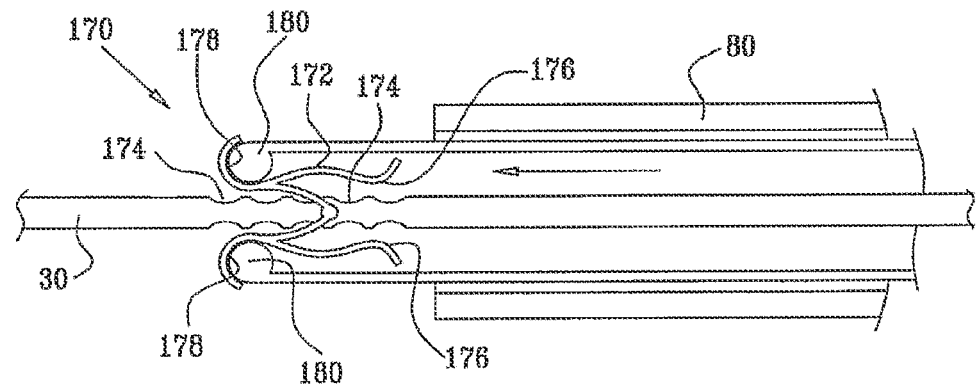

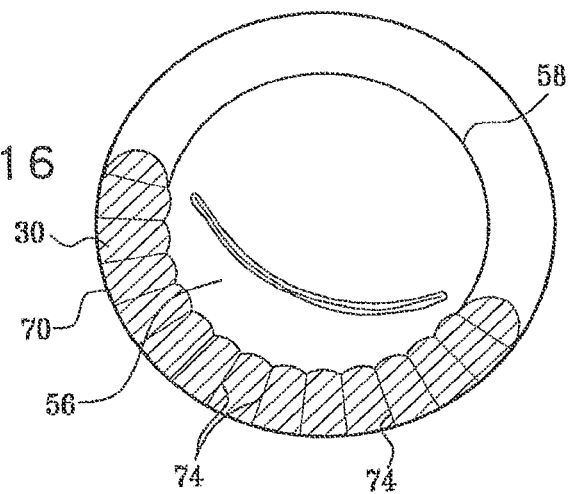
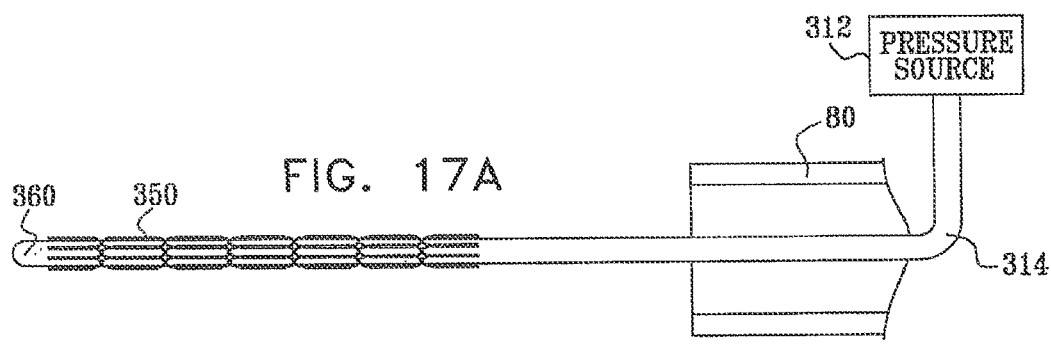
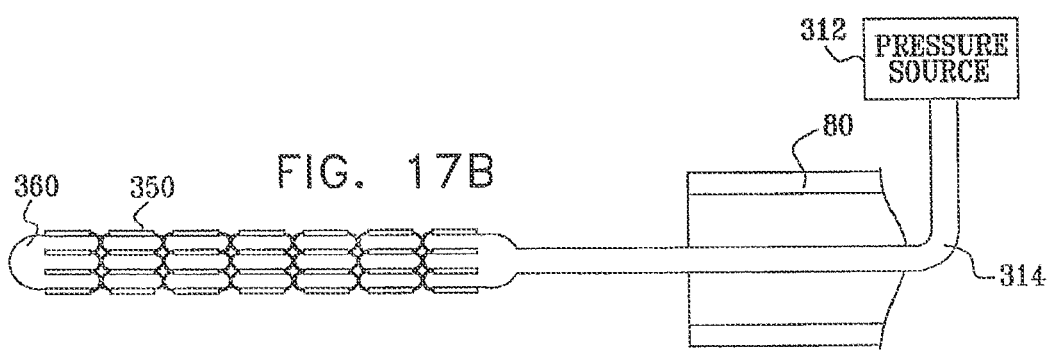

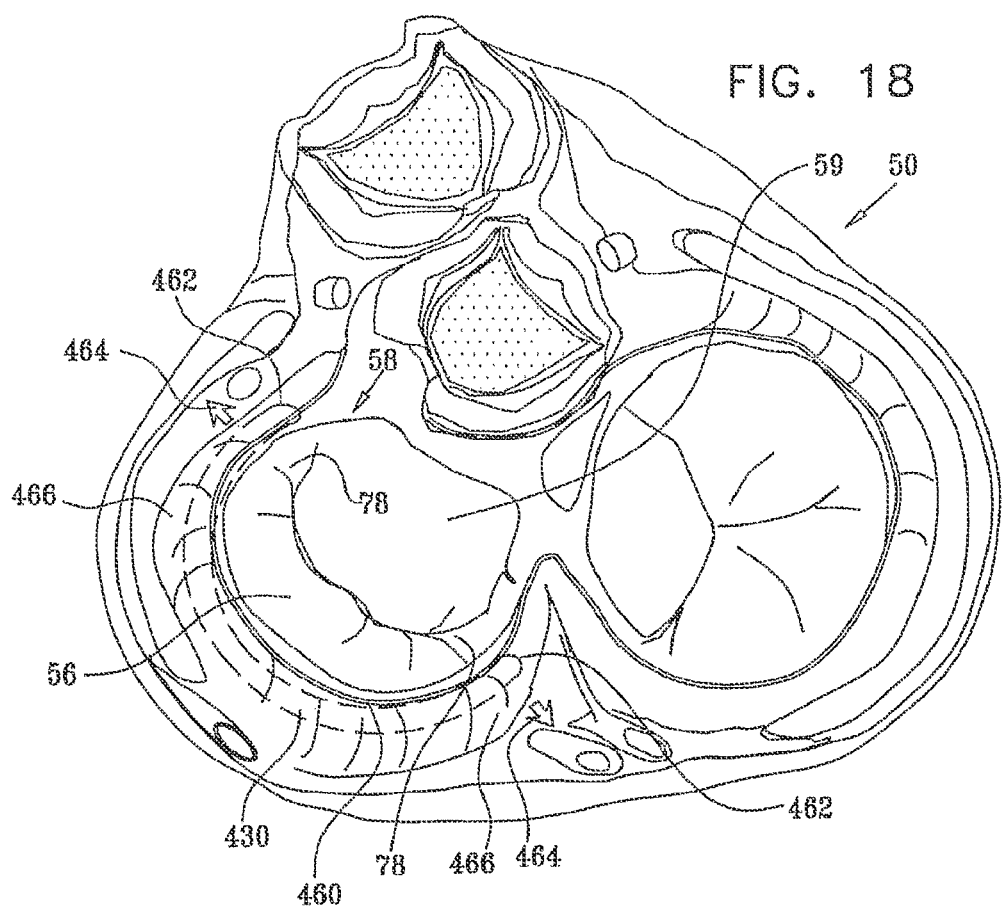

MITRAL VALVE TREATMENT TECHNIQUES

CROSS-REFERENCES TO RELATED APPLICATIONS

The present application is a continuation application of U.S. Ser. No. 14/084,426 to Gross et al., entitled, "Mitral valve treatment techniques," filed on Nov. 19, 2013, which published as US 2014/0148898, and which is a divisional application of U.S. Ser. No. 11/908,906 to Gross et al., entitled, "Mitral valve treatment techniques," filed on Dec. 8, 2008, now U.S. Pat. No. 8,608,797, which is the US national phase application of PCT/IL2006/000342 filed on Mar. 15, 2006, which published as WO 2006/097931, and which claims the benefit of:

(a) U.S. Provisional Patent Application 60/662,616 to Gross et al., filed Mar. 17, 2005, and (b) U.S. Provisional Patent Application 60/700,542 to Gross et al., filed Jul. 18, 2005.

All of these applications are assigned to the assignee of the present application and are incorporated herein by reference.

FIELD OF THE INVENTION

The present invention relates generally to surgical methods and apparatus, and specifically to methods and apparatus for mitral valve treatment.

BACKGROUND OF THE INVENTION

Mitral valve regurgitation is a disorder in which the mitral valve does not close properly. During systole, a healthy mitral valve prevents oxygenated blood from flowing back (regurgitating) from the left ventricle to the left atrium. Regurgitation caused by a defective mitral valve reduces cardiac output, increasing the risk of progressive heart failure. Treatments for mitral valve regurgitation include valve replacement and strengthening the valve annulus by implanting a mechanical support ring or other structure (generally called valve annuloplasty).

The chordae tendineae are commonly classified according to their insertion sites on the mitral cusps. The first-order (also called primary or marginal) chordae insert on the cusp free edges, the second-order (also called "strut") chordae insert on the ventricular surface of the cusps, usually near the junction between the rough and smooth zones, and the third-order (also called tertiary or basal) chordae originate directly from the trabeculae carneae of the left ventricular wall, and attach to the cusps near the annulus of the mitral valve.

US Patent Application Publication 2005/0010287 to Macoviak et al., which is incorporated herein by reference, describes techniques for supplementing, repairing, or replacing a native heart valve. The techniques employ an implant that is adapted to extend adjacent a valve annulus. The implant includes a mobile neoleaflet element that occupies the space of at least a portion of one native valve leaflet. The implant mimics the one-way valve function of a native leaflet, to resist or prevent retrograde flow. The implant restores normal coaptation of the leaflets to resist retrograde flow, thereby resisting eversion and/or prolapse, which, in turn, reduces regurgitation.

US Patent Application Publication 2004/0193191 to Starksen et al., which is incorporated herein by reference, describes methods for treating a cardiac valve annulus, comprising contacting an anchor delivery device with the valve annulus and releasing a plurality of coupled anchors from the anchor delivery device to secure the anchors to the annulus. Anchors, which in some embodiments are superelastic or shape memory self-securing anchors, are then drawn together to tighten the annulus. The publication also describes devices including an elongate catheter having a housing at or near the distal end for releasably housing a plurality of coupled anchors. The housing may be flexible, may conform to a valve annulus, and in some embodiments may be coupled with an expandable member to enhance contact of the housing with annular tissue. In one embodiment, self-securing anchors lie approximately flat within the delivery device housing, allowing anchors with relatively large deployed shapes to be housed in and deployed from a relatively narrow delivery device.

US Patent Application Publication 2004/0148020 to Vidlund et al., which is incorporated herein by reference, describes techniques for improving the function of a valve (e.g., a mitral valve) by positioning an implantable device outside and adjacent the heart wall such that the device alters the shape of the heart wall acting on the valve. The implantable device may alter the shape of the heart wall acting on the valve by applying an inward force and/or by circumferential shortening (cinching). The shape change of the heart wall acting on the valve is sufficient to change the function of the valve, and may increase coaptation of the leaflets, for example, to reduce regurgitation.

US Patent Application Publication 2004/0148019 to Vidlund et al., which is incorporated herein by reference, describes techniques for improving the function of a valve (e.g., a mitral valve) by positioning a spacing filling device outside and adjacent the heart wall such that the device applies an inward force against the heart wall acting on the valve. A substantially equal and opposite force may be provided by securing the device to the heart wall, and/or a substantially equal and opposite outward force may be applied against anatomical structure outside the heart wall. The inward force is sufficient to change the function of the valve, and may increase coaptation of the leaflets, for example. The space filling device may be implanted by a surgical approach, a transthoracic approach, or a transluminal approach, for example. The space filling portion may be delivered utilizing a delivery catheter navigated via the selected approach, and the space filling portion may be expandable between a smaller delivery configuration and a larger deployed configuration.

US Patent Application Publication 2004/0138745 to Macoviak et al., which is incorporated herein by reference, describes medical devices for improving heart valve function, including leaflet retainers, a neo-annulus, neo-leaflet, and a framework.

US Patent Application Publication 2004/0127983 to Mortier et al., which is incorporated herein by reference, describes a device for heart valve repair including at least one tension member having a first end and second end. A basal anchor is disposed at the first end of the tension member and a secondary anchor at the second end. The publication describes a method including the steps of anchoring the basal anchor proximate a heart valve and anchoring the secondary anchor at a location spaced from the valve such that the chamber geometry is altered to reduce heart wall tension and/or stress on the valve leaflets.

U.S. Pat. No. 6,629,534 and US Patent Application Publication 2004/0039442 to St. Goar et al., which are incorporated herein by reference, describe techniques for performing endovascular repair of atrioventricular and other cardiac valves in the heart. Regurgitation of an atrioventricular valve, particularly a mitral valve, is repaired by modifying a tissue structure selected from the valve leaflets, the valve annulus, the valve chordae, and the papillary muscles. These structures are modified by suturing, stapling, snaring, or shortening, using interventional tools which are introduced to a heart chamber.

US Patent Application Publication 2003/0199974 to Lee et al., which is incorporated herein by reference, describes an annuloplasty system for repairing a heart valve, comprising a surgical implant including a member having first and second end portions. The implant member further is configured and/or adapted to form a partial ring along a portion of one of the valve annulae of a patient's heart such as the mitral or tricuspid valve annulus. The implant member is axially elastic such that it can axially expand and contract and includes first and second anchors extending from the end portions of the implant member. The anchors are adapted to anchor the implant in tissue such as the mitral or tricuspid valve annulus. The system is described as facilitating tissue plication (e.g., of the posterior annulus of the mitral valve or the annulus of the tricuspid valve) and reinforcement of a valve annulus.

US Patent Application Publication 2003/0191528 to Quijano et al., which is incorporated herein by reference, describes an expandable annular ring for implantation in a valvular annulus and its percutaneous use. The ring comprises a plurality of stenting elements made of a first shape-memory material having a first shape-transition temperature, wherein the first shape-memory material expands to a preshape when the first shape-memory material is heated to above the first shape-transition temperature; and a plurality of anchoring elements made of a second shape-memory material having a second shape-transition temperature that is higher than the first shape-transition temperature, wherein the second shape-memory material expands to the second preshape when the second shape-memory material is heated to above the second shape-transition temperature.

US Patent Application Publications 2004/0260393 to Randert et al. and 2004/0127982 to Machold et al., which are incorporated herein by reference, describe techniques using an implant that is sized and configured to attach in, on, or near the annulus of a dysfunctional heart valve. In use, the implant extends either across the minor axis of the annulus, or across the major axis of the annulus, or both. The implant is described as restoring to the heart valve annulus and leaflets a more functional anatomic shape and tension. The more functional anatomic shape and tension are conducive to coaptation of the leaflets, which, in turn, reduces retrograde flow or regurgitation.

US Patent Application Publication 2004/0260394 to Douk et al., which is incorporated herein by reference, describes a cardiac valve annulus compressor comprising a generally cylindrical main body having plain and barbed ends and an actuator portion. Barbs disposed on the barbed end are engageable with the valve annulus. The length of the circumference of the barbed end is responsive to movement of the actuator portion. The annulus compressor can be delivered percutaneously or surgically.

US Patent Application Publication 2004/0236419 to Milo, which is incorporated herein by reference, describes methods for reconfiguring an atrioventricular heart valve that use systems comprising a partial or complete annuloplasty rings proportioned to reconfigure a heart valve that has become in some way incompetent, a pair of trigonal sutures or implantable anchors, and a plurality of staples which may have pairs of legs that are sized and shaped for association with the ring at spaced locations along its length. These systems are described as permitting relative axial movement between the staples and the ring, whereby a patient's heart valve can be reconfigured in a manner that does not deter subtle shifting of the native valve components. Shape memory alloy material staples may have legs with free ends that interlock following implantation. Annuloplasty rings may be complete or partial and may be fenestrated. One alternative method routes a flexible wire, preferably of shape-memory material, through the bights of pre-implanted staples. Other alternative systems use linkers of shape-memory material having hooked ends to interengage with staples or other implanted supports which, following implantation, decrease in effective length and pull the staples or other supports toward one another so as to create desired curvature of the reconfigured valve. These linkers may be separate from the supports or may be integral with them mid may have a variety of shapes and forms. Various of these systems may be implanted non-invasively using a delivery catheter.

US Patent Application Publication 2004/0243227 to Starksen et al., which is incorporated herein by reference, describes techniques for facilitating positioning of a cardiac valve annulus treatment device. The publication describes methods including advancing an anchor delivery device through vasculature of the patient to a location in the heart for treating the valve annulus, contacting the anchor delivery device with a length of the valve annulus, delivering a plurality of coupled anchors from the anchor delivery device to secure the anchors to the annulus, and drawing the anchors together to circumferentially tighten the valve annulus. Devices generally include an elongate catheter having at least one tensioning member and at least one tensioning actuator for deforming a distal portion of the catheter to help it conform to a valve annulus. The catheter device may be used to navigate a subannular space below a mitral valve to facilitate positioning of an anchor delivery device.

Odell J A et al., in an article entitled "Early Results of a Simplified Method of Mitral Valve Annuloplasty," Circulation 92:150-154 (1995), which is incorporated herein by reference, studied the outcome of three different annuloplasty techniques: commissural annuloplasty, complete ring annuloplasty, and an unmeasured, posterior, partial ring annuloplasty. They concluded that postoperative valve function obtained by unmeasured posterior annuloplasty, as assessed by degree of regurgitation, transvalvular gradient, and valve area, was similar to that obtained by measured, complete ring annuloplasty and superior to that found in patients having commissural annuloplasty.

US Patent Application Publication 2003/0078465 to Pai et al., which is incorporated herein by reference, describes techniques for treating degenerative, congestive heart disease and related valvular dysfunction. Percutaneous and minimally invasive surgical tensioning structures are implantable within various major coronary blood-carrying conduit structures (arteries, veins and branching vessels), into or through myocardium, or into engagement with other anatomic structures that impact cardiac output to provide tensile support to the heart muscle wall which resists diastolic filling pressure while simultaneously providing a compressive force to the muscle wall to limit, compensate or provide therapeutic treatment for congestive heart failure and/or to reverse the remodeling that produces an enlarged heart. In some embodiments, the tensioning structures are used to apply tension to papillary muscles and/or chordae tendineae to reposition the valve leaflets to reduce/eliminate regurgitation, to limit the motion of the leaflets to improve/restore the function of cardiac valves; and to directly reposition the valve leaflets to prevent prolapse or other abnormalities of the leaflets and to prevent associated deficiencies.

US Patent Application Publication 2003/0018358 to Saadat, which is incorporated herein by reference, describes techniques for thermally and/or mechanically treating tissue, such as valvular structures, to reconfigure or shrink the tissue in a controlled manner. Mechanical clips are implanted over the leaflets of a valve, e.g., in the heart, either alone or after thermal treatment to cause the valve to close more tightly. The clips are delivered by a catheter and may be configured to traverse directly over the valve itself or to lie partially over the periphery of the valve to prevent obstruction of the valve channel. Alternatively, individual anchors with a tensioning element, like a suture, are described as being useful for approximating the valves towards each other.

U.S. Pat. No. 6,626,899 to Houser et al., which is incorporated herein by reference, describes techniques for thermally and/or mechanically treating tissue, such as valvular structures, to reconfigure or shrink the tissue in a controlled manner. The apparatus comprises a catheter, in communication with an end effector which, induces a temperature rise in an annulus of tissue surrounding the leaflets of a valve or in the chordae tendineae sufficient to cause shrinkage, thereby causing the valves to close more tightly. Mechanical clips can also be implanted over the valve either alone or after the thermal treatment. The clips are delivered by a catheter and may be configured to traverse directly over the valve itself or to lie partially over the periphery of the valve to prevent obstruction of the valve channel.

US Patent Application Publication 2005/0222678 to Lashinski et al., which is incorporated herein by reference, describes methods and devices for applying pressure to an adjacent tissue structure, such as the annulus of the mitral valve. An adjustable implant is described with an elongate control line having a distal end connected to the implant and a proximal end spaced apart from the implant. The device enables post implantation adjustment, by accessing the proximal end of the control line and manipulating the control line to adjust the implant.

US Patent Application Publication 2005/0096740 to Langberg et al., which is incorporated herein by reference, describes a mitral annuloplasty and left ventricle restriction device adapted to be transvenously advanced and deployed within the coronary sinus and, in some embodiments, other coronary veins. The device places tension on adjacent structures, reducing the diameter and/or limiting expansion of the mitral annulus and/or limiting diastolic expansion of the left ventricle. These effects may be beneficial for patients with dilated cardiomyopathy.

SUMMARY OF THE INVENTION

In some embodiments of the present invention, a mitral valve treatment device comprises a band, a distal coupling element, and a proximal coupling element. The device is adapted to be placed around between 90 and 270 degrees of a mitral valve, including around at least a portion of a posterior cusp of the valve, in a space defined by (a) a ventricular wall, (b) a ventricular surface of the posterior cusp in a vicinity of an annulus of the mitral valve, and (c) a plurality of third-order chordae tendineae. The proximal and distal coupling elements are adapted to be coupled to a first chordae tendinea and a second chordae tendinea, respectively, each of the first and second chordae tendineae selected from the group consisting of: one of the plurality of third-order chordae tendineae, and a first-order chordae tendinea that inserts on a commissural cusp of the mitral valve. Such coupling typically tightens the annulus and thereby treats mitral valve regurgitation. Alternatively or additionally, the space is defined by a plurality of second-order chordae tendineae, and/or the distal and/or proximal end of the band is adapted to be coupled to a second-order chordae tendinea.

In some embodiments of the present invention, a mitral valve treatment device comprises an inflatable band. The band is adapted to be placed around between 90 and 270 degrees of a mitral valve, including around at least a portion of a posterior cusp of the valve, in a space defined by (a) a ventricular wall, (b) a ventricular surface of the posterior cusp in a vicinity of an annulus of the mitral valve, and (c) a plurality of third-order chordae tendineae. After placement, the band is inflated mid sealed, causing the band to press against the posterior cusp, the chordae tendineae, and the ventricular wall, thereby applying pressure to and supporting the posterior cusp. For some applications, inflation of the band additionally holds the band in place. For some applications, the band comprises neither a distal nor a proximal coupling element, or comprises only a single coupling element.

In some embodiments of the present invention, a method for treating mitral valve regurgitation comprises inserting a band around between 90 and 270 degrees of a mitral valve, including around at least a portion of a posterior cusp of the valve, in a space defined by (a) a ventricular wall, (b) a ventricular surface of the posterior cusp in a vicinity of an annulus of the mitral valve, and (c) a plurality of third-order chordae tendineae. The method further comprises coupling a distal end and a proximal end of the band to a first chordae tendinea and a second chorda tendinea, respectively, each of the first and second chordae tendineae selected from the group consisting of: one of the plurality of third-order chordae tendineae, and a first-order chorda tendinea that inserts on a commissural cusp of the mitral valve: Such coupling typically tightens the annulus and, thereby treats mitral valve regurgitation. Alternatively or additionally, the space is defined by a plurality of second-order chordae tendineae, and/or the distal and/or proximal end of the band is coupled to a second-order chorda tendinea.

In some embodiments of the present invention, apparatus for treating a mitral valve comprises an outward force applicator adapted to be placed around between 90 and 270 degrees of a mitral valve of a heart. The force applicator is configured such that at least two regions thereof (typically end regions) apply force to a wall of a heart chamber in a vicinity of the commissural cusps of the mitral valve. Such outwardly-applied force draws the commissural cusps away from one another, stretching the mitral valve and thereby bringing the posterior and anterior cusps of the valve closer to one another. The device is thus useful for treating mitral valve regurgitation.

In some embodiments of the present invention, the force applicator is adapted to be placed in a space defined by (a) a ventricular wall, (b) a ventricular surface of at least one of the mitral valve cusps in a vicinity of an annulus of the mitral valve, and (c) a plurality of third-order chordae tendineae. Alternatively or additionally, the space is defined by a plurality of second-order chordae tendineae. Further alternatively, the force applicator is adapted to be placed in a left atrium of the heart, in contact with or in a vicinity of the mitral valve.

In some embodiments of the present invention, the force applicator comprises one or more coupling elements, which are adapted to hold the force applicator in place after placement. For some applications, the coupling elements comprise one or more protrusions, oriented on the force applicator such that the protrusions contact and grip the wall of the heart. Typically, the protrusions are positioned in a vicinity of the ends of the force applicator, and/or along the length of the force applicator, such as in a vicinity of a middle of the force applicator. For other applications, the coupling elements are adapted to be coupled to the mitral valve, and/or to one or more chordae tendineae, such as third-order chordae tendineae, or second-order chordae tendineae. For these applications, the coupling elements may comprise, for example, hooks, sutures, or staples.

There is therefore provided, in accordance with an embodiment of the present invention, apparatus for treating mitral valve regurgitation, including:

a band having distal and proximal ends, the band adapted to be placed:
  around between 90 and 270 degrees of a mitral valve, including around at least a portion of a posterior cusp of the valve,
  in a space defined by (a) a ventricular wall, (b) a ventricular surface of the posterior cusp in a vicinity of an annulus of the mitral valve,
  and (c) a plurality of third-order chordae tendineae; and
  distal and proximal coupling elements, coupled to the band at the distal and proximal ends thereof, respectively, and adapted to be coupled to a first chorda tendinea and a second chorda tendinea, respectively, each of the first and second chordae tendineae selected from the group consisting of: one of the plurality of third-order chordae tendineae, and a first-order chorda tendinea that inserts on a commissural cusp of the mitral valve.

In an embodiment, each of the first and second chordae tendineae includes one of the plurality of third-order chordae tendineae, and the distal and proximal coupling elements are adapted to be coupled to the respective ones of the plurality of third order chordae tendineae.

In an embodiment, the distal and proximal coupling elements are adapted to be coupled to the first and second chordae tendineae such that the band tightens the annulus of the valve. Alternatively or additionally, the distal and proximal coupling elements are adapted to be coupled to the first and second chordae tendineae such that the band applies pressure to the posterior cusp. For some applications, the distal and proximal coupling elements are adapted to be coupled to the first and second chordae tendineae such that the band applies substantially no pressure to an anterior cusp of the valve. For some applications, the distal and proximal coupling elements are adapted to be coupled to the first and second chordae tendineae such that the band does not squeeze an anterior cusp of the valve and the posterior cusp together.

For some applications, the distal and proximal coupling elements include respective hooks, adapted to be hooked to the first and second chordae tendineae, respectively.

For some applications, the band is generally elliptical in cross-section. Alternatively, the band is flat.

For some applications, the band includes at least one sensor selected from the group consisting of: a wireless position sensor, and a navigation sensor. For some applications, the band includes a steering mechanism.

For some applications, the band includes a shape memory alloy, and the shape memory alloy causes the band to assume a curved shape during placement of the band.

For some applications, the band includes a tension element, adapted to shorten a length of the band. For some applications, at least a portion of the band includes an elastic material, adapted to shorten a length of the band.

For some applications, the band is coated with a substance selected from the group consisting of: a drug, and a radiopaque coating.

For some applications, the band is adapted to be placed around no portion of an anterior cusp of the valve. For some applications, the band is adapted to be placed such that a length of a first portion of the band that surrounds the at least a portion of the posterior cusp is at least 5 times a total length of that portion of the band that surrounds at least a portion of an anterior cusp of the valve.

For some applications, the band includes a distal stop, and the distal coupling element is adapted to slide along the band until blocked by the distal stop.

For some applications, the band includes a plurality of bands, the bands adapted to be placed in series around between 90 and 270 degrees of the mitral valve.

For some applications, the apparatus includes an elongated insertion element, adapted to releasably engage the proximal end of the band.

In an embodiment, the proximal coupling element is adapted to slide along the band and subsequently be locked to the band. For some applications, a portion of the band in a vicinity of the proximal end is shaped so as to define a first set of teeth, an interior surface of the proximal coupling element is shaped so as to define a second set of teeth, and the teeth are configured to allow distal advancement of the proximal coupling element along the band, and to not allow proximal retraction of the proximal coupling element along the band.

For some applications, the apparatus includes a crimping mechanism, adapted to be placed around the proximal coupling element and to crimp the proximal coupling element to the band.

For some applications, a portion of the band in a vicinity of the proximal end is shaped so as to define a first set of teeth, an interior surface of the proximal coupling element is shaped so as to define a second set of teeth, and the crimping element is adapted to crimp the proximal coupling element to the band by crimping at least a portion of the second set of teeth to at least a portion of the first set of teeth. For some applications, the crimping mechanism includes an inflation element, adapted, upon inflation thereof, to crimp the proximal coupling element to the band.

For some applications, the band is shaped so as to define one or more indentations therein, and the proximal coupling element includes a tension clip, adapted to engage at least one of the indentations, so as to lock the proximal coupling element to the band.

For some applications, the band is adapted to be placed around between 120 and 240 degrees of the mitral valve, such as between 150 and 210 degrees of the mitral valve.

There is also provided, in accordance with an embodiment of the present invention, apparatus for treating mitral valve regurgitation, including:

a band having distal and proximal ends, the band adapted to be placed:
  around between 90 and 270 degrees of a mitral valve, including around at least a portion of a posterior cusp of the valve,
  in a space defined by (a) a ventricular wall, (b) a ventricular surface of the posterior cusp in a vicinity of an annulus of the mitral valve,
  and (c) a plurality of second-order chordae tendineae; and
  distal and proximal coupling elements, coupled to the band at the distal and proximal ends thereof, respectively, and adapted to be coupled to a first chorda tendinea and a second chorda tendinea, respectively, each of the first and second chordae tendineae selected from the group consisting of: one of the plurality of second-order chordae tendineae, and a first-order chorda tendinea that inserts on a commissural cusp of the mitral valve.

There is further provided, in accordance with an embodiment of the present invention, apparatus for treating mitral valve regurgitation, including a band adapted to be placed:
around between 90 and 270 degrees of a mitral valve of a heart, including around at least a portion of a posterior cusp of the valve,
in a space defined by (a) a ventricular wall, (b) a ventricular surface of the posterior cusp in a vicinity of an annulus of the mitral valve, and (c) a plurality of third-order chordae tendineae,
the band configured such that inflation thereof applies pressure to the posterior cusp.

In an embodiment, the band is configured such that inflation thereof holds the band in place.

For some applications, the apparatus includes a liquid for inflating the band, the liquid adapted to at least partially solidify after inflation of the band therewith.

In an embodiment, the band is not configured to be coupled to any portion of the heart, other than by the inflation thereof.

There is still further provided, in accordance with an embodiment of the present invention, apparatus for treating mitral valve regurgitation, including a band adapted to be placed:
around between 90 and 270 degrees of a mitral valve, including around at least a portion of a posterior cusp of the valve,
in a space defiled by (a) a ventricular wall, (b) a ventricular surface of the posterior cusp in a vicinity of an annulus of the mitral valve,
and (c) a plurality of second-order chordae tendineae,
the band configured such that inflation thereof applies pressure to the posterior cusp.

In an embodiment, the band is configured such that inflation thereof holds the band in place.

There is yet further provided, in accordance with an embodiment of the present invention, apparatus for treating mitral valve regurgitation, including:
a stent, adapted to be placed while in a contracted state around between 90 and 270 degrees of a mitral valve of a heart, including around at least a portion of a posterior cusp of the valve, in a space defined by (a) a ventricular wall, (b) a ventricular surface of the posterior cusp in a vicinity of an annulus of the valve, and (c) a plurality of third-order chordae tendineae; and
an inflation element, positioned within the stent, and adapted to expand the stent upon inflation, such that the Stent applies pressure to the posterior cusp.

In an embodiment, the stent includes at least one coupling element, adapted to be coupled to a chorda tendinea.

For dome applications, the stent includes a plurality of stents, adapted to be placed in series around between 90 and 270 degrees of the mitral valve.

There is additionally provided, in accordance with an embodiment of the present invention, a method for treating mitral valve regurgitation, including:
inserting a band around between 90 and 270 degrees of a mitral valve, including around at least a portion of a posterior cusp of the valve, in a space defined by (a) a ventricular wall, (b) a ventricular surface of the posterior cusp in a vicinity of an annulus of the valve, and (c) a plurality of third-order chordae tendineae; and
coupling a distal end and a proximal end of the band to a first chorda tendinea and a second chorda tendinea, respectively, each of the first and second chordae tendineae selected from the group consisting of: one of the plurality of third order chordae tendineae, and a first-order chorda tendinea that inserts on a commissural cusp of the mitral valve.

For some applications, inserting includes inserting the band via an ascending aorta.

For some applications, the band includes at least one sensor selected from the group consisting of: a wireless position sensor, and a navigation sensor, and inserting includes inserting the band at least in part responsively to a signal generated by the sensor.

For some applications, the band includes a distal stop and a distal coupling element, and coupling the distal end of the band to the first chorda tendinea includes:
advancing the band until the distal stop reaches a vicinity of the first chorda tendinea;
advancing the distal coupling element over the band until the distal coupling element reaches the distal stop; and
coupling the distal coupling element to the first chorda tendinea.

In an embodiment, the band includes a proximal coupling element, and coupling includes:
coupling the distal end of the band to the first chorda tendinea;
thereafter, sliding the proximal coupling element along the band until the band has a desired length between the distal end and the proximal coupling element; and
locking the proximal coupling element to the band.

For some applications, coupling includes, after locking the proximal coupling element, clipping a portion of the band proximal to the proximal coupling element. For some applications, coupling includes, after locking the proximal coupling element, releasing the band from an elongated insertion element, and withdrawing the insertion element from the heart.

For some applications, a portion of the band in a vicinity of the proximal end includes a first set of teeth, an interior surface of the proximal coupling element includes a second set of teeth, the teeth are configured to allow distal advancement of the proximal coupling element along the band, and to not allow proximal retraction of the proximal coupling element along the band, and locking the proximal coupling element includes advancing the proximal coupling element until the band has the desired length.

There is yet additionally provided, in accordance with an embodiment of the present invention; a method for treating mitral valve regurgitation, including:
inserting a band around between 90 and 270 degrees of a mitral valve, including around at least a portion of a posterior cusp of the valve, in a space defined by (a) a ventricular wall, (b) a ventricular surface of the posterior cusp in a vicinity of an annulus of the valve, and (c) a plurality of second-order chordae tendineae; and
coupling a distal end and a proximal end of the band to a first chorda tendinea and a second chorda tendinea, respectively, each of the first and second chordae tendineae selected from the group consisting of: one of the plurality of second-order chordae tendineae, and a first-order chorda tendinea that inserts on a commissural cusp of the mitral valve.

There is still additionally provided, in accordance with an embodiment of the present invention, a method for treating mitral valve regurgitation, including:

inserting a band around between 90 and 270 degrees of a mitral valve of a heart, including around at least a portion of a posterior cusp of the valve, in a space defined by (a) a ventricular wall, (b) a ventricular surface of the posterior cusp in a vicinity of an annulus of the valve, and (c) a plurality of third-order chordae tendineae; and applying pressure to the posterior cusp by inflating the band.

There is also provided, in accordance with an embodiment of the present invention, a method for treating mitral valve regurgitation, including:

inserting a band around between 90 and 270 degrees of a mitral valve, including around at least a portion of a posterior cusp of the valve, in a space defined by (a) a ventricular wall, (b) a ventricular surface of the posterior cusp in a vicinity of an annulus of the valve, and (c) a plurality of second-order chordae tendineae; and applying pressure to the posterior cusp by inflating the band.

There is further provided, in accordance with an embodiment of the present invention, a method for treating mitral valve regurgitation, including:

inserting a stent in a contracted state around between 90 and 270 degrees of a mitral valve of a heart, including around at least a portion of a posterior cusp of the valve, in a space defined by (a) a ventricular wall, (b) a ventricular surface of the posterior cusp in a vicinity of an annulus of the valve, and (c) a plurality of third-order chordae tendineae; and applying pressure to the posterior cusp by expanding the stent by inflating an inflation element positioned within the stent.

There is still further provided, in accordance with an embodiment of the present invention, apparatus for treating mitral valve regurgitation, including a force applicator adapted to be placed around at least a portion of a mitral valve of a heart, and configured such that at least two regions of the force applicator apply, to a wall of a chamber of the heart in a vicinity of commissural cusps of the mitral valve, force sufficient to bring a posterior cusp and an anterior cusp of the mitral valve closer to one another than a distance therebetween in the absence of the force applicator.

In an embodiment, the applicator is adapted to be placed in a space defined by (a) a ventricular wall, (b) a ventricular surface of the posterior cusp in a vicinity of an annulus of the valve, and (c) a plurality of third-order chordae tendineae. Alternatively, in an embodiment, the applicator is adapted to be placed in a space defined by (a) a ventricular wall, (b) a ventricular surface of the posterior cusp in a vicinity of an annulus of the valve, and (c) a plurality of second-order chordae tendineae.

In an embodiment, the applicator is adapted to be placed in a left atrium of the heart, in contact with or in a vicinity of the mitral valve.

For some applications, the applicator is generally elliptical in cross-section. Alternatively, the applicator is flat.

For some applications, the applicator is coated with a substance selected from the group consisting of: a drug, and a radiopaque coating.

For some applications, the applicator is adapted to be placed around no portion of the anterior cusp. For some applications, the applicator is adapted to be placed such that a length of a first portion of the applicator that surrounds at least a portion of the posterior cusp is at least 5 times a total length of that portion of the applicator that surrounds at least a portion of the anterior cusp.

For some applications, the applicator is configured to enhance fibrosis between at least a portion of the applicator and the wall of the chamber.

For some applications, the applicator includes at least one sensor selected from the group consisting of: a wireless position sensor, and a navigation sensor. For some applications, the applicator includes a steering mechanism.

For some applications, the applicator has distal and proximal ends, and the applicator includes an adjustment mechanism, which is configured to change a distance between the distal end and the proximal end of the applicator.

For some applications, the applicator is shaped so as to define one or more protrusions, oriented such that the protrusions contact the wall of the chamber of the heart upon placement of the applicator.

In an embodiment, the applicator includes one or more coupling elements, adapted to hold the applicator in place around the at least a portion of the valve. For some applications, the coupling elements are adapted to be coupled to the valve. Alternatively, the coupling elements are adapted to be coupled to respective chordae tendineae.

In an embodiment, the applicator is adapted to be placed around between 90 and 270 degrees of the mitral valve, such as around between 120 and 240 degrees of the mitral valve, e.g., around between 150 and 210 degrees of the mitral valve.

In an embodiment, the applicator is configured such that after placement of the applicator, and before the at least two regions apply the force, there is a gap between the applicator and the wall of the chamber. For some applications, the applicator is configured such that the force applied by the at least two regions reduces a distance between the applicator and the wall of the chamber in a vicinity of the gap. For some applications, the applicator is configured such that the force applied by the at least two regions immediately reduces the distance. Alternatively, the applicator is configured such that the force applied by the at least two regions reduces the distance within one month of application of the force.

In an embodiment, the at least two regions include two end regions of the force applicator, and the force applicator is configured such that at least the two end regions apply the force. For some applications, the applicator includes at least one screw in a vicinity of at least one of the end regions, the screw configured such that rotation thereof adjust a degree of pushing of the at least one end region into the wall of the chamber.

There is additionally provided, in accordance with an embodiment of the present invention, apparatus for treating mitral valve regurgitation, including a force applicator adapted to be placed around at least a portion of a mitral valve of a heart, and configured to:

apply force to a wall of a chamber of the heart, so as to change a shape of the heart around the mitral valve, and enhance fibrosis between at least a portion of the force applicator and the heart wall, so as to help maintain the changed shape of the heart.

For some applications, a surface of the at least a portion of the applicator is roughened to enhance fibrosis. Alternatively or additionally, the at least a portion of the applicator is coated with a fibrosis-enhancing substance.

There is yet additionally provided, in accordance with an embodiment of the present invention, a method for treating mitral valve regurgitation, including placing, around at least a portion of a mitral valve of a heart, a force applicator configured such that at least two regions of the force applicator apply, to a wall of a chamber of the heart in a vicinity of commissural cusps of the mitral valve, force sufficient to bring a posterior cusp and an anterior cusp of the mitral valve closer to one another than a distance therebetween in the absence of the force applicator.

For some applications, the applicator includes at least one sensor selected from the group consisting of: a wireless position sensor, and a navigation sensor, and placing includes placing the applicator at least in part responsively to a signal generated by the sensor.

There is also provided, in accordance with an embodiment of the present invention, a method for treating mitral valve regurgitation, including placing, around at least a portion of a mitral valve of a heart, a force applicator configured to apply force to a wall of a chamber of the heart, so as to change a shape of the heart around the mitral valve, and to enhance fibrosis between at least a portion of the force applicator and the heart wall, so as to help maintain the changed shape of the heart.

The present invention will be more fully understood from the following detailed description of embodiments thereof, taken together with the drawings, in which:

BRIEF DESCRIPTION OF THE DRAWINGS

FIG. 5 is a schematic illustration of a distal end of a catheter for introducing the device of FIG. 1 into the heart, in accordance with an embodiment of the present invention;

FIGS. 6A-B are schematic illustrations of a mitral valve before and after placement of the device of FIG. 1, respectively, in accordance with an embodiment of the present invention;

FIGS. 11A-B are schematic illustrations of yet another sliding and locking mechanism of the device of FIG. 1, in accordance with an embodiment of the present invention;

FIG. 16 is a schematic illustration of a configuration of the device of FIG. 1, in accordance with an embodiment of the present invention;

FIGS. 17A-B are schematic illustrations, of a stent adapted for treatment of a mitral valve, in accordance with an embodiment of the present invention;

FIG. 18 is a schematic illustration of a mitral valve treatment force applicator placed in a heart, in accordance with an embodiment of the present invention;

DETAILED DESCRIPTION OF EMBODIMENTS

Figure 1:
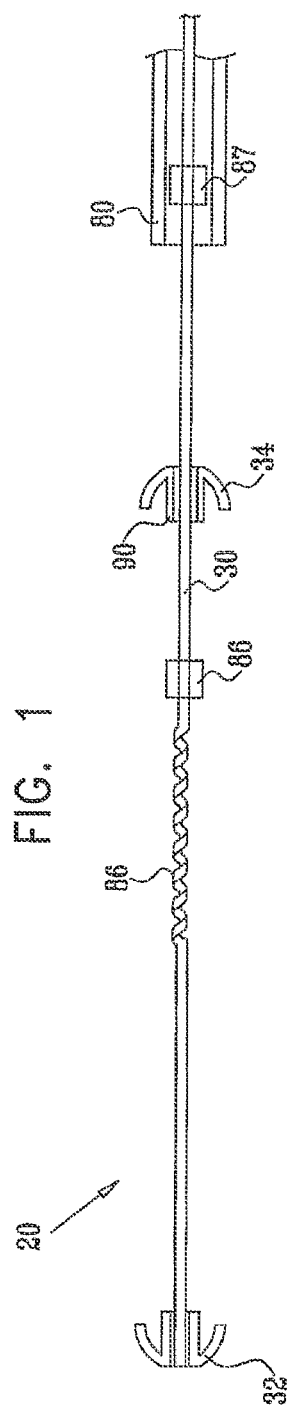
FIG. 1 is a schematic illustration of a mitral valve treatment device, in accordance with an embodiment of the present invention.

FIG. 1 is a schematic illustration of a mitral valve treatment device 20, in accordance with an embodiment of the present invention. Device 20 typically comprises a flexible band 30, a distal coupling element 32 (e.g., a hook), and a proximal coupling element 34 (e.g., a hook). For some applications, band 30 is generally elliptical in cross-section (e.g., circular), while for other applications the band is flat, e.g., ribbon-shaped. Band 30 typically comprises a biocompatible material, such as a polymer or metal. For some applications, band 30 is coated with a drug and/or a radiopaque coating.

Figure 2:
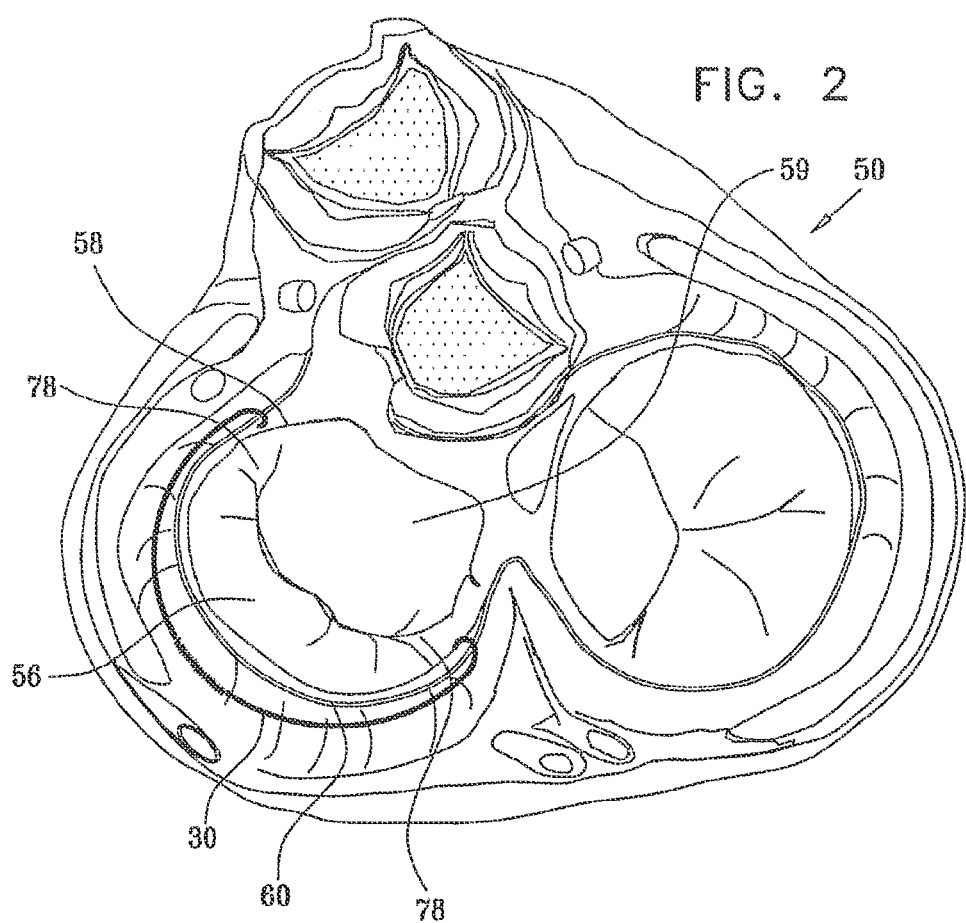
FIG. 2 is a schematic illustration of the device of FIG. 1 placed in a heart, in accordance with an embodiment of the present invention.

Reference is made to FIG. 2, which is a schematic illustration of band 30 placed in a heart 50, which is viewed from above the heart with the atria removed, in accordance with an embodiment of the present invention. Band 30 is adapted to be placed around between 90 and 270 degrees of a mitral valve 58 of a heart 50, including around at least a portion of a posterior cusp 56 of mitral valve 58, in a vicinity of an annulus 60 of mitral valve 58. For some applications, band 30 is adapted to be placed around between 120 and 240 degrees, such as between 150 and 210 degrees, e.g., about 180 degrees, of the mitral valve. For some applications, band 30 is adapted to be placed substantially only around all or a portion of posterior cusp 56, i.e., substantially not around any portion of an anterior cusp 59 of mitral valve 58. For example, the length of band 30 surrounding posterior cusp 56 is typically at least about 5 or at least about 10 times the length of any portion of band 30 that may be surrounding anterior cusp 59.

For some applications, band 30 is anchored in place by distal coupling element 32 and proximal coupling element 34, such that the band applies pressure to posterior cusp 56, thereby tightening annulus 60, supporting the posterior cusp, and bringing the posterior cusp closer to the anterior cusp. For applications in which a portion of band 30 is placed around a portion of anterior cusp 59, band 30 typically applies force substantially only to posterior cusp 56. Furthermore, band 30 is typically configured to apply pressure to posterior cusp 56, rather than to squeeze the posterior and anterior cusps together.

Figure 3:
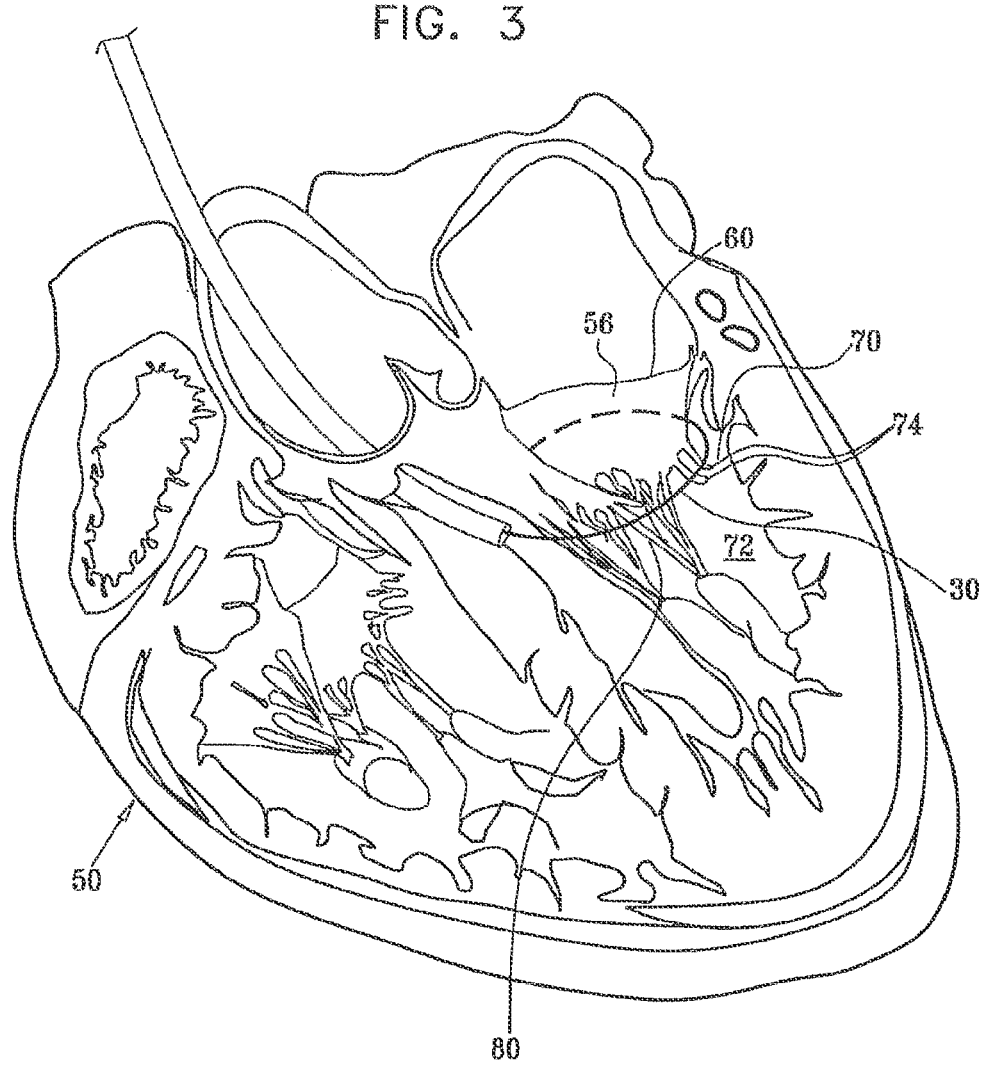
FIG. 3 is a schematic illustration of a portion of the device of FIG. 1 placed around a portion of a posterior cusp of a mitral valve, in accordance with an embodiment of the present invention.

Reference is made to FIG. 3, which is a schematic illustration of a portion of band 30 placed around a portion of posterior cusp 56, in accordance with an embodiment of the present invention. Typically, band 30 is placed in the space defined by a ventricular wall 70 of left ventricle 72, a ventricular surface of posterior cusp 56 in a vicinity of annulus 60, and third-order chordae tendineae 74 (also called tertiary or basal chordae). (Third-order chordae 74, of which only two of many are shown in the figure for clarity of illustration, originate directly from the trabeculae carneae of ventricular wall 70, and attach to posterior cusp 56 in a vicinity of annulus 60.) Alternatively or additionally, the space is defined by second-order chordae tendineae (not shown in the figure). Typically, distal and proximal coupling elements 32 and 34 are coupled to first and second chordae tendineae, respectively, each of which is selected from the group consisting of: one of third-order chordae 74, a first-order chorda tendinea that inserts on a commissural cusp 78 of mitral valve 58 (shown in FIG. 2), and a second-order chorda tendinea (not shown in the figures). Typically, when in place, band 30 is in contact with one or more third- or second-order chordae tendineae, and/or the ventricular surface of posterior cup 56 in the vicinity of annulus 60.

Alternatively or additionally, band 30 is placed around first-order chordae tendineae 80 that insert on posterior cusp 56, anterior cusp 59, and/or commissural cusps 78 (configuration not shown in the figures). Further alternatively or additionally, band 30 is woven between the first-, second-, and/or third-order chordae.

Figure 4:
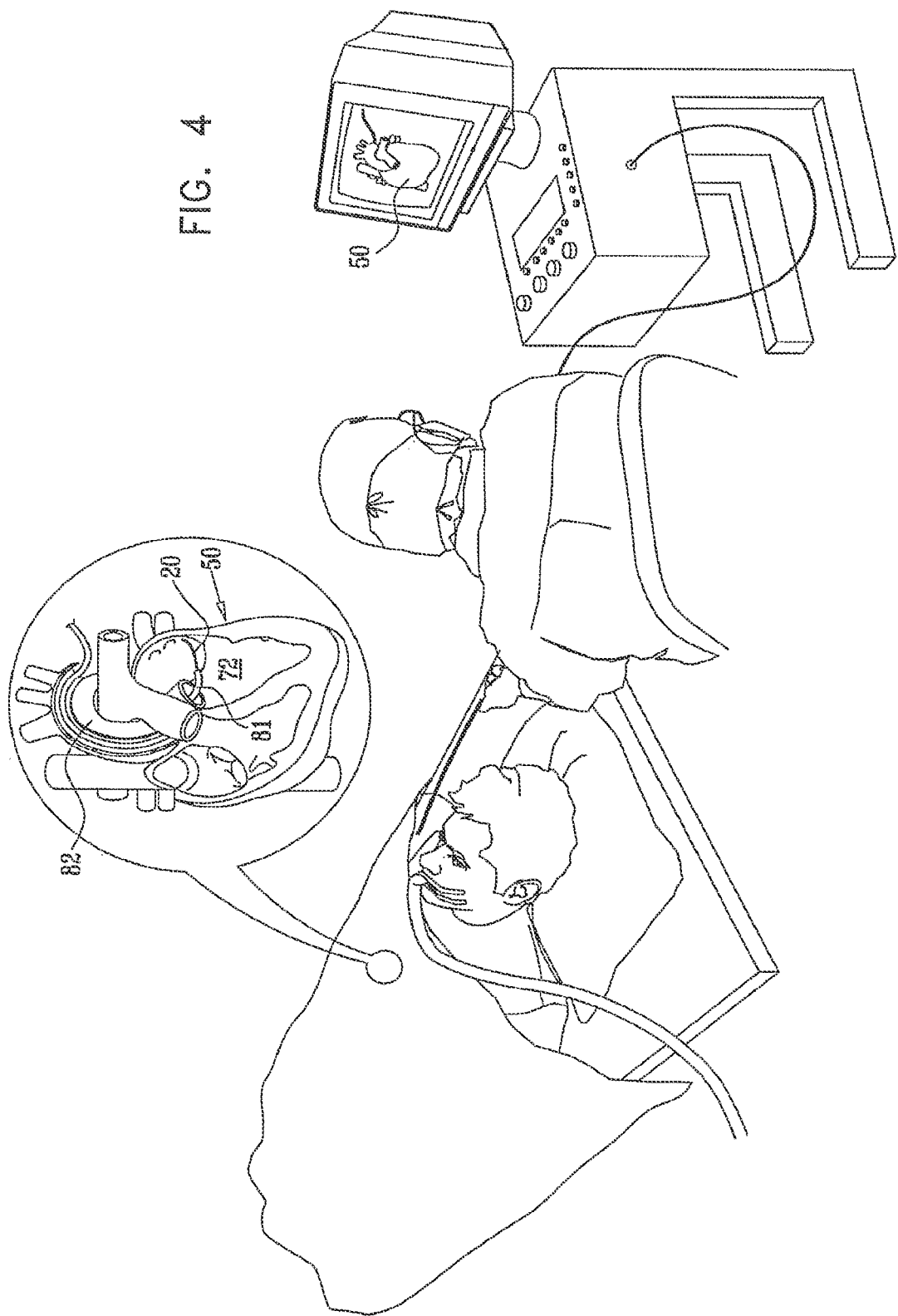
FIG. 4 is a schematic illustration of a procedure for introducing the device of FIG. 1 into the heart, in accordance with an embodiment of the present invention.

Reference is made to FIG. 4, which is a schematic illustration of a procedure for introducing device 20 into heart 50 of a subject, in accordance with an embodiment of the present invention. Typically, device 20 is introduced into ventricle 72 by a catheter 81, which is typically introduced into ventricle 72 via an ascending aorta 82. A surgeon typically guides device 20 to a desired location using images of heart 50 captured using techniques known in the art. For some applications, device 20 comprises, e.g., at a distal end thereof, one or more wireless position sensors, such as those manufactured by Biosense, Inc. (New Brunswick, N.J.), or otherwise known in the art. Alternatively or additionally, device 20 comprises, e.g., at a distal end thereof, one or more sensors for aiding navigation, such as an ultrasound sensor, an infrared sensor, or an optical sensor. For some applications, device 20 comprises a steering mechanism, such as those known in the art of coronary catheter navigation. For some applications, band 30 comprises a shape memory alloy, such as nitinol, which causes the band to assume a curved shape, thereby assisting in navigating the band around the chordae tendineae. For some applications, the surgeon magnetically navigates band 30, such as using techniques described in U.S. Pat. No. 6,817,364 or 6,522,909 to Garibaldi et al., or U.S. Pat. No. 6,475,223 to Werp et al., which are incorporated herein by reference, mutatis mutandis.

Reference is made to FIG. 5, which is a schematic illustration of a distal end 84 of catheter 81, in accordance with an embodiment of the present invention. In this embodiment, the distal end of catheter 81 opens laterally, rather than at its end, so as to guide device 20 towards mitral valve 58 after the catheter is inserted into left ventricle 72.

Reference is made to FIGS. 6A-B, which are schematic illustrations of mitral valve 58 before and after placement of band 30, respectively, in accordance with an embodiment of the present invention. FIG. 6A shows mitral valve regurgitation occurring prior to the placement of band 30. FIG. 6A also shows band 30 as it is being placed around posterior cusp 56. FIG. 6B shows band 30 after it has been anchored in place around posterior cusp 56, thereby preventing regurgitation.

Reference is again made to FIG. 1. In an embodiment of the present invention, band 30 is adapted to tense, so as to shorten its length. For some applications, band 30 comprises a tension element 88, such as a spring. Alternatively or additionally, all or a portion of band 30 comprises an elastic material. For some applications, the tension serves to increase the force applied by band 30 to posterior cusp 56 after the band has been coupled to the chordae tendineae.

Figure 7A:
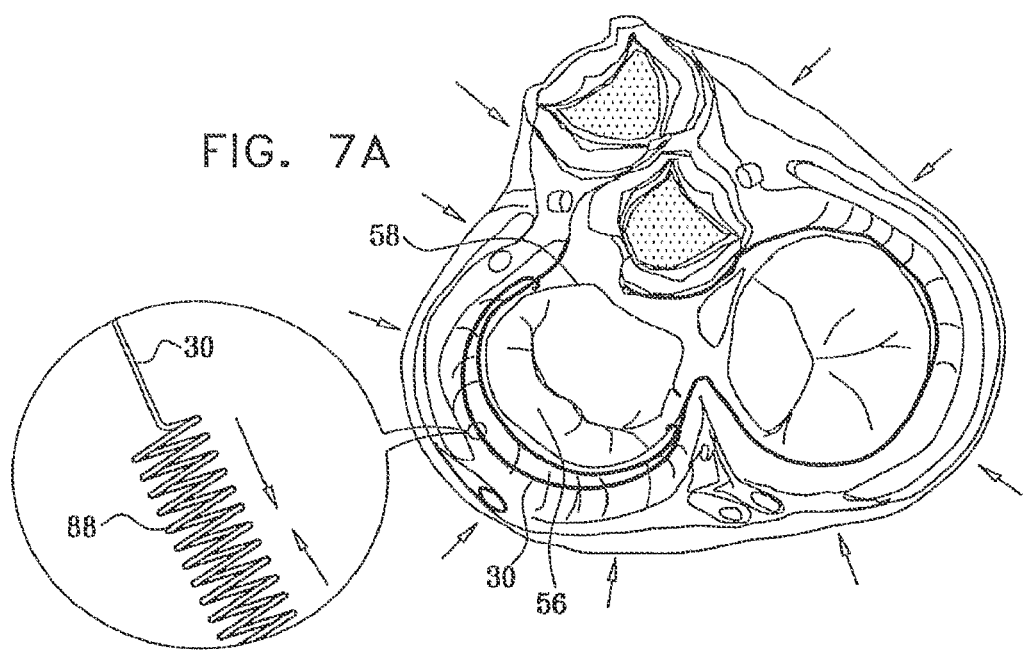
FIGS. 7A-B are schematic illustrations of the device of FIG. 1 during systole and diastole, respectively, in accordance with an embodiment of the present invention.
Figure 7B:
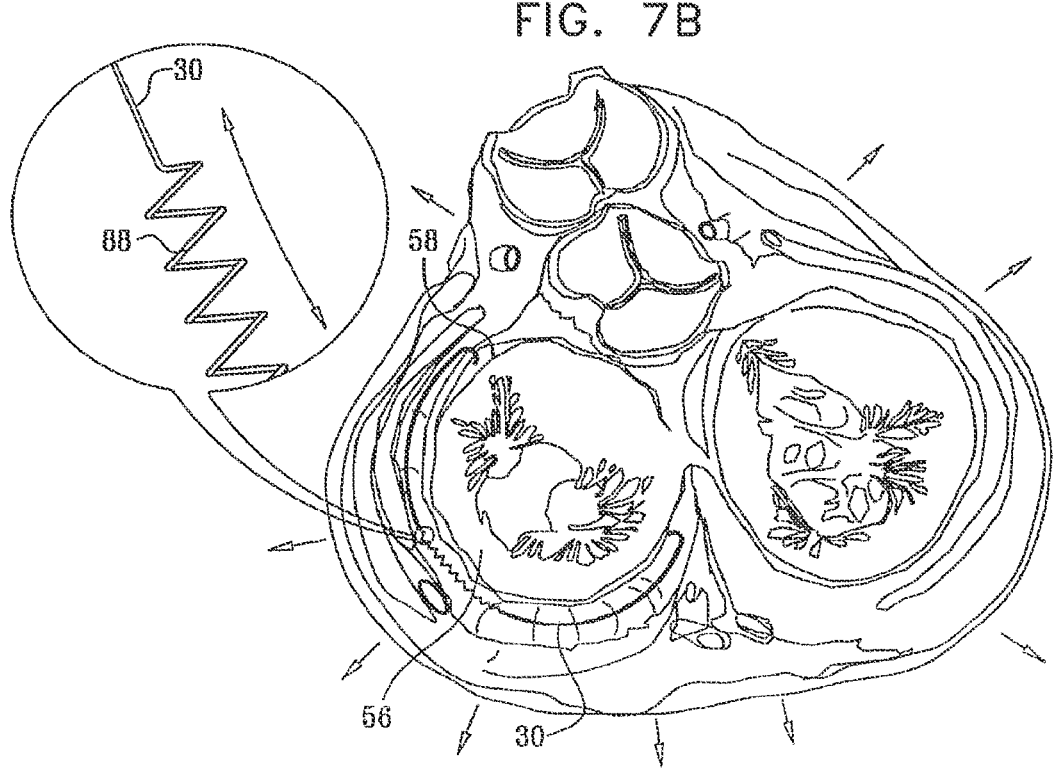

Reference is now made to FIGS. 7A-B, which are schematic illustrations of band 30 during systole and diastole, respectively, in accordance with an embodiment of the present invention. In this embodiment, band 30 comprises tension element 88, and/or band 30 comprises an elastic material. As shown in FIG. 7A, during systole tension element 88 contracts, increasing the pressure applied by band 30 to posterior cusp 56. During diastole, as shown in FIG. 7B, tension element 88 expands, reducing the pressure applied by band 30 to posterior cusp 56, and allowing mitral valve 58 to open.

Figure 8A:
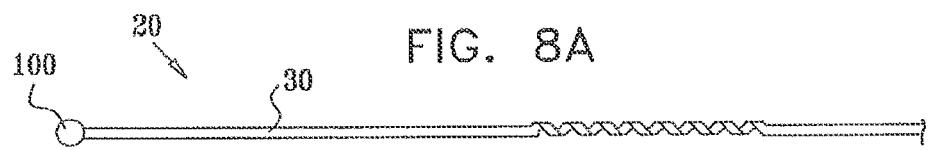
FIGS. 8A-B are schematic illustrations of an over-the-wire implementation of the device of FIG. 1, in accordance with an embodiment of the present invention.
Figure 8B:
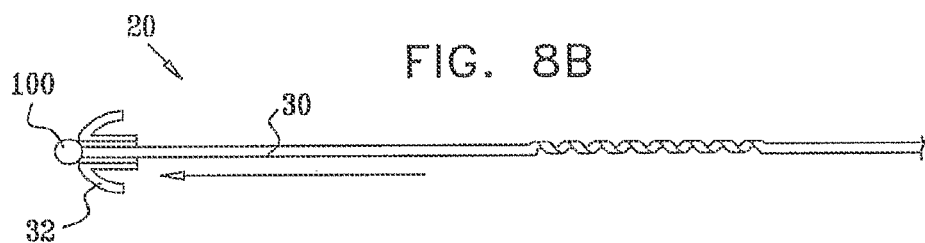

Reference is now made to FIGS. 8A-B, which are schematic illustrations of an over-the-wire implementation of device 20, in accordance with an embodiment of the present invention. In this embodiment, band 30 comprises a distal stop 100, which, for example, may be spherical. Distal coupling element 32 is adapted to slide distally along band 30 until blocked by distal stop 100. During placement, band 30 is advanced until distal stop 100 reaches a vicinity of the chorda tendinea to which the distal end of the band will be coupled. Distal coupling element 32 is then advanced over band 30 until it reaches the distal end of the band. For example, the surgeon may advance catheter 81 over band 30 in order to push distal coupling element 32 to the distal end of the band. The surgeon then couples the coupling element to the chorda tendinea. Typically, the coupling of distal coupling element 32 to the chorda tendinea prevents subsequent proximal sliding of the coupling element. Alternatively, a locking mechanism is provided to hold coupling element 32 in place once it reaches distal stop 100. The use of distal stop 100 and the techniques described in this paragraph typically enable easier advancement of band 30 than in embodiments in which distal coupling element 32 is fixed to the distal end of band 30 during advancement.

Reference is again made to FIG. 1. In an embodiment of the present invention, proximal coupling element 34 comprises a sliding and locking mechanism 90. Sliding and locking mechanism 90 is configured to have a locked position and an unlocked position. When in the unlocked position, the mechanism is able to slide along band 30, and when in the locked position, the mechanism is fixed to the band. Typically, during placement of device 20 a surgeon couples distal coupling element 32 to a chorda tendinea at a desired location, and slides proximal coupling element 34 along band 30 so that band 30 has a desired length between the two coupling elements. The surgeon then locks mechanism 90, and clips the portion of band 30 proximal to proximal coupling element 34. For some applications, the surgeon locks and/or clips the excess portion before coupling proximal coupling element to a chorda tendinea, while for other applications the surgeon locks and/or clips the excess portion after coupling proximal coupling element to a chorda tendinea. Alternatively, rather than being clipped, band 30 is released from a release mechanism, as described hereinbelow with reference to FIGS. 13A-B.

Typically, the tension of band 30 is determined by the selected length of band 30 and the locations at which coupling elements 32 and 34 are coupled to the chordae. For some applications, the surgeon adjusts the tension of band 30 based on (a) tactile feedback, (b) a force measurement, and/or (c) another measurement, such as an electrocardiographic measurement, and/or a blood flow measurement made in the heart or elsewhere in the body. For some applications, band 30 comprises at least one tension or pressure sensor 86, which is adapted to measure the tension of band 30. Alternatively or additionally, device 20 comprises a tension control system 87 proximal to proximal coupling element 34.

Figure 9A:
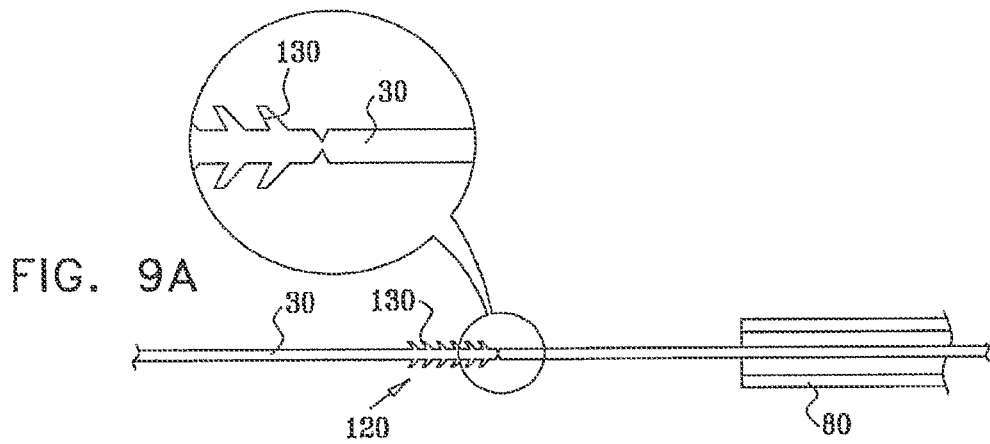
FIGS. 9A-B are schematic illustrations of a sliding and locking mechanism of the device of FIG. 1, in accordance with an embodiment of the present invention.
Figure 9B:
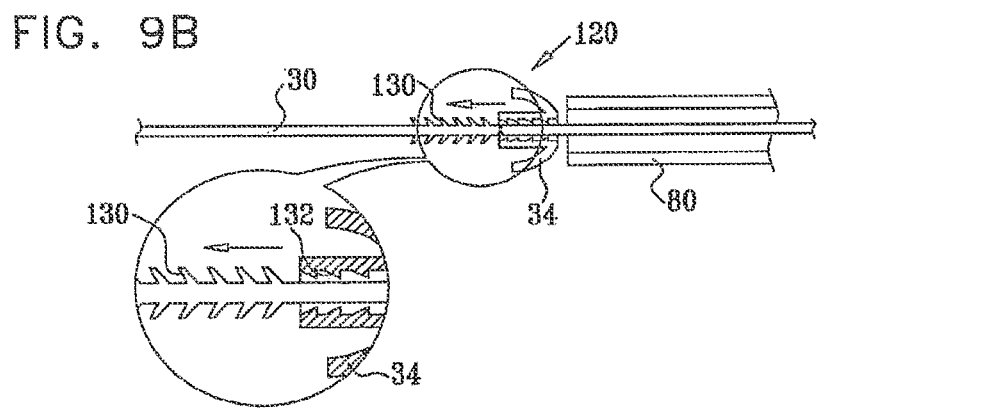

Reference is made to FIGS. 9A-B, which are schematic illustrations of another sliding and locking mechanism 120 of band 30, in accordance with an embodiment of the present invention. Mechanism 120 comprises two interlocking sets of teeth. A first set of teeth 130 is coupled to or integrated into a proximal portion of band 30, and a second set of teeth 132 is coupled to or integrated into an interior surface of proximal coupling element 34. The teeth are configured to allow distal advancement of coupling element 34 over band 30, but to not allow proximal retraction of the coupling element. The surgeon distally advances coupling element 34 over band 30 so that band 30 has a desired length between the two coupling elements.

Figure 10A:
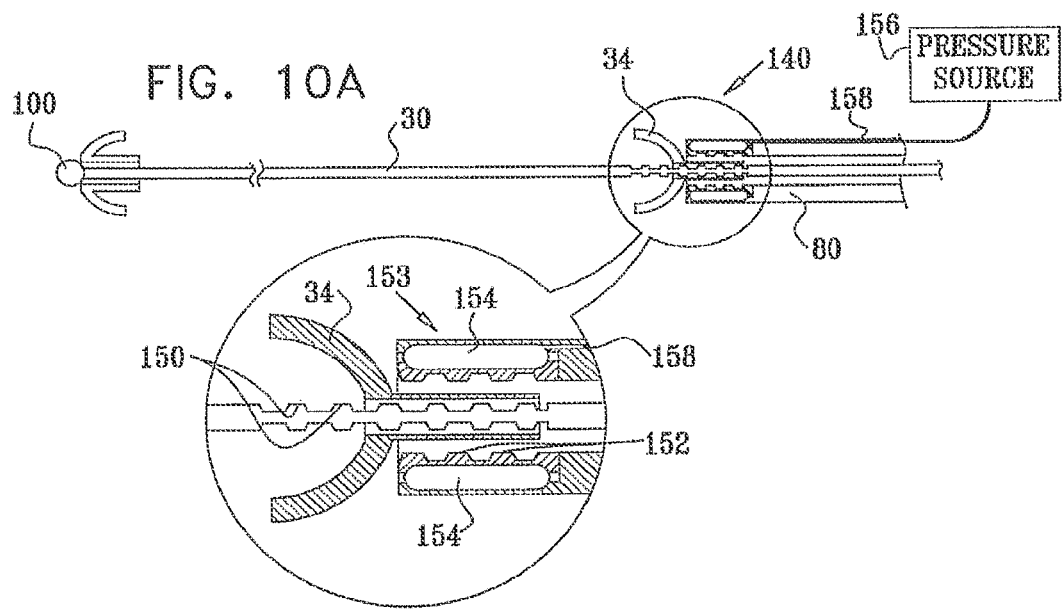
FIGS. 10A-C are schematic illustrations of another sliding and locking mechanism of the device of FIG. 1, in accordance with an embodiment of the present invention.
Figure 10B:
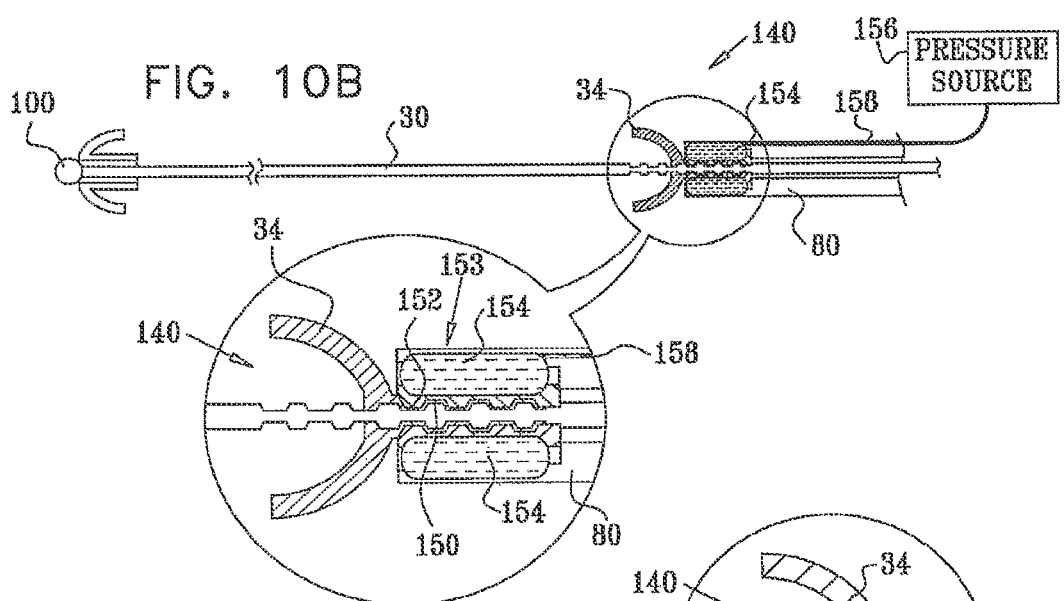
Figure 10C:
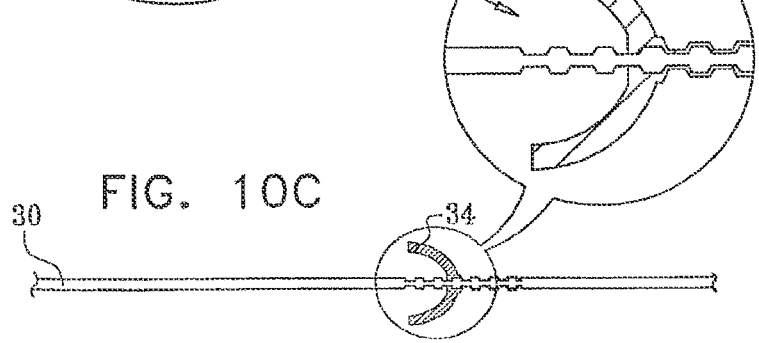

Reference is made to FIGS. 10A-C, which are schematic illustrations of yet another sliding and locking mechanism 140 of band 30, in accordance with an embodiment of the present invention. Mechanism 140 comprises two interlocking sets of teeth. A first set of teeth 150 is coupled to or integrated into a proximal portion of band 30, and a second set of teeth 152 is coupled to or integrated into an interior surface of proximal coupling element 34. When the coupling element is in an unlocked position, the first and second sets of teeth are not engaged with one another, such that the coupling element is able to advance distally over band 30, as shown in FIG. 10A. Catheter 81 comprises a crimping mechanism 153 in a vicinity of a distal end of the catheter. Crimping mechanism 153 typically comprises an expansion element 154, such as a balloon, which is coupled to an external source 156 of fluid (liquid or gas) pressure, via a pressure tube 158. Crimping mechanism 153 is adapted to be placed around the portion of proximal coupling element 34 having second set of teeth 152, as shown in FIG. 10A. Crimping mechanism 153 is configured such that expansion of expansion element 154 pushes second set of teeth 152 into contact with first set of teeth 150, crimping the first and second sets of teeth together, as shown in FIG. 10B. Such crimping locks coupling element 34 in place on band 30.

After crimping, catheter 81 and crimping mechanism 153 are retracted, leaving coupling element 34 in place, as shown in FIG. 10C.

Reference is made to FIGS. 11A-B, which are schematic illustrations of still another sliding and locking mechanism 170, in accordance with an embodiment of the present invention. Mechanism 170 comprises a tension clip 172 that releasably engages one or more indentations 174 in band 30. Tension clip 172 is configured such that in its resting position, coupling portions 176 of the clip engage respective indentations 174, preventing movement of the clip, as shown in FIG. 11A. Applying force to release sites 178 of clip 172 changes the shape of the clip, causing coupling portions 176 to disengage from indentations 174, as shown in FIG. 11B. For some applications, release sites 178 also serve as coupling elements for coupling band 30 to the chordae tendineae, while for other applications, clip 172 comprises separate coupling elements (latter configuration not shown). In an embodiment, catheter 81 comprises one or more force application elements 180, which are configured to apply force to release sites 178, in order to disengage clip 172 from band 30. For some applications, force application elements 180 are inflatable, and are configured such that inflation thereof applies force to release sites 178.

Figure 12A:
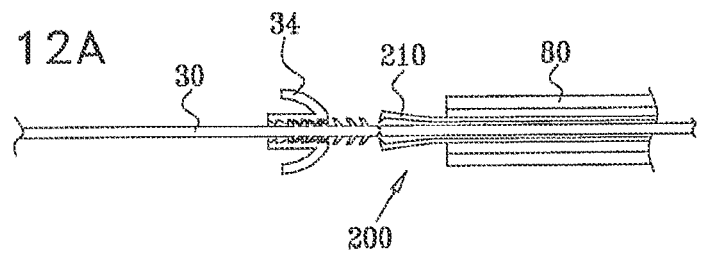
FIGS. 12A-B are schematic illustrations of a band clipping mechanism, in accordance with an embodiment of the present invention.
Figure 12B:
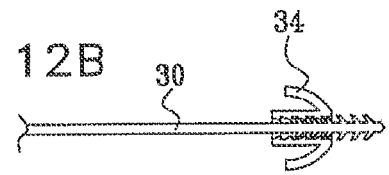

Reference is made to FIGS. 12A-B, which are schematic illustrations of a band clipping mechanism 200, in accordance with an embodiment of the present invention. Clipping mechanism 200 is used to clip the portion of band 30 proximal to proximal coupling element 34, typically after the proximal coupling element has been locked in place. Clipping mechanism 200 comprises clippers 210, which are adapted to be introduced through catheter 81 over the proximal portion of band 30. Clippers 210 clip the band, and the clippers and the proximal portion of the band are withdrawn through catheter 81, leaving the distal portion of band 30 in place in the heart, as shown in FIG. 12B.

Figure 13A:
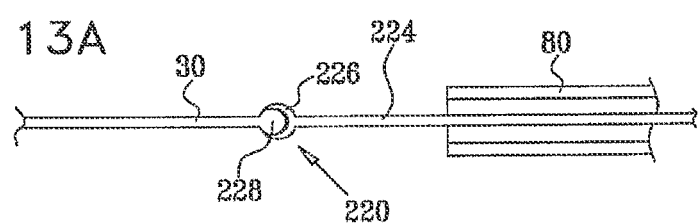
FIGS. 13A-B are schematic illustrations of a band release mechanism, in accordance with an embodiment of the present invention.
Figure 13B:
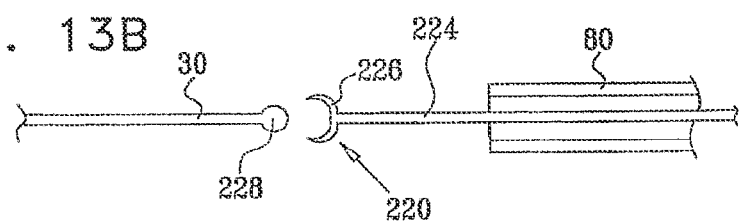

Reference is made to FIGS. 13A-B, which are schematic illustrations of a band release mechanism 220, in accordance with an embodiment of the present invention. The release mechanism is used to release band 30 from an insertion element 224, which is subsequently withdrawn through catheter 81. Therefore, in this embodiment, there is generally no need to clip the band. Release mechanism comprises a grasping element 226, which is adapted to releasably engage the proximal end of band 30. For some applications, the proximal end of band 30 comprises or is shaped to as to define a protrusion 228, such as a spherical protrusion, which grasping element 226 engages. Alternatively, release mechanism 220 comprises another coupling element, such as a screw, which releasably engages the proximal end of band 30.

In an embodiment of the present invention, proximal coupling element 34 does not comprise sliding and locking mechanism 90 or any other length-adjusting mechanism, such that the length of band 30 is fixed. In this embodiment, the surgeon may or may not invasively or non-invasively measure or estimate the circumference of annulus 60 prior to choosing which length of band 30 to implant. For some applications of this embodiment, band 30 comprises band release mechanism 220, described hereinabove with reference to FIGS. 13A-B.

In an embodiment of the present invention, band 30 is configured such that distal and proximal coupling elements 32 and 34 push the chordae tendineae to which they are coupled, rather than pull the chordae. In this embodiment, band 30 is typically stiffer than in some other embodiments described herein.

In an embodiment of the present invention, band 30 comprises one or more supporting members configured to support posterior cusp 56. For some applications, the supporting members protrude from the band.

Figure 14A:
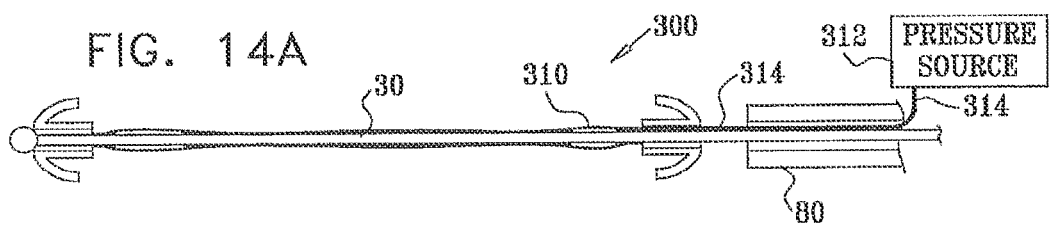
FIGS. 14A-B are schematic illustrations of an inflation mechanism, in accordance with an embodiment of the present invention.
Figure 14B:
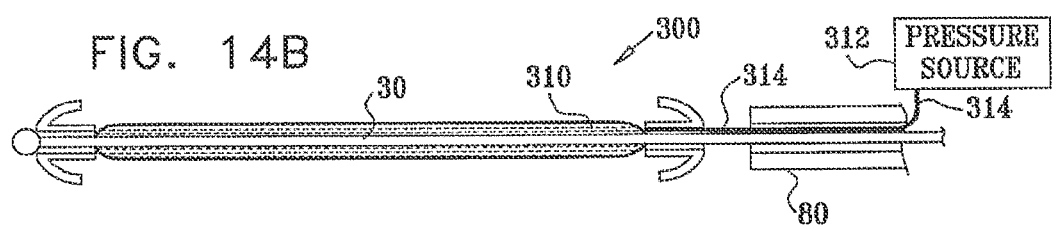

Reference is made to FIGS. 14A-B, which are schematic illustrations of an inflation mechanism 300, in accordance with an embodiment of the present invention. Inflation mechanism 300 comprises an inflatable sheath 310, placed around band 30, and an external source 312 of liquid (fluid or gas) pressure, which is coupled to an interior of sheath 310 via a pressure tube 314. During insertion of band 30, sheath 310 is typically uninflated. After insertion, pressure source 312 inflates sheath 310 by supplying a liquid or gas, such as saline solution, a liquid silicone, a liquid polymer, or a liquid polyurethane. After inflation, sheath 310 is sealed. Such inflation typically increases the support band 30 provides to posterior cusp 56. For some applications, sheath 310 is inflated with a liquid that completely or partially solidifies after inflation, such as into a flexible material.

Figure 15A:
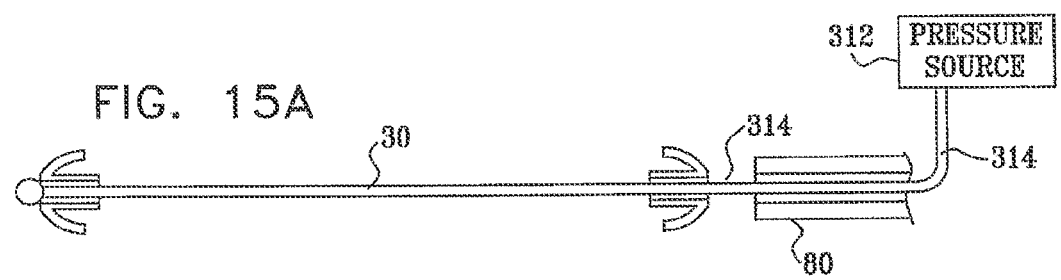
FIGS. 15A-B are schematic illustrations of another inflation technique, in accordance with an embodiment of the present invention.
Figure 15B:
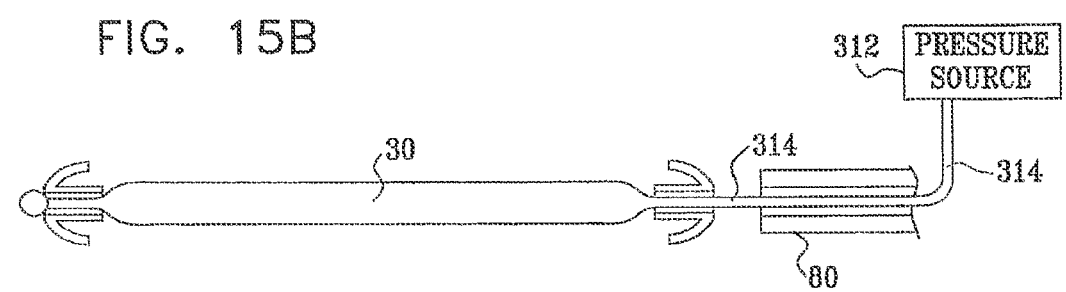

FIGS. 15A-B are schematic illustrations of another inflation technique, in accordance with an embodiment of the present invention. In this embodiment, band 30 is itself inflatable, and sheath 310 need not be provided. The interior of band 30 is in fluid communication with external pressure source 312 via pressure tube 314. This embodiment may employ techniques described hereinabove with reference to FIGS. 14A-B, mutatis mutandis.

FIG. 16 is a schematic illustration of a configuration of band 30, in accordance with an embodiment of the present invention. In this embodiment, band 30 is inflatable, such as by using one of the inflation techniques described hereinabove with reference to FIG. 14A-B or 15A-B. For some applications, inflatable band 30 comprises neither distal coupling element 32 nor proximal coupling element 34, nor any other anchoring means at either the distal or proximal ends of the band. (Alternatively, for some applications, band 30 comprises anchoring means at only a single one of its ends.) After the band is placed around all or a portion of posterior cusp 56, the band is inflated and sealed, causing the band to press against posterior cusp 56, chordae tendineae 74 (or, alternatively, the second-order chordae tendineae), and ventricular wall 70, thereby applying pressure to and supporting the posterior cusp, and typically holding band 30 in place.

Reference is made to FIGS. 17A-B, which are schematic illustrations of a stent 350 adapted for treatment of mitral valve 58, in accordance with an embodiment of the present invention. Stent 350 is adapted to be placed around between 90 and 270 degrees of mitral valve 58, including around at least a portion of posterior cusp 56. For some applications, stent 350 is adapted to be placed around between 120 and 240 degrees, such as between 150 and 210 degrees, e.g., about 180 degrees, of the mitral valve. For some applications, stent 350 is adapted to be placed substantially only around all or a portion of posterior cusp 56, i.e., substantially not around any portion of anterior cusp 59. For example, the length of stent 350 surrounding posterior cusp 56 is typically at least about 5 or at least about 10 times the length of any portion of stent 350 that may be surrounding anterior cusp 59.

Typically, stent 350, while in a contracted position, as shown in FIG. 17A, is placed in the space defined by ventricular wall 70 of left ventricle 72, a ventricular surface of posterior cusp 56 in a vicinity of annulus 60, and chordae tendineae selected from third-order chordae tendineae 74 and second-order chordae tendineae. Once hits desired position, stent 350 is expanded by inflating an inflation element 360 positioned within the stent. Inflation element 360 is removed, leaving stent 350 in place. Expansion of stent 350 applies pressure to and supports posterior cusp 56, and typically holds the stent in place.

For some applications, one or both ends of stent 350 are anchored in place by distal and/or proximal coupling elements (not shown in FIGS. 17A-B, but similar to distal and proximal coupling elements 32 and 34, as described hereinabove). Typically, the distal and proximal coupling elements are coupled to first and second chordae tendineae, respectively, each of which is selected from the group consisting of: one of third-order chordae 74, a first-order chorda tendinea that inserts on a commissural cusp 78 of mitral valve 58 (shown in FIG. 2), and a second-order chorda tendinea (not shown in the figures).

For some applications, a plurality of stents 350 are placed around mitral valve 58. The plurality of stents are typically arranged in series, and are optionally coupled to one another.

In an embodiment of the present invention, a method is provided for removing band 30 after it has been coupled to the chordae tendineae. The method comprises inserting a catheter or other elongated element into the heart, typically via ascending aorta 82, and navigating the catheter around the chordae tendineae in a direction opposite to the direction in which band 30 was navigated around the chordae during insertion of the band. When the catheter reaches the distal end of band 30, the catheter is coupled to the distal end. The catheter is then withdrawn, such that band 30 is pulled in the same direction as during the band's initial insertion. For example, if band 30 is initially inserted in a counterclockwise direction around the mitral valve as viewed from the left atrium, the catheter is inserted in a clockwise direction, and the catheter is withdrawn, pulling band 30, in a counterclockwise direction. Typically, before removing band 30, proximal coupling element 34 is removed from the band. For some applications, distal stop 100 is magnetic, and the catheter is magnetically coupled to the distal stop.

It will be appreciated that whereas band 30 has been generally described herein as comprising a single band, the scope of the present invention is not limited to a single band, and includes the use of multiple bands in series and/or in parallel with one another.

FIG. 18 is a schematic illustration of a mitral valve treatment outward force applicator 430 placed in heart 50, which is viewed from above the heart with the atria removed, in accordance with an embodiment of the present invention. Force applicator 430 is typically flexible, and, for some applications, is generally elliptical in cross-section (e.g., circular), while for other applications is flat, e.g., ribbon-shaped. Force applicator 430 typically comprises a biocompatible material, such as a polymer or metal. For some applications, force applicator 430 is coated with a drug and/or a radiopaque coating.

Force applicator 430 is adapted to be placed around between 90 and 270 degrees of mitral valve 58 of heart 50, in a vicinity of annulus 60 of mitral valve 58. The ends of force applicator 430 are typically, but not necessarily, positioned in a vicinity of commissural cusps 78 of mitral valve 58. Force applicator 430 is configured such that at least two regions thereof (typically end regions 462) apply force, symbolically indicated by arrows 464, to a wall 466 of a heart chamber in a vicinity of commissural cusps 78. The heart chamber is the left ventricle and/or the left atrium. Such outwardly-applied force draws commissural cusps 78 away from one another, stretching mitral valve 58 and thereby bringing posterior cusp 56 and anterior cusp 59 of mitral valve 58 closer to one another.

For some applications, force applicator 430 is adapted to be placed around between 120 and 240 degrees, such as between 150 and 210 degrees, e.g., about 180 degrees, of mitral valve 58. For some applications, force applicator 430 is adapted to be placed substantially only around all or a portion of posterior cusp 56, i.e., substantially not around any portion of anterior cusp 59. For example, for these applications, the length of force applicator 430 surrounding posterior cusp 56 may be at least about 5 or at least about 10 times the length of any portion of force applicator 430 that may be surrounding anterior cusp 59. For other applications, force applicator 430 is adapted to be placed around all or a portion of anterior cusp 59, and not necessarily around any portion of posterior cusp 56.

Figure 19A:
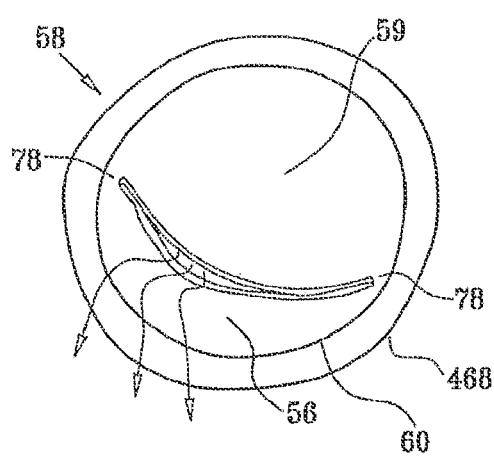
FIGS. 19A and 19B are schematic illustrations of a mitral valve before and after placement of the force applicator of FIG. 18, respectively, in accordance with an embodiment of the present invention.
Figure 19B:
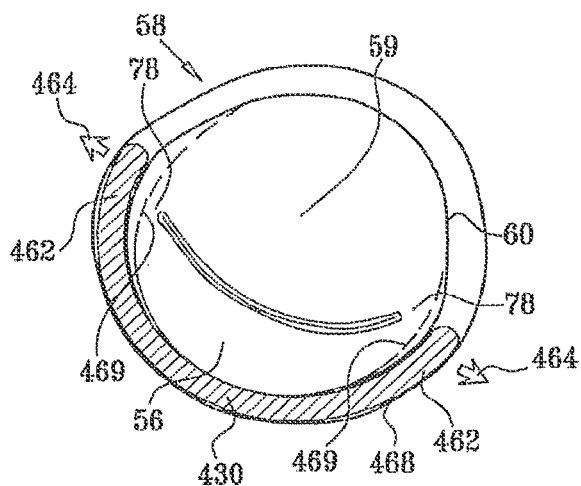

Reference is made to FIGS. 19A and 19B, which are schematic illustrations of mitral valve 58 before and after placement of force applicator 430, respectively, in accordance with an embodiment of the present invention. FIG. 19A shows mitral valve 58 during systole, prior to the placement of force applicator 430. Posterior cusp 56 and anterior cusp 59 are slightly separated from one another, causing mitral valve regurgitation. FIG. 19B shows force applicator 430 placed around posterior cusp 56, and applying outward force (indicated by arrows 464) on a wall 468 of a heart chamber. Such outwardly-applied force draws commissural cusps 78 away from one another, stretching mitral valve 58 and thereby forcing posterior cusp 56 and anterior cusp 59 of mitral valve 58 closer to one another, and thereby preventing regurgitation. (Broken lines 469 show the shape of annulus 60 prior to placement of force applicator 430, for the sake of comparison with FIG. 19A.)

Figure 20:
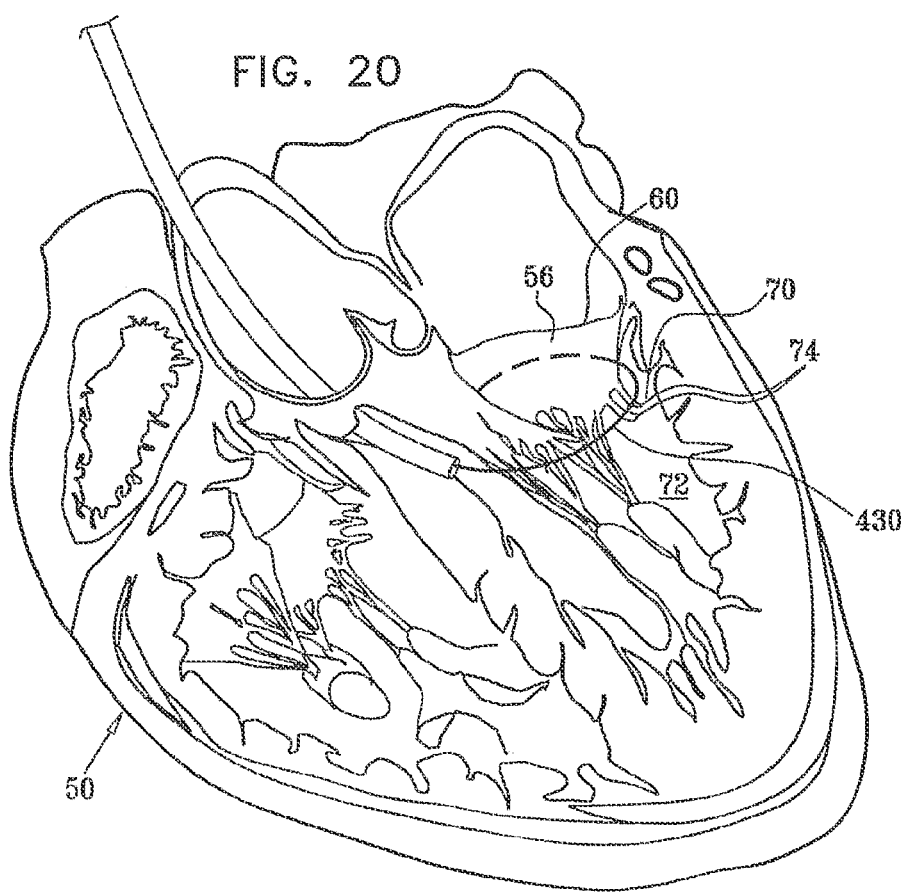
FIG. 20 is a schematic illustration of a portion of the force applicator of FIG. 18 placed around a portion of a posterior cusp of the mitral valve, in accordance with an embodiment of the present invention.

Reference is made to FIG. 20, which is a schematic illustration of a portion of force applicator 430 placed around a portion of posterior cusp 56, in accordance with an embodiment of the present invention. For some applications, force applicator 430 is placed in the space defined by ventricular wall 70 of left ventricle 72, a ventricular surface of posterior cusp 56 in a vicinity of annulus 60, and third-order chordae tendineae 74 (also called tertiary or basal chordae). (Third-order chordae 74, of which only two of many are shown in the figure for clarity of illustration, originate directly from the trabeculae carneae of ventricular wall 70, and attach to posterior cusp 56 in a vicinity of annulus 60.) Alternatively or additionally, the space is defined by second-order chordae tendineae (not shown in the figure). Further alternatively, force applicator 430 is adapted to be placed in a left atrium of the heart, in contact with or in a vicinity of mitral valve 58 (configuration not shown).

Figure 21A:
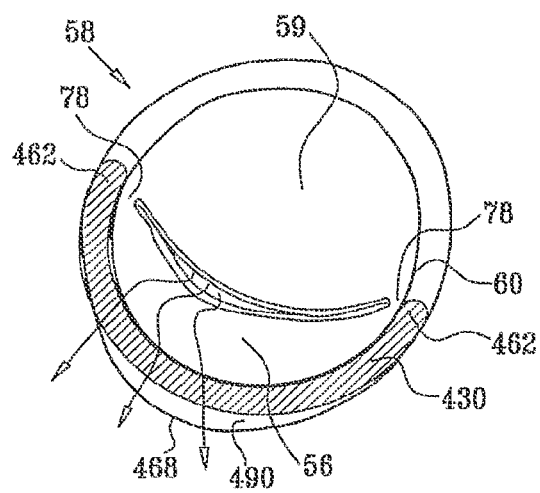
FIGS. 21A and 21B are schematic illustrations of the mitral valve before and after expansion of the force applicator of FIG. 18, respectively, in accordance with an embodiment of the present invention.
Figure 21B:
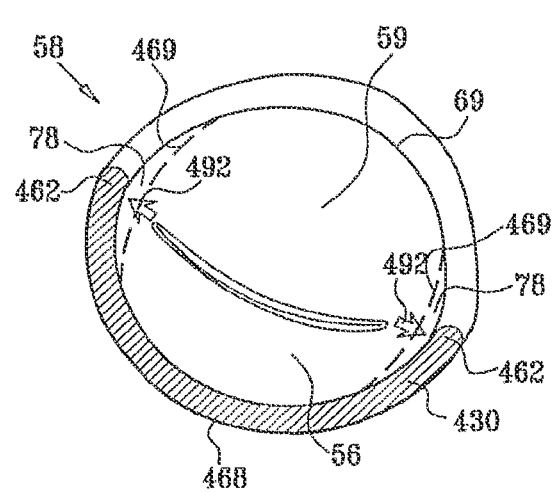

Reference is made to FIGS. 21A and 21B, which are schematic illustrations of mitral valve 58 before and after expansion of, force applicator 430, respectively, in accordance with an embodiment of the present invention. FIG. 21A shows mitral valve 58 during systole, immediately after placement of force applicator 430, but prior to the outward expansion of the force applicator. Force applicator 430 is configured and placed such that there is a gap 490 between the force applicator and dilated wall 468 of the heart chamber. Posterior cusp 56 and anterior cusp 59 are slightly separated from one another, causing mitral valve regurgitation. FIG. 21B shows force applicator 430 after outward expansion of ends 462 of the force applicator, as symbolically indicated by arrows 492. Such outwardly-applied force, in addition to drawing commissural cusps 78 away from one another, draws heart wall 468 closer to force applicator 430 in a vicinity of gap 490. Such tightening of wall 468 against force applicator 430 may occur immediately upon outward expansion of force applicator 430, or may occur over time, e.g., within about one month of expansion of force applicator 430, as the heart adapts to and heals because of the placement of the force applicator.

In an embodiment of the present invention, a surface of force applicator 430 opposite heart wall 468 is configured to enhance fibrosis between the force applicator and the heart wall. For example, the surface may be roughened, and/or coated with a fibrosis-enhancing substance. The fibrosis holds tissue of the heart wall against the force applicator, thereby helping prevent future dilation of the heart. Thus, force applicator 430 actively changes the shape of the heart around the mitral valve, and the fibrosis helps maintain this new shape.

Figure 22:
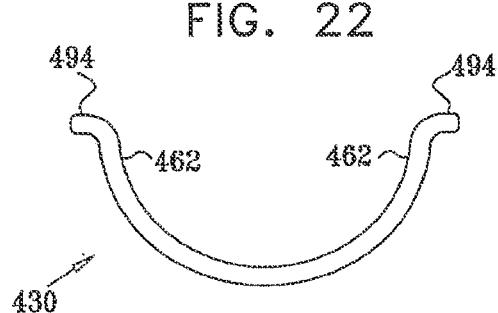
FIGS. 22 and 23 are schematic illustrations of respective configurations of the force applicator of FIG. 18, in accordance with respective embodiments of the present invention.

Reference is made to FIG. 22, which is a schematic illustration of a configuration of force applicator 430, in accordance with an embodiment of the present invention. In this configuration, force applicator 430 comprises or is shaped to define one or more protruding extensions 94 at one or both ends 462 of the force applicator. The extensions increase the outward pushing of the force applicator on the heart wall.

Figure 23:
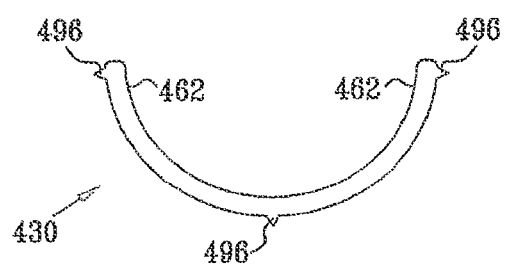

Reference is made to FIG. 23, which is a schematic illustration of another configuration of force applicator 430, in accordance with an embodiment of the present invention. In this configuration, force applicator 430 comprises or is shaped to define one or more coupling elements, which are adapted to hold the force applicator in place after placement. For some applications, the coupling elements comprise one or more protrusions 496, oriented on the force applicator such that the protrusions contact and grip the wall of the heart. Typically, protrusions 496 are positioned in a vicinity of ends 462 of force applicator 430, and/or along the length of the force applicator, such as in a vicinity of a middle of the force applicator. For some applications, protrusions 496 are positioned at the ends of protruding extensions 494, described hereinabove with reference to FIG. 22 (configuration not shown). For other applications, the coupling elements are adapted to be coupled to the mitral valve, and/or to one or more chordae tendineae, such as third-order chordae tendineae 74, or second-order chordae tendineae (not shown in the figures). For these applications, the coupling elements may comprise, for example, hooks, sutures, or staples (configuration not shown).

Figure 24:
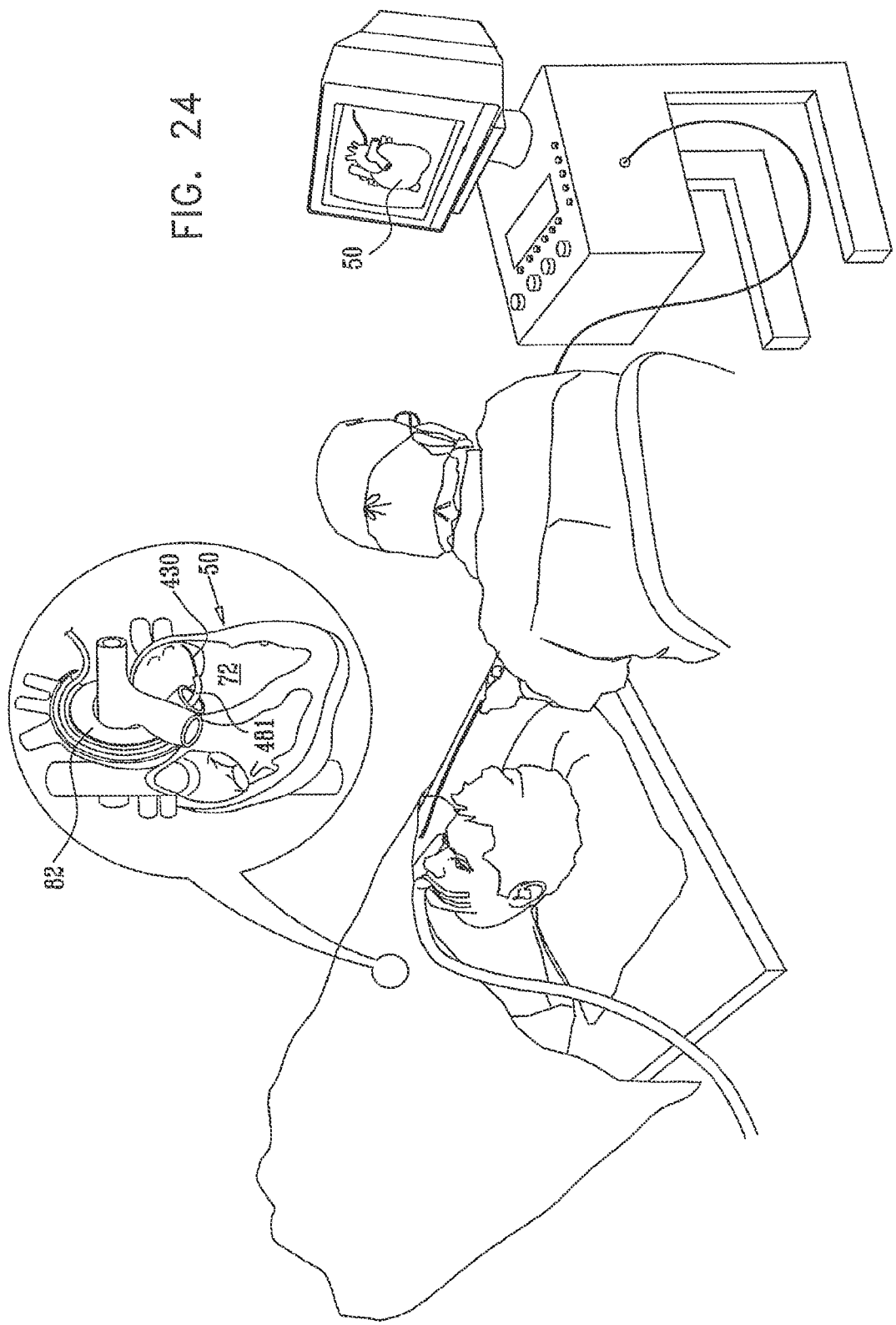
FIG. 24 is a schematic illustration of a procedure for introducing the force applicator of FIG. 18 into the heart of a subject, in accordance with an embodiment of the present invention.

Reference is made to FIG. 24, which is a schematic illustration of a procedure for introducing force applicator 430 into heart 50 of a subject, in accordance with an embodiment of the present invention. Typically, force applicator 430 is introduced into ventricle 72 by a catheter 481, which is typically introduced into ventricle 72 via ascending aorta 82. A surgeon typically guides force applicator 430 to a desired location using images of heart 50 captured using techniques known in the art. Alternatively or additionally, the surgeon employs an echocardiogram to determine if placement of force applicator 430 achieves closure of the mitral valve. For some applications, force applicator 430 is adjustable during placement, for example, as described hereinbelow with reference to FIG. 26 and/or FIG. 27. For such applications, if the device does not sufficiently close the valve, the surgeon may adjust the device in situ until the valve is sufficiently closed.

For some applications, force applicator 430 comprises, e.g., at a distal end thereof, one or more wireless position sensors, such as those manufactured by Biosense, Inc. (New Brunswick, N.J.), or otherwise known in the art. Alternatively or additionally, force applicator 430 comprises, e.g., at a distal end thereof, one or more sensors for aiding navigation, such as an ultrasound sensor, an infrared sensor, or an optical sensor. For some applications, force applicator 430 comprises a steering mechanism, such as those known in the art of coronary catheter navigation. For some applications, the surgeon magnetically navigates force applicator 430, such as using techniques described in U.S. Pat. No. 6,817,364 or 6,522,909 to Garibaldi et al., or U.S. Pat. No. 6,475,223 to Werp et al., which are incorporated herein by reference, mutatis mutandis.

Figure 25:
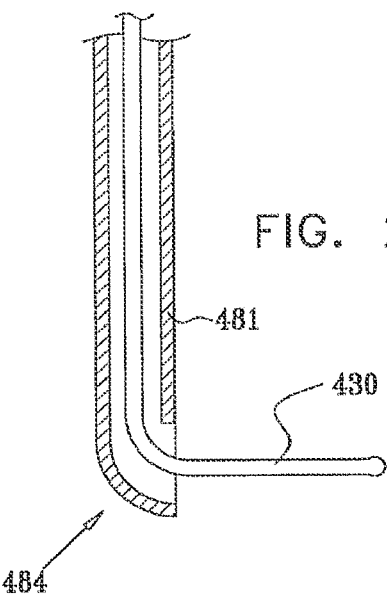
FIG. 25 is a schematic illustration of a distal end of a catheter for introducing the force applicator of FIG. 18 into the heart, in accordance with an embodiment of the present invention.

Reference is made to FIG. 25, which is a schematic illustration of a distal end 484 of catheter 481, in accordance with an embodiment of the present invention. In this embodiment, the distal end of catheter 481 opens laterally, rather than at its end, so as to guide force applicator 430 towards mitral valve 58 after the catheter is inserted into left ventricle 72.

Figure 26:
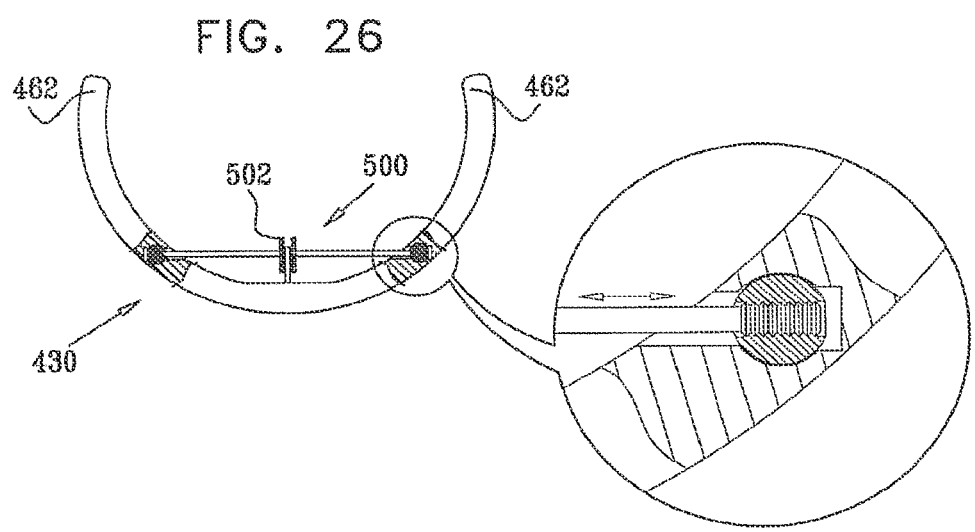
FIGS. 26 and 27 are schematic illustrations of respective adjustment mechanisms for the force applicator of FIG. 18, in accordance with respective embodiments of the present invention.

Reference is made to FIG. 26, which is a schematic illustration of an adjustment mechanism 500 for force applicator 430, in accordance with an embodiment of the present invention. Adjustment mechanism 500 comprises a center wheel 502, which is configured to move ends 462 of force applicator 430 closer and farther from one another, in a manner similar to a center wheel of a draftsman's compass.

Figure 27:
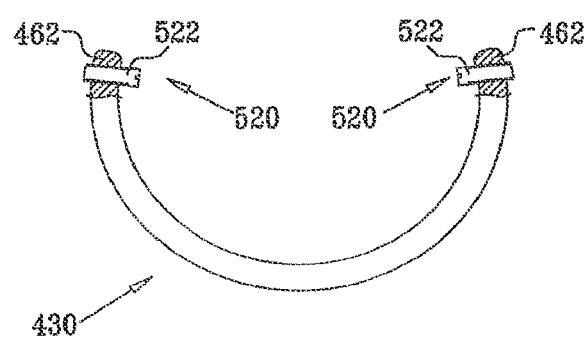

Reference is made to FIG. 27, which is a schematic illustration of another adjustment mechanism 520 for force applicator 430, in accordance with an embodiment of the present invention. Adjustment mechanism 520 comprises one or more screws 522 in a vicinity of one or both ends 462 of force applicator 430. Rotation of screws 522 in one direction increases the pushing of end 462 into the heart wall, while rotation of the screws in the opposite direction decreases such pushing. For some applications, force applicator 430 comprises both adjustment mechanism 520 and adjustment mechanism 500, described hereinabove with reference to FIG. 26.

It will be appreciated that whereas force applicator 430 has been generally described herein as comprising a single force applicator, the scope of the present invention is not limited to a single force applicator, and includes the use of multiple force applicators in series and/or in parallel with one another.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. A method for treating a heart valve of a patient, the method comprising:
    inserting into a heart of the patient and in contact with a valve surface of the heart valve, an implant including an elongate element and a locking mechanism coupled to the elongate element, the locking mechanism having a resting position that provides a locked state in which movement of the elongate element with respect to the locking mechanism is prevented;
    subsequently to the inserting, performing annuloplasty on the heart valve of the patient by increasing tension of the elongate element by maintaining application of a force to the locking mechanism using a tool, and thereby maintaining the locking mechanism in an unlocked state during the increasing of the tension of the elongate element; and
    subsequently to the performing of the annuloplasty on the heart valve and subsequently to coupling proximal and distal ends of the implant to tissue at the heart valve, transitioning the locking mechanism to the resting position by decoupling the tool from the locking mechanism.

2. The method according to claim 1, wherein inserting comprises positioning the implant in contact with a ventricular surface of the heart valve.

3. The method according to claim 1, wherein increasing the tension of the elongate element comprises facilitating sliding of the locking mechanism along the elongate element.

4. The method according to claim 1, wherein the locking mechanism includes a clip, and wherein transitioning the locking mechanism to the resting position comprises facilitating changing a shape of the clip.

5. The method according to claim 1, wherein:
    the locking mechanism is shaped so as to define one or more release sites,
    the tool includes one or more force application elements, and
    maintaining application of the force to the locking mechanism using the tool comprises maintaining application of the force to the one or more release sites of the locking mechanism by a respective one of the one or more force application elements of the tool.

6. The method according to claim 1, wherein performing of the annuloplasty on the heart valve comprises tightening an annulus of the valve.

7. The method according to claim 1, wherein inserting the implant comprises inserting the elongate element and the locking mechanism at the same time.

8. The method according to claim 1, wherein inserting the implant comprises inserting the elongate element and the locking mechanism while the elongate element is coupled to the locking mechanism.

9. The method according to claim 1, wherein coupling the proximal and distal ends of the implant comprises:
    coupling a proximal coupling element at the proximal end of the implant to a first portion of chordae tendineae; and
    coupling a distal coupling element at the distal end of the implant to a second portion of chordae tendineae.

10. The method according to claim 1, wherein maintaining the locking mechanism in the unlocked state comprises, using the tool, changing a shape of the locking mechanism and maintaining a changed shape of the locking mechanism during the performing of the annuloplasty.

11. The method according to claim 10, wherein changing the shape of the locking mechanism comprises applying a force to a portion of the locking mechanism in order to facilitate the changing of the shape.

12. The method according to claim 1, wherein inserting comprises transcatheterally inserting.

13. The method according to claim 1, wherein increasing the tension comprises adjusting the tension of the elongate element based on feedback.

14. A method for treating a heart valve of a patient, the method comprising:
    inserting into a heart of the patient and in contact with a valve surface of the heart valve an implant including an elongate element and only one locking mechanism coupled to the elongate element, the locking mechanism having a resting position that provides a locked state in which movement of the elongate element with respect to the locking mechanism is prevented; and while a tool is engaged with the locking mechanism, performing annuloplasty on the heart valve of the patient by, using the tool:
  applying a force to the locking mechanism and thereby transitioning the locking mechanism out of the resting position into an unlocked state; and
  increasing a tension of the elongate element; and
subsequently to the performing of the annuloplasty on the heart valve, transitioning the locking mechanism to the resting position by decoupling the tool from the locking mechanism.

15. The method according to claim 14, wherein inserting comprises positioning the implant in contact with a ventricular surface of the heart valve.

16. The method according to claim 14, wherein increasing the tension of the elongate element comprises facilitating sliding of the locking mechanism along the elongate element.

17. The method according to claim 14, wherein the locking mechanism includes a clip wherein transitioning the locking mechanism out of the resting position comprises facilitating changing a shape of the clip.

18. The method according to claim 14, wherein:
  the locking mechanism is shaped so as to define one or more release sites,
  the tool includes one or more force application elements, and
  applying the force to the locking mechanism comprises applying the force to the one or more release sites of the locking mechanism by a respective one of the one or more force application elements of the tool.

19. The method according to claim 14, wherein performing the annuloplasty on the heart valve comprises tightening an annulus of the valve.

20. The method according to claim 14, wherein inserting the implant comprises inserting the elongate element and the locking mechanism at the same time.

21. The method according to claim 14, wherein inserting the implant comprises inserting the elongate element and the locking mechanism while the elongate element is coupled to the locking mechanism.

22. The method according to claim 14, further comprising coupling proximal and distal ends of the elongate element to respective portions of heart tissue.

23. The method according to claim 22, wherein coupling the proximal and distal ends of the elongate element comprises:
  coupling a proximal coupling element at the proximal end of the elongate element to a first portion of chordae tendineae; and
  coupling a distal coupling element at the distal end of the elongate element to a second portion of chordae tendineae.

24. The method according to claim 14, wherein applying the force to the locking mechanism comprises, using the tool, changing a shape of the locking mechanism and maintaining a changed shape of the locking mechanism during the performing of the annuloplasty.

25. The method according to claim 14, wherein inserting comprises transcatheterally inserting.

26. The method according to claim 14, wherein increasing the tension comprises adjusting the tension of the elongate element based on feedback.

* * * * *